US008353440B2

(12) United States Patent
Whitman et al.

(10) Patent No.: US 8,353,440 B2
(45) Date of Patent: Jan. 15, 2013

(54) SURGICAL DEVICE HAVING A ROTATABLE JAW PORTION

(75) Inventors: Michael P. Whitman, New Hope, PA (US); Donald Malinouskas, Monroe, CT (US); Peter Datcuk, Quakertown, PA (US); David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/162,811

(22) Filed: Jun. 17, 2011

(65) Prior Publication Data
US 2011/0240714 A1 Oct. 6, 2011

Related U.S. Application Data

(63) Continuation of application No. 13/027,292, filed on Feb. 15, 2011, now Pat. No. 7,992,758, which is a continuation of application No. 12/235,386, filed on Sep. 22, 2008, now Pat. No. 7,918,230.

(60) Provisional application No. 60/974,291, filed on Sep. 21, 2007.

(51) Int. Cl.
*A61B 17/068* (2006.01)

(52) U.S. Cl. ........... 227/180.1; 227/19; 227/175.1

(58) Field of Classification Search ......... 227/180.1, 227/19, 1, 75.1; 606/170, 208
See application file for complete search history.

(56) References Cited

U.S. PATENT DOCUMENTS

| 1,798,902 A | 3/1931 | Raney |
| 1,881,250 A | 10/1932 | Tomlinson |
| 1,881,706 A | 10/1932 | Larsen |
| 2,031,682 A | 2/1936 | Wappler et al. |
| 2,174,219 A | 9/1939 | Balma |
| 2,226,789 A | 12/1940 | Tupy |
| 2,229,800 A | 1/1941 | Dean |
| 2,246,647 A | 6/1941 | Vancura |
| 2,355,086 A | 8/1944 | Lang |
| 2,419,045 A | 4/1947 | Whittaker |
| 2,725,628 A | 12/1955 | O'Neilly et al. |
| 3,017,637 A | 1/1962 | Sampson |
| 3,079,606 A | 3/1963 | Bobrov et al. |
| 3,120,845 A | 2/1964 | Horner |

(Continued)

FOREIGN PATENT DOCUMENTS

| DE | 23 30 182 | 1/1975 |
| DE | 29 03 159 | 7/1980 |
| DE | 31 14 135 | 10/1982 |
| DE | 33 00 768 | 7/1984 |
| DE | 42 13 426 | 10/1992 |

(Continued)

OTHER PUBLICATIONS

International Search Report corresponding to PCT Application No. PCT/US2006/029287, completed Jun. 25, 2007 and mailed Aug. 27, 2007; 1 page.

(Continued)

*Primary Examiner* — Brian D Nash

(57) ABSTRACT

A surgical device is provided that includes a jaw portion, having a first jaw in opposed correspondence with a second jaw, the second jaw including a surgical member. The surgical device may include a shaft portion coupled to a proximal end of the jaw portion and at least one motor configured to rotate the jaw portion relative to the shaft portion, to move the jaw portion relative to the shaft portion, move the first jaw relative to the second jaw and move the surgical member within the second jaw. The surgical member may be prevented from moving within the second jaw unless the first jaw is in a closed position relative to the second jaw. Advantageously, the surgical member may be, e.g., a cutting element and/or a stapling element, disposed within one of the jaws.

29 Claims, 39 Drawing Sheets

U.S. PATENT DOCUMENTS

| | | | |
|---|---|---|---|
| 3,193,165 A | 7/1965 | Akhalaya et al. |
| 3,252,643 A | 5/1966 | Strekopytov et al. |
| 3,252,880 A | 5/1966 | Magat et al. |
| 3,253,643 A | 5/1966 | Gudheim |
| 3,256,875 A | 6/1966 | Tsepelev et al. |
| 3,269,631 A | 8/1966 | Takaro |
| 3,275,211 A | 9/1966 | Hirsch et al. |
| 3,315,863 A | 4/1967 | O'Dea |
| 3,317,105 A | 5/1967 | Astafjev et al. |
| 3,388,847 A | 6/1968 | Kasulin, et al. |
| 3,490,576 A | 1/1970 | Alossi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafjev et al. |
| 3,618,842 A | 11/1971 | Bryan |
| 3,638,652 A | 2/1972 | Kelley |
| 3,643,851 A | 2/1972 | Green |
| 3,662,939 A | 5/1972 | Bryan |
| 3,675,688 A | 7/1972 | Bryan et al. |
| 3,692,224 A | 9/1972 | Astafjev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles et al. |
| 3,858,577 A | 1/1975 | Bass et al. |
| 3,859,986 A | 1/1975 | Okada et al. |
| 3,879,104 A | 4/1975 | Shugarman et al. |
| 3,882,854 A | 5/1975 | Hulka et al. |
| 3,892,228 A | 7/1975 | Mitsui |
| 3,902,614 A | 9/1975 | Roberts et al. |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 3,985,050 A | 10/1976 | Lurie |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,354,628 A | 10/1982 | Green |
| 4,360,110 A | 11/1982 | Sigman et al. |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,484,775 A | 11/1984 | Norkus |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,534,420 A | 8/1985 | Goldelius |
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,573,727 A | 3/1986 | Iikura |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,600,357 A | 7/1986 | Coules |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| D286,567 S | 11/1986 | Lichtman et al. |
| 4,623,183 A | 11/1986 | Aomori |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,676,542 A | 6/1987 | Besold |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |
| 4,728,020 A | 3/1988 | Green et al. |
| 4,732,156 A | 3/1988 | Nakamura |
| 4,733,118 A | 3/1988 | Mihalko |

| | | | | | |
|---|---|---|---|---|---|
| 4,742,815 A | 5/1988 | Ninan et al. | 5,170,925 A | 12/1992 | Madden et al. |
| 4,752,024 A | 6/1988 | Green et al. | 5,171,247 A | 12/1992 | Hughett et al. |
| 4,754,909 A | 7/1988 | Barker et al. | 5,171,251 A | 12/1992 | Bregen et al. |
| 4,756,309 A | 7/1988 | Sachse et al. | 5,173,133 A | 12/1992 | Morin et al. |
| 4,760,840 A | 8/1988 | Fournier, Jr. et al. | 5,192,292 A | 3/1993 | Cezana et al. |
| 4,763,669 A | 8/1988 | Jaeger | 5,197,649 A | 3/1993 | Bessler et al. |
| 4,767,044 A | 8/1988 | Green | 5,201,325 A | 4/1993 | McEwen et al. |
| 4,771,774 A | 9/1988 | Simpson et al. | 5,201,501 A | 4/1993 | Fassler |
| 4,776,506 A | 10/1988 | Green | 5,201,750 A | 4/1993 | Höcherl et al. |
| 4,781,186 A | 11/1988 | Simpson et al. | 5,205,459 A | 4/1993 | Brinkerhoff et al. |
| 4,784,137 A | 11/1988 | Kulik et al. | 5,207,691 A | 5/1993 | Nardella |
| 4,784,422 A | 11/1988 | Jones et al. | 5,207,697 A | 5/1993 | Carusillo et al. |
| 4,789,090 A | 12/1988 | Blake, III | 5,217,003 A | 6/1993 | Wilk |
| 4,796,793 A | 1/1989 | Smith et al. | 5,217,460 A | 6/1993 | Knoepfler |
| 4,805,823 A | 2/1989 | Rothfuss | 5,221,279 A | 6/1993 | Cook et al. |
| 4,815,469 A | 3/1989 | Cohen et al. | 5,224,951 A | 7/1993 | Freitas |
| 4,817,847 A | 4/1989 | Redtenbacher et al. | 5,226,426 A | 7/1993 | Yoon |
| 4,819,632 A | 4/1989 | Davies | 5,237,884 A | 8/1993 | Seto |
| 4,819,853 A | 4/1989 | Green | 5,243,967 A | 9/1993 | Hibino |
| 4,841,888 A | 6/1989 | Mills et al. | 5,249,583 A | 10/1993 | Mallaby |
| 4,848,637 A | 7/1989 | Pruitt | 5,253,793 A | 10/1993 | Green |
| 4,858,608 A | 8/1989 | McQuilkin | 5,254,117 A | 10/1993 | Rigby et al. |
| 4,863,088 A | 9/1989 | Redmond et al. | 5,258,004 A | 11/1993 | Bales et al. |
| 4,867,158 A | 9/1989 | Sugg | 5,258,007 A | 11/1993 | Spetzler et al. |
| 4,869,415 A | 9/1989 | Fox | 5,258,008 A | 11/1993 | Wilk |
| 4,873,977 A | 10/1989 | Avant et al. | 5,261,877 A | 11/1993 | Fine et al. |
| 4,887,599 A | 12/1989 | Muller | 5,267,997 A | 12/1993 | Farin et al. |
| 4,887,612 A | 12/1989 | Esser et al. | 5,268,622 A | 12/1993 | Philipp |
| 4,890,602 A | 1/1990 | Hake | 5,271,543 A | 12/1993 | Grant et al. |
| 4,892,244 A | 1/1990 | Fox et al. | 5,271,544 A | 12/1993 | Fox et al. |
| 4,893,613 A | 1/1990 | Hake | RE34,519 E | 1/1994 | Fox et al. |
| 4,893,622 A | 1/1990 | Green et al. | 5,275,322 A | 1/1994 | Brinkerhoff et al. |
| 4,903,697 A | 2/1990 | Resnick et al. | 5,275,323 A | 1/1994 | Schulze et al. |
| 4,907,591 A | 3/1990 | Vasconcellos et al. | 5,275,609 A | 1/1994 | Pingleton et al. |
| 4,907,973 A | 3/1990 | Hon | 5,279,565 A | 1/1994 | Klein et al. |
| 4,917,114 A | 4/1990 | Green et al. | 5,285,945 A | 2/1994 | Brinkerhoff et al. |
| 4,919,152 A | 4/1990 | Ger | 5,289,963 A | 3/1994 | McGarry et al. |
| 4,928,699 A | 5/1990 | Sasai | 5,290,299 A | 3/1994 | Fain et al. |
| 4,930,494 A | 6/1990 | Takehana et al. | 5,290,303 A | 3/1994 | Pingleton et al. |
| 4,932,960 A | 6/1990 | Green et al. | 5,292,053 A | 3/1994 | Bilotti et al. |
| 4,936,845 A | 6/1990 | Stevens | 5,295,990 A | 3/1994 | Levin |
| 4,941,454 A | 7/1990 | Wood et al. | 5,300,087 A | 4/1994 | Knoepfler |
| 4,941,623 A | 7/1990 | Pruitt | 5,307,976 A | 5/1994 | Olson et al. |
| 4,944,093 A | 7/1990 | Falk | 5,312,023 A | 5/1994 | Green et al. |
| 4,944,443 A | 7/1990 | Oddsen et al. | 5,312,434 A | 5/1994 | Crainich |
| 4,955,882 A | 9/1990 | Hakky | 5,318,221 A | 6/1994 | Green et al. |
| 4,955,959 A | 9/1990 | Tompkins et al. | 5,320,627 A | 6/1994 | Sorensen et al. |
| 4,957,499 A | 9/1990 | Lipatov et al. | 5,322,055 A | 6/1994 | Davison et al. |
| 4,962,877 A | 10/1990 | Hervas | 5,324,288 A | 6/1994 | Billings et al. |
| 4,976,688 A | 12/1990 | Rosenblum | 5,324,300 A | 6/1994 | Elias et al. |
| 4,976,710 A | 12/1990 | Mackin | 5,326,013 A | 7/1994 | Green et al. |
| 4,977,900 A | 12/1990 | Fehling et al. | 5,330,471 A | 7/1994 | Eggers |
| 4,978,049 A | 12/1990 | Green | 5,330,486 A | 7/1994 | Wilk |
| 4,982,726 A | 1/1991 | Taira | 5,333,772 A | 8/1994 | Rothfuss et al. |
| 4,991,764 A | 2/1991 | Mericle | 5,333,773 A | 8/1994 | Main et al. |
| 4,994,060 A | 2/1991 | Rink et al. | 5,336,229 A | 8/1994 | Noda |
| 4,995,877 A | 2/1991 | Ams et al. | 5,342,299 A | 8/1994 | Snoke et al. |
| 5,005,749 A | 4/1991 | Aranyi | 5,342,381 A | 8/1994 | Tidemand |
| 5,018,657 A | 5/1991 | Pedlick et al. | 5,342,382 A | 8/1994 | Brinkerhoff et al. |
| 5,031,814 A | 7/1991 | Tompkins et al. | 5,344,420 A | 9/1994 | Hilal et al. |
| 5,040,715 A | 8/1991 | Green et al. | 5,350,104 A | 9/1994 | Main et al. |
| 5,059,203 A | 10/1991 | Husted | 5,352,222 A | 10/1994 | Rydell |
| 5,065,929 A | 11/1991 | Schulze et al. | 5,352,223 A | 10/1994 | McBrayer et al. |
| D322,143 S | 12/1991 | Spreckelmeier | 5,352,235 A | 10/1994 | Koros et al. |
| 5,071,430 A | 12/1991 | De Salis et al. | 5,354,266 A | 10/1994 | Snoke |
| 5,077,506 A | 12/1991 | Krause | 5,356,408 A | 10/1994 | Rydell |
| 5,100,041 A | 3/1992 | Storace | 5,358,506 A | 10/1994 | Green et al. |
| 5,104,025 A | 4/1992 | Main et al. | 5,364,001 A | 11/1994 | Bryan |
| 5,108,391 A | 4/1992 | Flachenecker et al. | 5,364,409 A | 11/1994 | Kuwabara et al. |
| 5,114,065 A | 5/1992 | Storace | 5,366,133 A | 11/1994 | Geiste |
| 5,119,983 A | 6/1992 | Green et al. | 5,366,476 A | 11/1994 | Noda |
| 5,129,570 A | 7/1992 | Schulze et al. | 5,368,015 A | 11/1994 | Wilk |
| 5,133,359 A | 7/1992 | Kedem | 5,368,607 A | 11/1994 | Freitas |
| 5,133,713 A | 7/1992 | Huang et al. | 5,370,294 A | 12/1994 | Bauer |
| 5,133,729 A | 7/1992 | Sjostrom | 5,380,321 A | 1/1995 | Yoon |
| 5,139,513 A | 8/1992 | Segato | 5,381,943 A | 1/1995 | Allen et al. |
| 5,156,315 A | 10/1992 | Green et al. | 5,383,880 A | 1/1995 | Hooven |
| 5,157,837 A | 10/1992 | Rose | 5,389,098 A | 2/1995 | Tsuruta et al. |
| 5,158,222 A | 10/1992 | Green | 5,391,156 A | 2/1995 | Hildwein et al. |

| | | |
|---|---|---|
| 5,392,789 A | 2/1995 | Slater et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,441,507 A | 8/1995 | Wilk |
| 5,443,198 A | 8/1995 | Viola et al. |
| 5,447,265 A | 9/1995 | Vidal et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,465,895 A | 11/1995 | Knodel et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,478,003 A | 12/1995 | Green et al. |
| 5,482,054 A | 1/1996 | Slater et al. |
| 5,482,197 A | 1/1996 | Green et al. |
| 5,484,095 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,490,813 A | 2/1996 | Danielsen et al. |
| 5,496,269 A | 3/1996 | Snoke |
| 5,496,317 A | 3/1996 | Goble et al. |
| 5,496,333 A | 3/1996 | Sackier et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,935 A | 7/1996 | Vidal et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| 5,562,677 A | 10/1996 | Hildwein et al. |
| 5,562,702 A | 10/1996 | Huitema et al. |
| 5,569,274 A | 10/1996 | Rapacki et al. |
| 5,571,116 A | 11/1996 | Bolanos et al. |
| 5,573,543 A | 11/1996 | Akopov et al. |
| 5,575,799 A | 11/1996 | Bolanos et al. |
| 5,578,052 A | 11/1996 | Koros et al. |
| 5,580,067 A | 12/1996 | Hamblin et al. |
| 5,582,611 A | 12/1996 | Tsukagoshi et al. |
| 5,584,425 A | 12/1996 | Savage et al. |
| 5,588,579 A | 12/1996 | Schnut et al. |
| 5,591,186 A | 1/1997 | Wurster et al. |
| 5,597,107 A | 1/1997 | Knobel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,381 A | 3/1997 | Thom et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,665,100 A | 9/1997 | Yoon |
| 5,667,473 A | 9/1997 | Finn et al. |
| 5,667,478 A | 9/1997 | McFarlin et al. |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,697,542 A | 12/1997 | Knodel et al. |
| 5,709,335 A | 1/1998 | Heck |
| 5,732,871 A | 3/1998 | Clark et al. |
| 5,732,872 A | 3/1998 | Bolduc et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,458 A | 6/1998 | Wang et al. |
| 5,776,147 A | 7/1998 | Dolendo |
| 5,779,130 A | 7/1998 | Alesi et al. |
| 5,779,132 A | 7/1998 | Knodel et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,820,009 A | 10/1998 | Melling et al. |
| 5,823,956 A | 10/1998 | Roth et al. |
| 5,826,776 A | 10/1998 | Schulze et al. |
| 5,829,662 A | 11/1998 | Allen et al. |
| 5,836,503 A | 11/1998 | Ehrenfels et al. |
| 5,846,221 A | 12/1998 | Snoke et al. |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,893,553 A | 4/1999 | Pinkous |
| 5,893,875 A | 4/1999 | O'Connor et al. |
| 5,895,084 A | 4/1999 | Mauro |
| 5,897,562 A | 4/1999 | Bolanos et al. |
| 5,901,895 A | 5/1999 | Heaton et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,954,731 A | 9/1999 | Yoon |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,989,274 A | 11/1999 | Davison et al. |
| 5,993,378 A | 11/1999 | Lemelson |
| 5,993,454 A | 11/1999 | Longo |
| 5,993,466 A * | 11/1999 | Yoon ............................ 606/147 |

| | | | |
|---|---|---|---|
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,162,220 A | 12/2000 | Nezhat |
| 6,165,191 A | 12/2000 | Shibata et al. |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,241,139 B1 | 6/2001 | Milliman et al. |
| 6,244,809 B1 | 6/2001 | Wang et al. |
| 6,246,200 B1 | 6/2001 | Blumenkranz et al. |
| D444,555 S | 7/2001 | Cooper et al. |
| 6,264,087 B1 | 7/2001 | Whitman |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,786,382 B1 | 9/2004 | Hoffman |
| 6,790,217 B2 | 9/2004 | Schulze et al. |
| 6,964,363 B2 | 11/2005 | Wales et al. |
| 7,241,288 B2 | 7/2007 | Braun |
| 7,404,509 B2 | 7/2008 | Ortiz et al. |
| 2001/0016750 A1 | 8/2001 | Malecki et al. |
| 2001/0031975 A1 | 10/2001 | Whitman et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0072736 A1 | 6/2002 | Tierney et al. |
| 2002/0165444 A1 | 11/2002 | Whitman |
| 2002/0198554 A1 | 12/2002 | Whitman et al. |
| 2003/0105478 A1 | 6/2003 | Whitman et al. |
| 2003/0130677 A1 | 7/2003 | Whitman et al. |
| 2003/0176794 A1 | 9/2003 | Whitman et al. |
| 2004/0094597 A1* | 5/2004 | Whitman et al. ......... 227/180.1 |
| 2006/0025817 A1 | 2/2006 | Ortiz et al. |
| 2006/0049229 A1 | 3/2006 | Milliman et al. |
| 2007/0023476 A1* | 2/2007 | Whitman et al. ......... 227/175.1 |
| 2007/0023477 A1 | 2/2007 | Whitman et al. |
| 2009/0101692 A1 | 4/2009 | Whitman et al. |
| 2010/0042143 A1 | 2/2010 | Cunningham |

FOREIGN PATENT DOCUMENTS

| | | |
|---|---|---|
| DE | 43 12 147 | 10/1993 |
| EP | 0 041 022 | 12/1981 |
| EP | 0 121 474 | 10/1984 |
| EP | 0 142 225 | 5/1985 |
| EP | 0 156 774 | 10/1985 |
| EP | 0 203 375 | 12/1986 |
| EP | 0 216 532 | 4/1987 |
| EP | 0 293 123 | 1/1988 |
| EP | 0 324 166 | 7/1989 |
| EP | 0 324 637 | 7/1989 |
| EP | 0 365 153 | 4/1990 |
| EP | 0 369 324 | 5/1990 |
| EP | 0 373 762 | 6/1990 |
| EP | 0 484 677 | 7/1990 |
| EP | 0 399 701 | 11/1990 |
| EP | 0 514 139 | 11/1992 |
| EP | 0 536 903 | 4/1993 |
| EP | 0 639 762 | 5/1993 |
| EP | 0 552 050 | 7/1993 |
| EP | 0 116 220 | 10/1993 |
| EP | 0 593 920 | 4/1994 |
| EP | 0 598 579 | 5/1994 |
| EP | 0 621 006 | 10/1994 |
| EP | 0 630 612 | 12/1994 |
| EP | 0 634 144 | 1/1995 |
| EP | 0 639 349 | 2/1995 |
| EP | 0 679 367 | 11/1995 |
| EP | 0 705 571 | 4/1996 |
| EP | 0 552 423 | 1/1998 |
| EP | 0 878 169 | 11/1998 |
| EP | 0 947 167 | 10/1999 |
| EP | 0 653 922 | 12/1999 |
| EP | 0 581 400 | 5/2000 |
| FR | 2 660 851 | 10/1991 |
| GB | 1 082 821 | 9/1967 |
| GB | 1 352 554 | 5/1974 |
| GB | 1 452 185 | 10/1976 |
| GB | 2 044 108 | 10/1980 |
| GB | 2 048 685 | 12/1980 |
| GB | 2 165 559 | 4/1986 |
| GB | 2 180 455 | 4/1987 |
| NL | 77 11 347 | 4/1979 |
| SU | 659146 | 4/1979 |
| WO | WO 82/03545 | 10/1982 |
| WO | WO 83/00992 | 3/1983 |
| WO | WO 90/05489 | 5/1990 |
| WO | WO 90/05491 | 5/1990 |
| WO | WO 90/06085 | 6/1990 |
| WO | WO 91/07136 | 5/1991 |
| WO | WO 92/16141 | 10/1992 |
| WO | WO 93/08754 | 5/1993 |
| WO | WO 93/14706 | 8/1993 |
| WO | WO 95/18572 | 7/1995 |
| WO | WO 95/35065 | 12/1995 |
| WO | WO 97/12555 | 4/1997 |
| WO | WO 98/14129 | 4/1998 |
| WO | WO 99/20328 | 4/1999 |
| WO | WO 00/72765 | 11/1999 |
| WO | WO 99/58076 | 11/1999 |
| WO | WO 01/03587 | 1/2001 |
| WO | WO 01/08572 | 2/2001 |
| WO | WO 01/17448 | 3/2001 |
| WO | WO 01/35813 | 5/2001 |
| WO | WO 01/62163 | 8/2001 |
| WO | WO 02/058539 | 8/2002 |
| WO | WO 03/077769 | 9/2003 |

OTHER PUBLICATIONS

PCT Search Report for corresponding PCT/US08/77255 mailing is Nov. 28, 2008 (1 page).

* cited by examiner

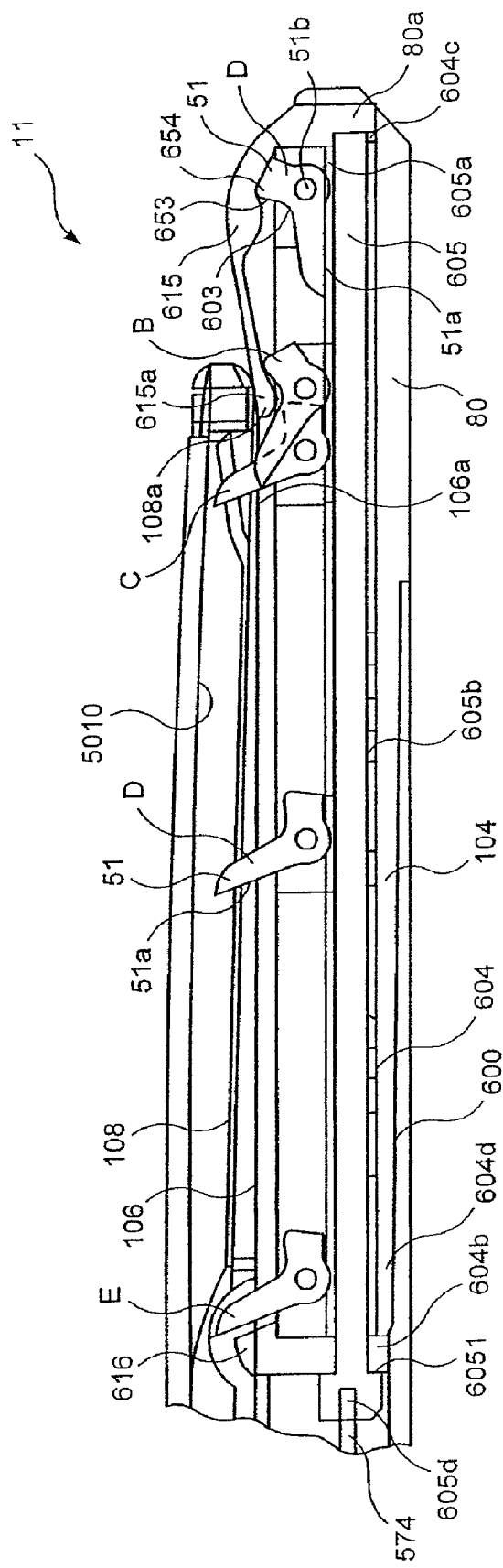
F I G. 3g

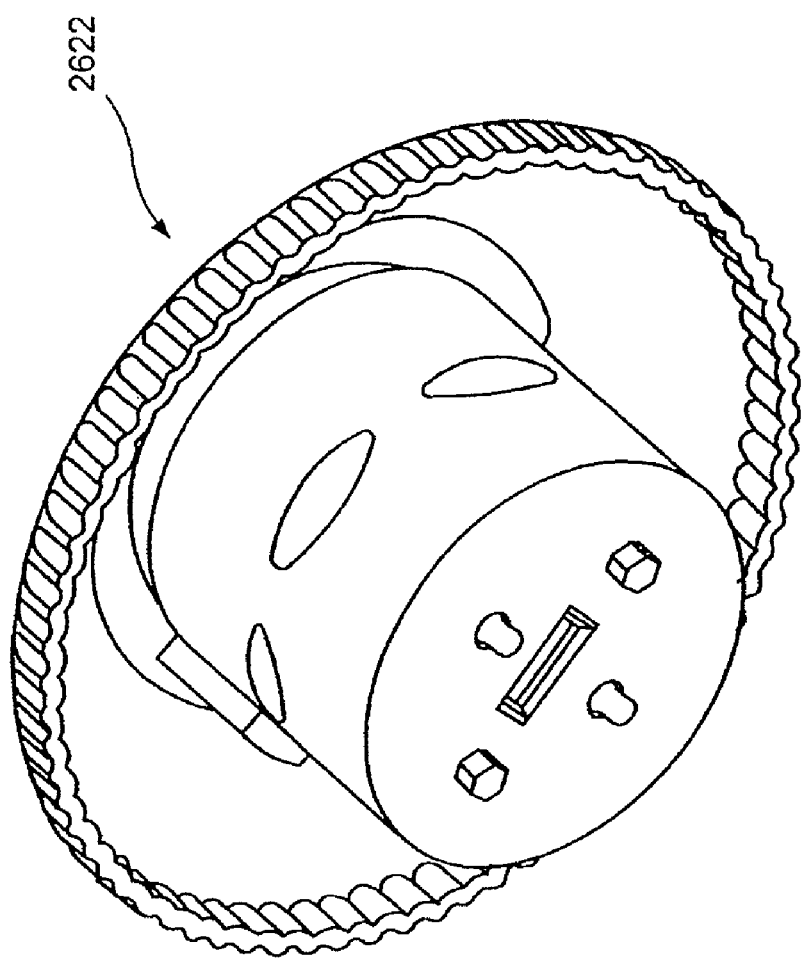

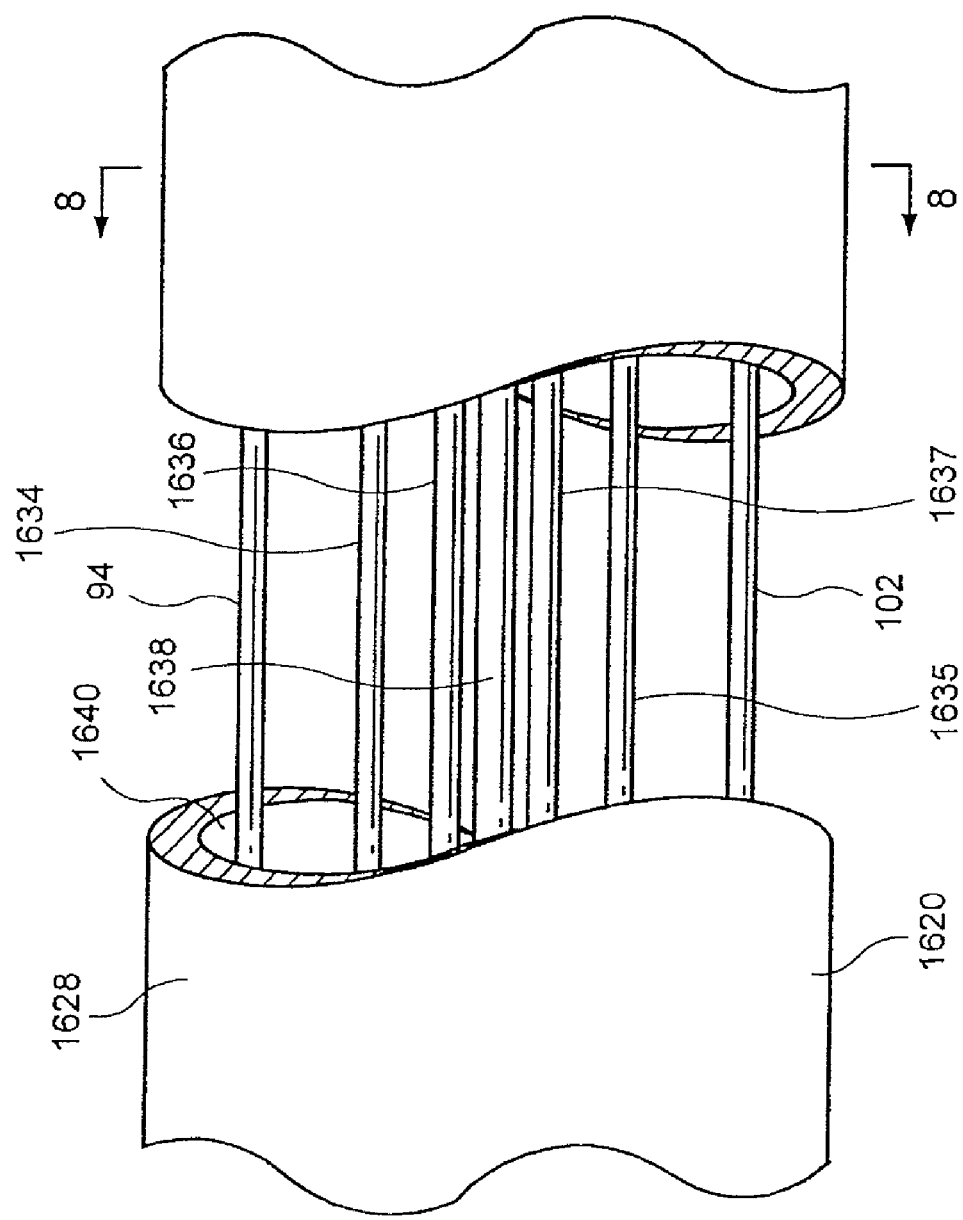

SURGICAL DEVICE HAVING A ROTATABLE JAW PORTION

CROSS-REFERENCE TO RELATED APPLICATIONS

The present application is a continuation application of U.S. Ser. No. 13/027,292, filed on Feb. 15, 2011 (now U.S. Pat. No. 7,992,758), which is a continuation application of U.S. Ser. No. 12/235,386 (now U.S. Pat. No. 7,918,230), filed Sep. 22, 2008, which claims the benefit of and priority to U.S. Provisional Application Ser. No. 60/974,291, filed on Sep. 21, 2007, which are expressly incorporated herein in their entirety by reference thereto.

INCORPORATION BY REFERENCE

The present application expressly incorporates herein by reference each of the following in its entirety: U.S. patent application Ser. No. 11/191,851, filed on Jul. 27, 2005; U.S. patent application Ser. No. 60/388,644, filed on Jun. 14, 2002; U.S. patent application Ser. No. 10/460,291, filed on Jun. 11, 2003; U.S. patent application Ser. No. 09/999,546, filed on Nov. 30, 2001; U.S. patent application Ser. No. 09/887,789, filed on Jun. 22, 2001; U.S. patent application Ser. No. 09/836,781, filed on Apr. 17, 2001; U.S. patent application Ser. No. 09/723,715, filed on Nov. 28, 2000; U.S. patent application Ser. No. 09/324,451, filed on Jun. 2, 1999, and issued as U.S. Pat. No. 6,315,184 on Nov. 13, 2001; U.S. patent application Ser. No. 09/324,452, filed on Jun. 2, 1999, and issued as U.S. Pat. No. 6,443,973 on Sep. 3, 2002; U.S. patent application Ser. No. 09/351,534, filed on Jul. 12, 1999 and issued as U.S. Pat. No. 6,264,087 on Jul. 24, 2001; U.S. patent application Ser. No. 09/510,923, filed on Feb. 22, 2000 and issued as U.S. Pat. No. 6,517,565 on Feb. 11, 2003; and U.S. patent application Ser. No. 09/510,927, filed on Feb. 22, 2000 and issued as U.S. Pat. No. 6,716,233 on Apr. 6, 2004.

FIELD OF THE INVENTION

The present invention relates to a surgical device. More specifically, the present invention relates to a powered, articulating device for clamping, cutting and stapling tissue.

BACKGROUND INFORMATION

One type of surgical device is a linear clamping, cutting and stapling device. Such a device may be employed in a surgical procedure to resect a cancerous or anomalous tissue from a gastro-intestinal tract. One conventional linear clamping, cutting and stapling instrument is shown in FIG. 1. The device includes a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

One problem with the foregoing surgical devices, and in particular with the foregoing linear clamping, cutting and stapling devices such as that illustrated in FIG. 1, is that the opposing jaws may be difficult to maneuver within a patient. It may be necessary for a surgeon to move the opposing jaws between various angles in order to position the desired tissue between the opposing jaws. However, it is also generally desirable to make an incision in a patient that is as small as possible, and the small size of an incision limits the degree to which the opposing jaws may be maneuvered.

Another problem with the foregoing surgical devices, and in particular with the foregoing linear clamping, cutting and stapling devices such as that illustrated in FIG. 1, is that the opposing jaws may not be sufficiently hemostatic. Specifically, the opposing jaws of the foregoing surgical devices are not clamped together with sufficient force, thereby reducing the effectiveness of the surgical device.

Thus, there is believed to be a need for an improvement in the maneuverability of clamping, cutting and stapling devices. In addition, there is believed to be a need for a clamping, cutting and stapling device that provides additional clamping force.

SUMMARY

In accordance with an example embodiment of the present invention, a surgical device is provided that includes a jaw portion pivotably connected to a shaft portion about a hinge. The hinge defines an axis of rotation of these components that is perpendicular to one or both of the jaw portion and the shaft portion. The jaw portion, or a part thereof, may also be rotatable relative to the shaft portion about the longitudinal axis of the jaw portion.

The jaw portion includes a first jaw and a second jaw. The second jaw is disposed in opposed correspondence with the first jaw. The first jaw may be pivotably coupled to the second jaw. The device may also include at least one of a cutting element and a stapling element disposed within the second jaw, preferably a blade rotatably mounted on a staple-driving wedge. The cutting element and/or the stapling element may be configured to move between a distal end and a proximal end of the second jaw to at least one of cut and staple a section of tissue disposed between the first and second jaws.

In accordance with an example embodiment of the present invention, a surgical device is provided that includes a jaw portion. The jaw portion includes a first jaw and a second jaw moveable relative to the first jaw. The surgical device also includes a shaft portion coupled to a proximal end of the jaw portion. The surgical device further includes a driver configured to cause relative movement of the jaw portion and the shaft portion. The jaw portion defines a first longitudinal axis and the shaft portion defines a second longitudinal axis. The driver may be configured to cause the jaw portion to pivot relative to the shaft portion about a pivot axis that is perpendicular to the first and second longitudinal axes. The first and second jaws may be moveable relative to each other in a plane, the pivot axis being arranged parallel to the plane. Also, in accordance with an example embodiment of the present invention, the driver is also configured to cause at least a portion of the jaw portion to pivot relative to the shaft portion about the first longitudinal axis.

The driver may be adapted to be driven by a first rotatable drive shaft and a second rotatable drive shaft. For instance, the driver may be configured such that rotation of the first and second rotatable drive shafts in opposite directions relative to each other causes the jaw portion to pivot relative to the shaft portion about the pivot axis. Also, the driver may be configured such that rotation of the first and second rotatable drive shafts in a same direction relative to each other causes the at least a portion of the jaw portion to rotate relative to the shaft portion about the first longitudinal axis. Furthermore, the driver may be configured such that rotation of the first rotatable drive shaft without rotating the second rotatable drive shaft causes relative movement of the first jaw and the second jaw.

The surgical device may include a surgical member disposed within the first jaw. The surgical member may include a cutting element and/or a stapling element. The driver may be configured such that rotation of the second rotatable drive shaft without rotating the first rotatable drive shaft causes relative movement of the surgical member within the first jaw.

In accordance with an example embodiment of the present invention, there is provided a surgical device that includes a jaw portion including a first jaw and a second jaw moveable relative to the first jaw, a shaft portion coupled to a proximal end of the jaw portion, and a driver adapted to be driven by first and second rotatable drive shafts such that selective rotation of the first and second rotatable drive shafts causes the surgical device to perform at least four different functions, e.g., movement of a first one of the jaw portion, the first jaw, the second jaw and the shaft portion relative to at least a second one of the jaw portion, the first jaw, the second jaw and the shaft portion.

The jaw portion may define a first longitudinal axis, the first of the at least four different functions including the rotation of at least a portion of the jaw portion relative to the shaft portion about the first longitudinal axis. The driver is configured to be driven by rotation of the first and second rotatable drive shafts in a same direction relative to each other so as to cause the at least a portion of the jaw portion to rotate relative to the shaft portion about the first longitudinal axis. The shaft portion may define a second longitudinal axis, a second of the at least four different functions including pivoting the jaw portion relative to the shaft portion about a pivot axis that is perpendicular to the second longitudinal axis. The driver is configured to be driven by rotation of the first and second rotatable drive shafts in opposite directions relative to each other so as to cause the jaw portion to pivot relative to the shaft portion about the pivot axis. A third of the at least four different functions may include moving the first jaw relative to the second jaw. The driver is configured to be driven by the first rotatable drive shaft without rotation of the second rotatable drive shaft to cause relative movement of the first jaw and the second jaw. In addition, the surgical device may also include a surgical member, e.g., a cutting and/or stapling element, disposed within the first jaw, a fourth of the at least four different functions including relative movement of the surgical member within the first jaw. The driver is configured to be driven by rotation of the second rotatable drive shaft without rotation of the first rotatable drive shaft so as to cause relative movement of the surgical member within the first jaw.

In accordance with an example embodiment of the present invention, there is provided a surgical device that includes a jaw portion, having a first jaw in opposed correspondence with a second jaw, the second jaw including a surgical member; a shaft portion coupled to a proximal end of the jaw portion; at least one motor configured to rotate the jaw portion relative to the shaft portion, to move the jaw portion relative to the shaft portion, move the first jaw relative to the second jaw and move the surgical member within the second jaw. The surgical member may be prevented from moving within the second jaw unless the first jaw is in a closed position relative to the second jaw.

When the first jaw is in an open position relative to the second jaw, the jaw portion may be rotatable relative to the shaft portion. The surgical device may also include a gear element, and the gear element may be selectively engaged based upon a position of the first jaw relative to the second jaw. The gear element may be an idler gear that is moveable between a proximal position and a distal position. The surgical device may also include a cam block that is moveable between a proximal position and a distal position. The cam block may include a surface, and the cam block may be moved between its proximal and distal positions by engagement of the surface with a surface of one of the first and second jaws when the first and second jaws are moved relative to each other. The idler gear may be moved between its proximal and distal positions by engagement of the cam block with the idler gear.

When the idler gear is in a distal position, the idler gear may engage recesses of a housing, and rotation of the idler gear by a drive element may cause the jaw portion to rotate relative to the shaft portion. When the idler gear is in a proximal position, the idler gear may be out of engagement with the recesses of the housing, such that the idler gear is rotatable relative to the housing, and rotation of the idler gear by the drive element may cause the surgical member to move within the second jaw. Advantageously, the surgical member may include a cutting element and/or a stapling element.

In accordance with an example embodiment of the present invention, there is provided a method of using a surgical device, the surgical device including a jaw portion that has a first jaw in opposed correspondence with a second jaw, the second jaw including a surgical member, and a shaft portion coupled to a proximal end of the jaw portion. The method may include the steps of: operating at least one motor so as to selectively rotate the jaw portion relative to the shaft portion, move the jaw portion relative to the shaft portion, move the first jaw relative to the second jaw, and move the surgical member within the second jaw; and locking the surgical member from moving within the second jaw unless the first jaw is in a closed position relative to the second jaw.

The method may also include the step of rotating the jaw portion relative to the shaft portion when the first jaw is in an open position relative to the second jaw. In addition, a gear element may be provided. The method may include the step of selectively engaging the gear element based upon a position of the first jaw relative to the second jaw. Providing the gear element may include providing an idler gear that is moveable between a proximal position and a distal position. A cam block may be provided that is moveable between a proximal position and a distal position.

The cam block may include a surface, and the method may include the step of moving the cam block between its proximal and distal positions by engagement of the surface with a surface of one of the first and second jaws when the first and second jaws are moved relative to each other. The idler gear may be moved between its proximal and distal positions by engagement of the cam block with the idler gear. The idler gear may engage recesses of a housing when the idler gear is in a distal position. When the idler gear engages the recesses of the housing, rotation of the idler gear by a drive element may cause the jaw portion to rotate relative to the shaft portion.

The method may also include the steps of moving the idler gear to a proximal position such that the idler gear is out of engagement with the recesses of the housing and rotating the idler gear relative to the housing. Upon rotating the idler gear by the drive element, the surgical member may be moved within the second jaw. Advantageously, the surgical member includes at least one of a cutting element and a stapling element, and the step of moving the surgical member includes at least one of cutting and stapling a section of tissue.

BRIEF DESCRIPTION OF THE DRAWINGS

FIG. 3(g) is a cross-sectional view of the surgical device, according to one embodiment of the present invention, in a fully closed position;

FIGS. 3(i) to 3(l) are side cross-sectional views that illustrate the opening and closing of first and second jaws, according to another example embodiment of the present invention;

FIG. 6(b) illustrates a rear perspective view of the first coupling, according to an example embodiment of the present invention;

FIG. 7 illustrates a side view, partially in section, of the flexible shaft, according to another example embodiment of the present invention;

DETAILED DESCRIPTION

Figure 2A:
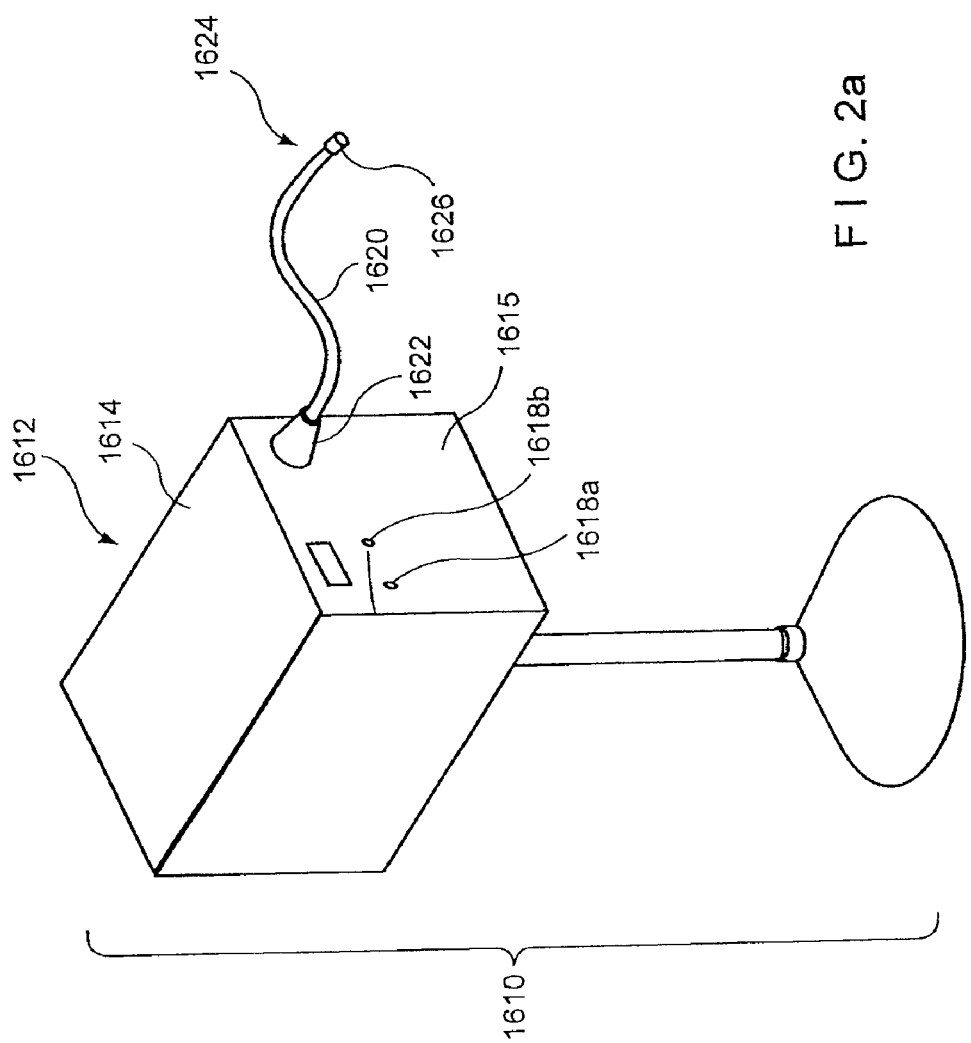
FIG. 2(a) is a perspective view of an example embodiment of an electro-mechanical driver component, according to the present invention.
Figure 2B:
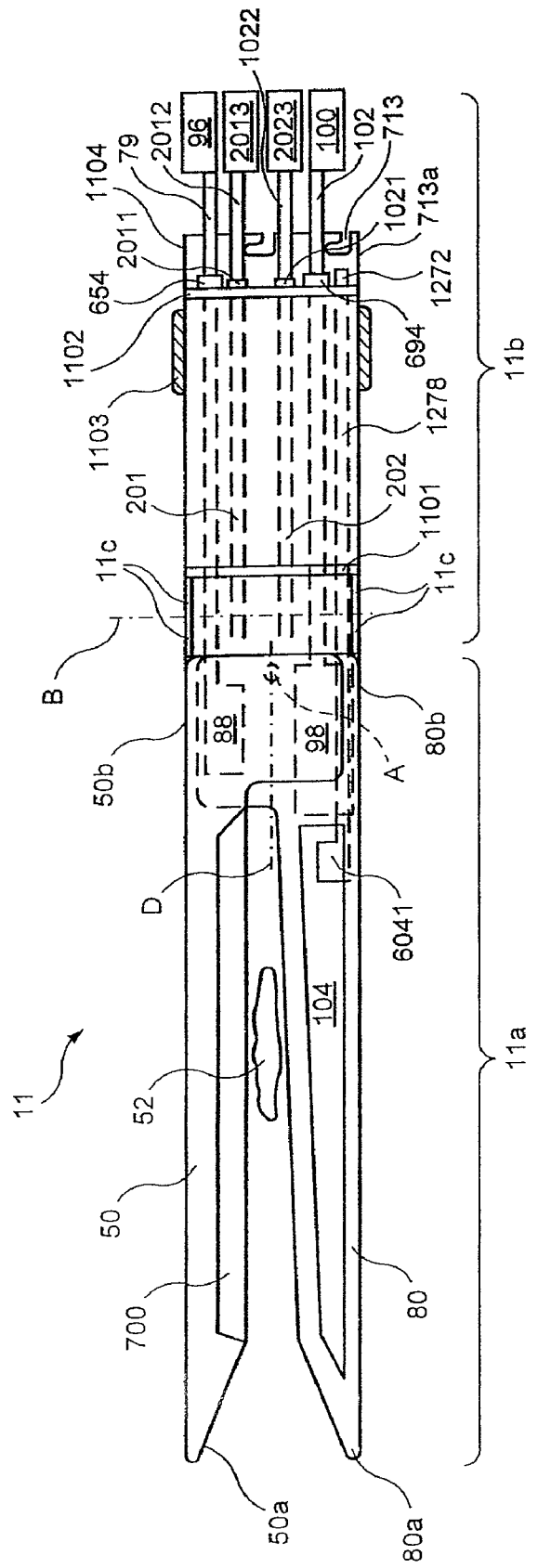
FIG. 2(b) is a schematic diagram that illustrates some of the components of a surgical device, according to an example embodiment of the present invention.

FIG. 2(b) is a schematic diagram that illustrates some of the components of a surgical device 11, according to an example embodiment of the present invention. The surgical device 11 is configured so as to be particularly well-suited for insertion into the body of a patient, e.g., via a cannula (not shown). In the embodiment shown, the surgical device 11 is a clamping, cutting and stapling device. The surgical device 11 includes a jaw portion 11a that is pivotably coupled to a shaft portion 11b by a hinge portion 11c. The jaw portion 11a includes a first jaw 50 having a distal end 50a and a proximal end 50b, and a second jaw 80 having a distal end 80a and a proximal end 80b. The first jaw 50 and the second jaw 80 are pivotably coupled relative to each other at or near their respective proximal ends 50b, 80b. In the example embodiment shown, the first jaw 50 and the second jaw 80 pivot relative to each other about pivot axis A, which is oriented perpendicular to the page.

As mentioned above, the jaw portion 11a is pivotably coupled to the shaft portion 11b by the hinge portion 11c. Specifically, the jaw portion 11a is pivotable relative to the shaft portion 11b about a pivot axis B, which may be positioned at any location on or between the jaw portion 11a and the shaft portion 11b, and at any circumferential location relative to the jaw portion 11a and the shaft portion 11b. In the example embodiment shown, the pivot axis B is oriented vertically in the view shown, such that, upon articulation, the jaw portion 11a pivots within a plane that is perpendicular to the page. It should be recognized that, in other example embodiments, the pivot axis B may have a different orientation, so as to enable the jaw portion 11a to pivot within a different plane. The jaw portion 11a may be pivotable to and between any angles relative to the shaft portion 11b, such that the jaw portion 11a can be selectively positioned as desired during use. Multiple pivot axes relative to the longitudinal axis of the shaft portion 11b (the longitudinal axis of the shaft portion 11b is designated as axis D in FIG. 2(b)) may be provided. For instance, in various embodiments, the jaw portion 11a may be rotatable relative to the shaft portion 11b about its longitudinal axis D, or may be rotatable relative to the shaft portion 11b about multiple pivot axes that are perpendicular to the longitudinal axis D.

The shaft portion 11b may include a distal portion 1101, to which the jaw portion 11a is connected, and a proximal portion 1102. The proximal portion 1102 of the shaft portion 11b may include a handle 1103, with which a user may grasp the surgical device 11. At a proximal-most end of the proximal portion 1102, the shaft portion 11b may include a connection element 1104, e.g., a quick-connect coupling, for connecting to a flexible shaft (described in further detail below).

Figure 3A:
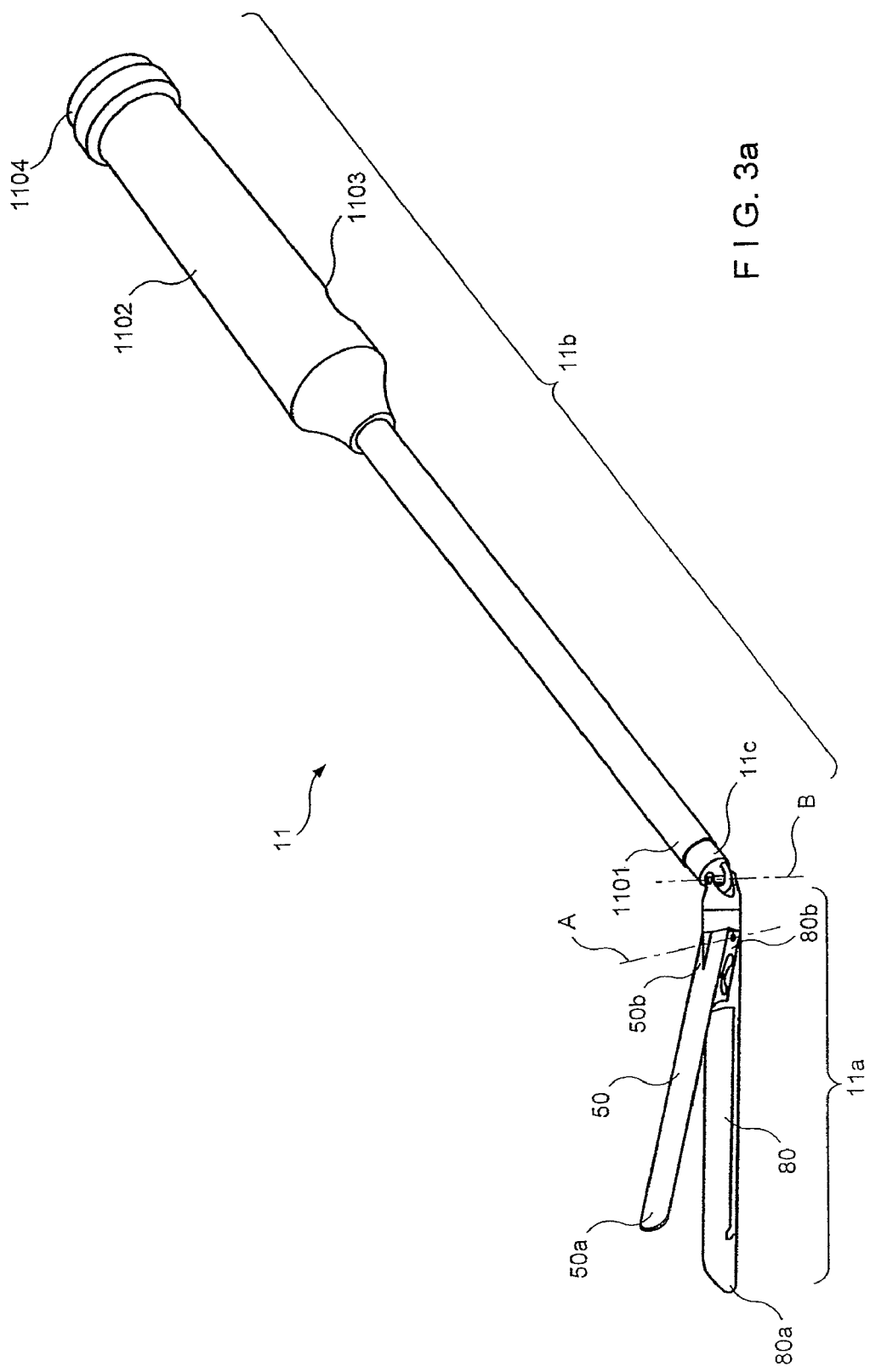
FIG. 3(a) is a perspective view of a surgical device, according to an example embodiment of the present invention.

The second jaw 80 includes a clamping surface 106. The second jaw 80 also includes a cutting and stapling element 104, which may form at least part of the clamping surface 106 of the second jaw 80. The first jaw 50 includes an anvil member 700 in opposed correspondence with the second jaw 80. The anvil member 700 includes the clamping surface 108, which, along with the clamping surface 106 of the second jaw 80, clamps a section of tissue to be cut and stapled. As explained in greater detail below, the cutting and stapling element 104 is configured to cut and staple a section of tissue when the first jaw 50 and the second jaw 80 are in a closed, e.g., fully closed, position. Additional features of the cutting and stapling element 104, according to an embodiment, are illustrated and described, for instance, in connection with FIGS. 3(f) and 3(g) below, and further in U.S. patent application Ser. No. 09/999,546, filed Nov. 30, 2001, and Ser. No. 10/460,291, filed Jun. 11, 2003, each of which, as set forth above, are hereby expressly incorporated herein by reference in its entirety.

Various drivers may be employed to drive the movements of the surgical device 11, e.g., pivoting the jaw portion 11a relative to the shaft portion 11b, rotating the jaw portion 11a or some part thereof around its longitudinal axis relative to the shaft portion 11b, pivoting the first jaw 50 relative to the second jaw 80, firing of a staple cartridge, etc. According to one embodiment of the present invention, these functions are performed by connection of the surgical device 11 to a flexible shaft having two rotatable drive shafts, although is should be recognized that in other embodiments, different types and/or a different number of drive components may be employed.

FIG. 2(b) illustrates schematically an embodiment wherein the surgical device 11 employs first and second drivers 88 and 98, each of which is connected to a respective one of two rotatable drive shafts of a, e.g., flexible, drive shaft. For instance, a first driver 88 may, e.g., operate to move the first jaw 50 and the second jaw 80 relative to each other. The first driver 88 may include any type of drive mechanism capable of moving the first jaw 50 and the second jaw 80 relative to each other. The first driver 88 may be situated at least partially in the proximal end 80b of the second jaw 80 and may be connected to the proximal end 50b of the first jaw 50. The first driver 88 may engage the proximal end 50b of the first jaw 50 so as to open and close the first jaw 50 relative to the second jaw 80. In addition, the first driver 88 may extend through the shaft portion 11b of the surgical device 11 to a first drive socket 654. The first drive socket 654 of the first driver 88 is coupled to a first motor 96 by a first drive shaft 94. As will be explained in more detail below, the first driver 88, when engaged by the first motor 96 via the first drive shaft 94, may operate to open and close first jaw 50 relative to second jaw 80, in addition to performing other operations of the surgical device 11.

The second jaw 80 also includes a second driver 98. The second driver 98 may also extend through the shaft portion 11b of the surgical device 11 to a second drive socket 694. The second drive socket 694 is coupled to a second motor 100 by a second drive shaft 102. The second driver 98, when engaged by the second motor 100 via the second drive shaft 102, may operate to drive the cutting and stapling element 104 to cut and staple a section of tissue 52, in addition to performing other operations of the surgical device 11.

While two drive sockets, e.g., the first drive socket 654 and the second drive socket 694, and two corresponding drive shafts, e.g., the first drive shaft 94 and the second drive shaft 102, are illustrated as being part of the surgical device 11 and as being for the purposes of clamping, cutting and stapling a section of tissue, it is possible to provide any suitable number of drive sockets and drive shafts. For example, a single drive shaft may be provided to perform the above-described functions of the surgical device 11.

In one embodiment, the two drive shafts, e.g., the first drive shaft 94 and the second drive shaft 102, are also configured to be employed to move the jaw portion 11a relative to the shaft portion 11b. An example of this type of embodiment is illustrated in, e.g., FIGS. 3(a) through 3(e), and is described further below. Alternatively, and as shown in FIG. 2(b), the surgical device 11 may also include a third driver 201 and a fourth driver 202 that are employed to move the jaw portion 11a relative to the shaft portion 11b. For instance, the third driver 201 may be configured to pivot the jaw portion 11a about axis B relative to the shaft portion 11b, while the fourth driver 202 may be configured to rotate the jaw portion 11a about its longitudinal axis D relative to the shaft portion 11b. In one embodiment, the third and fourth drivers 201, 202 are rotatable drive shafts that extend through the shaft portion 11b of the surgical device 11 to third and fourth drive sockets 2011, 2021, respectively. The third drive socket 2011 is coupled to a third motor 2013 by a third drive shaft 2012. The third driver 201, when engaged by the third motor 2013 via the third drive shaft 2012, operates to pivot the jaw portion 11a about axis B relative to the shaft portion 11b. The fourth drive socket 2021 is coupled to a fourth motor 2023 by a fourth drive shaft 2022. The fourth driver 202, when engaged by the fourth motor 2023 via the fourth drive shaft 2022, operates to rotate the jaw portion 11a about its longitudinal axis D relative to the shaft portion 11b.

The drive shafts, e.g., first and second rotatable drive shafts 94 and 102 and any other drive shafts, may be housed within a flexible drive shaft, such as the flexible drive shaft 1620 illustrated in FIG. 2(a). Other types of flexible drive shafts may also be employed. For instance, the drive shafts may be housed within a flexible drive shaft of the type described and illustrated in Applicant's co-pending Provisional Patent App. Designated as 60/703,227, which is expressly incorporated by reference herein in its entirety.

Referring to FIG. 2(b), the surgical device 11 may also include a memory module 6041. In one embodiment, the memory module 6041 is connected to or integral with the cutting and stapling element 104. The memory module 6041 is connected to a data connector 1272 by a data transfer cable 1278. Additional features of these components are set forth in connection with FIGS. 3(*f*) and 7.

Furthermore, FIG. 2(*b*) also illustrates a connection element 1104. The connection element 1104 may include a quick connect sleeve 713 that has quick connect slots 713*a* that engage complementary quick connect elements 1664 of a flexible drive shaft 1620, which is described in further detail below. In order to retain the quick connect elements 1664 of the flexible drive shaft 1620 in the quick connect slots 713*a* of the quick connect sleeve 713, the connection element 1104 may also include a spring.

According to an example embodiment of the present invention, the surgical device 11 may be configured as an attachment to, or may be integral with, an electro-mechanical surgical system, such as the electro-mechanical driver component 1610 having a motor system illustrated in FIG. 2(*a*). It should be appreciated that, in this example embodiment, any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors. In another example embodiment, the surgical device may be an attachment to, or may integral with, a mechanical driver system.

FIG. 3(*a*) is a perspective view of a surgical device 11, according to one embodiment of the present invention. As set forth above, FIGS. 3(*a*) to 3(*e*) illustrate one embodiment of the present invention in which two drive shafts are configured to be employed to move the jaw portion 11*a* relative to the shaft portion 11*b*, to rotate the jaw portion 11*a* about its longitudinal axis, to move the first jaw 50 relative to the second jaw 80, and to fire a stapling and cutting cartridge. In the position shown in FIG. 3(*a*), the jaw portion 11*a* is positioned at an angle of approximately 60 degrees relative to the shaft portion 11*b*. The jaw portion 11*a* may be appropriately positioned according to the incision made in the patient and to the position of the tissue desired to be clamped, cut and stapled.

FIG. 3(*b*) is a rear perspective view that illustrates some of the internal components of the surgical device 11, according to an example embodiment of the present invention. The outer body of the surgical device 11 is shown in ghost lines. As shown, the jaw portion 11*a* is in an initial position in which it is axially aligned with the shaft portion 11*b*.

FIG. 3(*b*) shows a first rotatable drive shaft 500, which may be axially rotatable within the shaft portion 11*b*. Coupled to the first rotatable drive shaft 500 is a gear element 502. The gear element 502 rotates about a longitudinal axis and is meshingly engaged with a gear element 504. The gear element 504 is held in position by pin 505, the central axis of which is coaxial with the pivot axis B around which the jaw portion 11*a* pivots relative to the shaft portion 11*b*.

The gear element 504 is also meshingly engaged with a gear element 506 within the jaw portion 11*a*. The gear element 506 is connected to a gear element 510 by a shaft 508. The gear element 506, the gear element 510, and the shaft 508 rotate within the jaw portion 11*a* about a longitudinal axis defined by the central axis of the shaft 508. The gear element 510 is meshingly engaged with a gear element 512 that rotates about a pin 513 that is longitudinally arranged within the jaw portion 11*a*. The gear element 512 is meshingly engaged with a gear element 514. The gear element 514 has a shaft portion that extends distally to a set of teeth 516. The teeth 516 are selectively engageable with a correspondingly-shaped opening in a plate 518, the plate 518 being keyed to an internal surface of the surgical device 11 so as to prevent relative rotation of the plate 518. The plate 518 is moveable in an axial direction between a first position, in which the correspondingly-shaped opening in the plate 518 is locked in engagement with the teeth 516, and a second position, in which the plate 518 is moved distally relative to the first position and the correspondingly-shaped opening in the plate 518 is not in engagement with the teeth 516.

Extending distally from the gear 514 and the shaft portion carrying the teeth 516 is a threaded screw 520. The threaded screw 520 is arranged longitudinally and is configured to rotate about a longitudinal axis when the gear 514 is rotated. Mounted on the threaded screw 520 is a push block 522. The push block 522 is keyed to an internal surface of the surgical device 11, so as to prevent relative rotation of the push block 520. Rotatably coupled to the lower distal end of the push block 520 is a pair of rollers 524. The pair of rollers 524 are seated within respective slots 5011 on each side of the upper jaw 50. The upper jaw 50 and the slots 5011 are shown in dotted line in FIG. 3(*b*).

FIG. 3(*b*) also shows a second rotatable drive shaft 550, which may be axially rotatable within the shaft portion 11*b*. Coupled to the second rotatable drive shaft 550 is a gear element 552. The gear element 552 rotates about a longitudinal axis and is meshingly engaged with a gear element 554. The gear element 554 is held in position by pin 505, the central axis of which is coaxial with the pivot axis B around which the jaw portion 11*a* pivots relative to the shaft portion 11*b*.

The gear element 554 is also meshingly engaged with a gear element 556 within the jaw portion 11*a*. The gear element 556 is connected to a gear element 560 by a shaft 558. The gear element 556, the gear element 560, and the shaft 558 rotate within the jaw portion 11*a* about a longitudinal axis defined by the central axis of the shaft 558. The gear element 560 is meshingly engaged with a gear element 562*a* that is mounted on a proximal end of the pin 513. The gear element 562*a* is configured to adapted to be non-rotatably mounted on, and thus to rotate with, the pin 513, the pin 513 extending longitudinally within the jaw portion 11*a*. In addition, a gear element 562*b* is adapted to be non-rotatably mounted on a distal end of the pin 513. Thus, the gear element 562*b* is also configured to rotate with the pin 513.

The gear element 562*b* has a shaft portion that extends distally and includes a set of teeth 5661 (hidden from view in FIG. 3(*b*) but shown in FIG. 3(*d*)). The teeth 5661 are selectively engageable with a correspondingly-shaped opening in the plate 518. As set forth above, the plate 518 is keyed to an internal surface of the surgical device 11 so as to prevent relative rotation of the plate 518, and is moveable in an axial direction between the first position, in which the correspondingly-shaped opening in the plate 518 is locked in engagement with the teeth 5661, and the second position, in which the plate 518 is moved distally relative to the first position and the correspondingly-shaped opening in the plate 518 is not in engagement with the teeth 5661.

The gear element 562*b* is meshingly engaged with a gear element 564. Extending distally from the gear 564 is a first longitudinal rod 566. The first longitudinal rod 566 is attached to a second longitudinal rod 568. The second longitudinal rod 568 has a shoulder 572. Between the first longitudinal rod 566 and the shoulder 572 of the second longitudinal rod 568 is a spring. The distal end 574 of the second longitudinal rod 568 is configured to engage a respective opening in a wedge driver 605. The wedge driver 605 rotates so as to drive a stapling/cutting wedge (described in further detail below) along a staple cartridge.

These components are also shown in various other views. For instance, FIG. 3(c) is a side perspective view that illustrates some of the internal components of the surgical device 11. As shown, the jaw portion 11a is pivoted, e.g., articulated, relative to the shaft portion 11b. In addition, FIG. 3(d) is a perspective view that illustrates the jaw portion 11a being further pivoted, e.g., articulated, relative to the shaft portion 11b. Also, FIG. 3(e) is a bottom perspective view that illustrates the jaw portion 11a being pivoted, e.g., articulated, relative to the shaft portion 11b.

As set forth above, the surgical device 11 may also include a cutting and stapling element 104. In one embodiment, the staple and cutting element 104 is a staple cartridge. FIG. 3(f) is an exploded view of a replaceable staple cartridge 600. The replaceable staple cartridge 600 is one type of stapling/cutting arrangement that may be employed as the cutting and stapling element 104 in the example embodiment of the present invention illustrated in FIGS. 3(a) to 3(e). The replaceable staple cartridge 600 includes a staple tray 604. The staple tray 604 has a slot 604i at its proximal end 604d in which the memory module 6041 is retained by a memory module retainer 6042. The memory module 6041 may store information as described, for example, in U.S. patent application Ser. No. 09/723,715, filed on Nov. 28, 2000, now issued as U.S. Pat. No. 6,793,652 on Sep. 21, 2004, U.S. patent application Ser. No. 09/836,781, filed on Apr. 17, 2001, U.S. patent application Ser. No. 09/887,789, filed on Jun. 22, 2001 and U.S. patent application Ser. No. 10/099,634, filed on Mar. 15, 2002, each of which is expressly incorporated herein by reference in its entirety. A wedge driver 605 is configured to be rotatably disposed through a central channel 604e of the staple tray 604. Specifically, the wedge driver 605 has a distal end 605a that is configured to be rotatably mounted within a distal orifice 604a of the staple tray 604. The wedge driver 605 also includes an externally threaded region 605b, a non-threaded portion 605c that rotatably extends through a proximal orifice 604b in the proximal end 604b of the staple tray 604, and a proximally-facing opening 605d at its proximal-most end for receiving the distal end 574 of the second longitudinal rod 568. The proximally-facing opening 605d and the distal end 574 of the second longitudinal rod 568 are adapted for non-rotatable coupling relative to each other when the distal end 574 of the second longitudinal rod 568 is received, e.g., inserted, within the proximally-facing opening 605d.

The replaceable staple cartridge 600 also includes a wedge 603 having an internally threaded bore 603a. The externally threaded region 605b of the wedge driver 605 is configured to extend through the internally threaded bore 603a of the wedge 603. The threads of the internally threaded bore 603a of the wedge 603 match the threads of the externally threaded region 605b of the wedge driver 605. As is discussed further below, upon rotation of the wedge driver 605, the wedge 603 is moved between the distal end 604c of the staple tray 604 and the proximal end 604d of the staple tray 604 through a central channel 604e.

The staple tray 604 also includes a plurality of vertically-disposed slots 604f in opposing walls 604g of the central channel 604e. On each side of the central channel 604e, a staple pusher 607 is configured to be slideably disposed within the slots 604f. More specifically, each of the staple pushers 607 has a top surface 607a running longitudinally between two rows 607b of staple pushing fingers 607c. The staple pushing fingers 607c are configured such that each staple pushing finger 607c in the row 607b that abuts the wall 604g of the staple tray 604 is retained within a corresponding slot 604f of the wall 604g so as to be vertically slideable therein. The staple pushing fingers 607c are positioned over slots 604h in the staple tray 604. The slots 604h in the staple tray 604 house a plurality of fasteners, e.g., staples 606. Each of the staples 606 includes a butt 606a and a pair of prongs 606b.

The wedge 603 also includes a pair of sloped edges 603b that slideably engage respective top surfaces 607a of the staple pushers 607. When the wedge 603 is moved from the distal end 604c to the proximal end 604d of the staple tray 604 through the central channel 604e, the pair of sloped edges 603b of the wedge 603 is configured to slideably engage the respective top surfaces 607a of the staple pushers 607 in order to successively push the staple pushing fingers 607c of the staple pushers 607 into, and thus the staples 606 out of, the slots 604h in the staple tray 604. A cartridge top 611 is configured to fit over the central channel 604a of the staple tray 604, while a staple retainer 610 is configured to cover the clamping surface 106 of the staple tray 604. Additional features, e.g., a blade 51, of the staple cartridge 600 are described below in connection with FIG. 3(g), these features being described during operation of the surgical device 11.

Figure 3B:
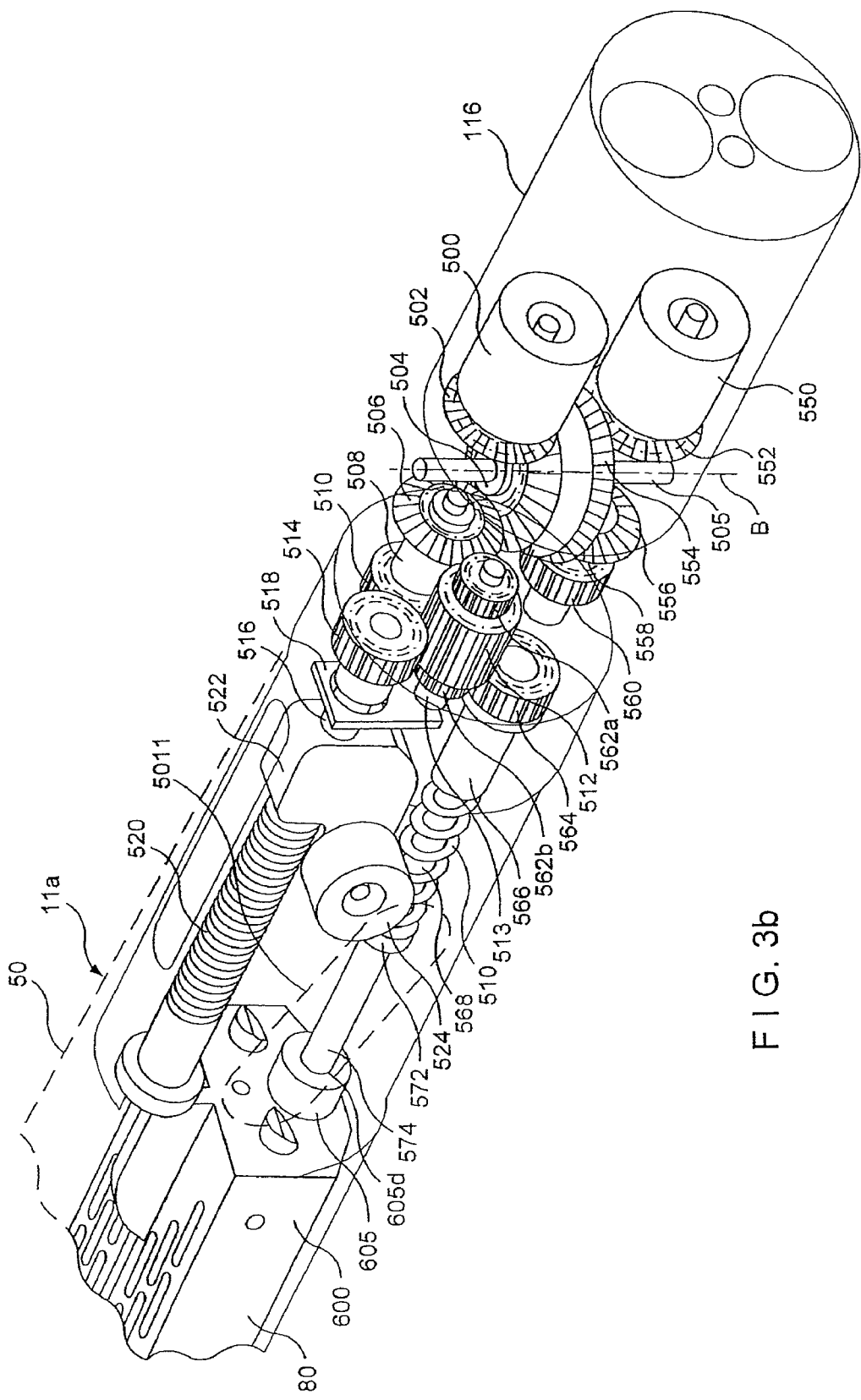
FIG. 3(b) is a rear perspective view that illustrates some of the internal components of the surgical device, according to one embodiment of the present invention.
Figure 3C:
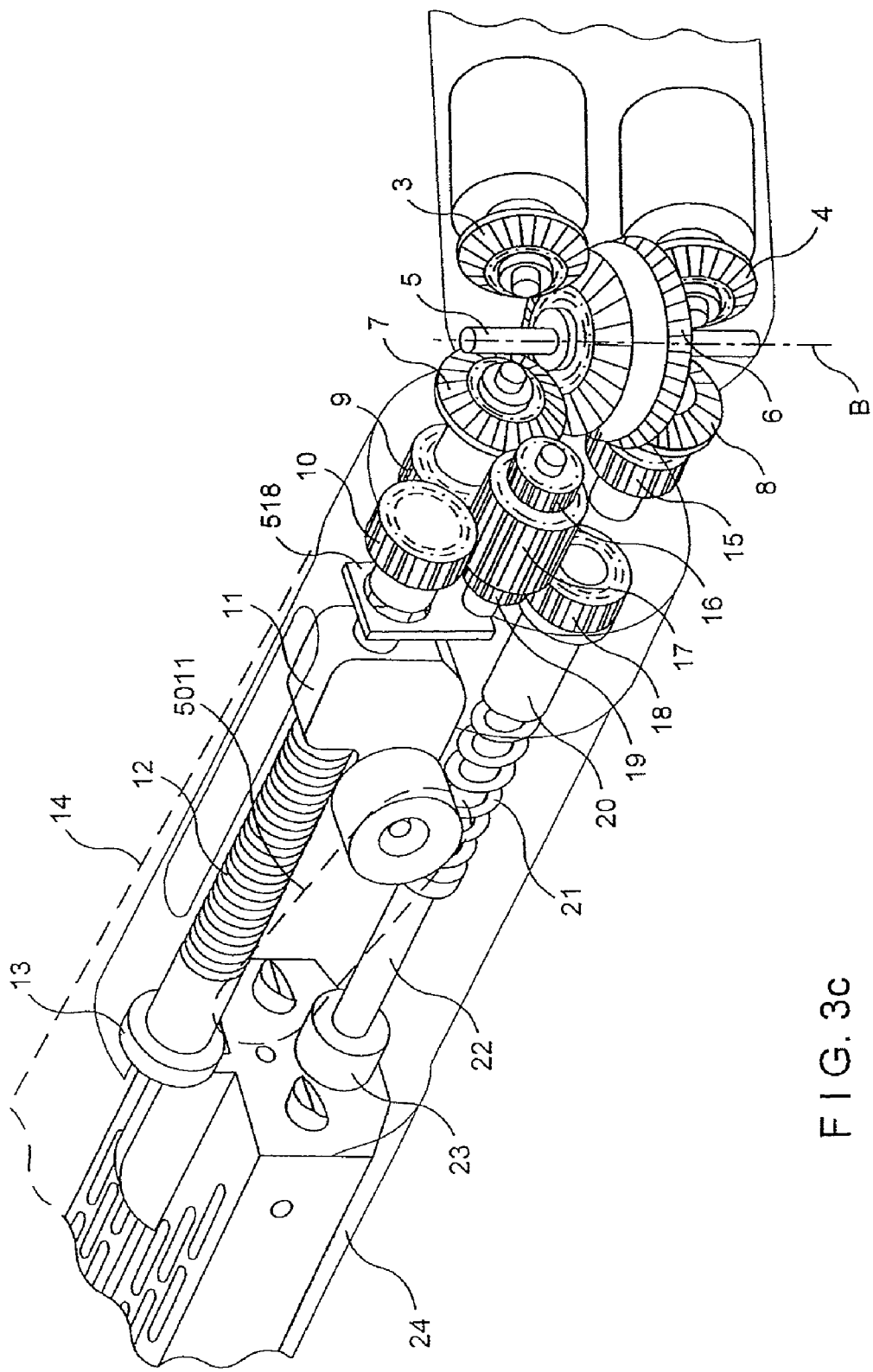
FIG. 3(c) is a side perspective view that illustrates some of the internal components of the surgical device, according to one embodiment of the present invention.
Figure 3D:
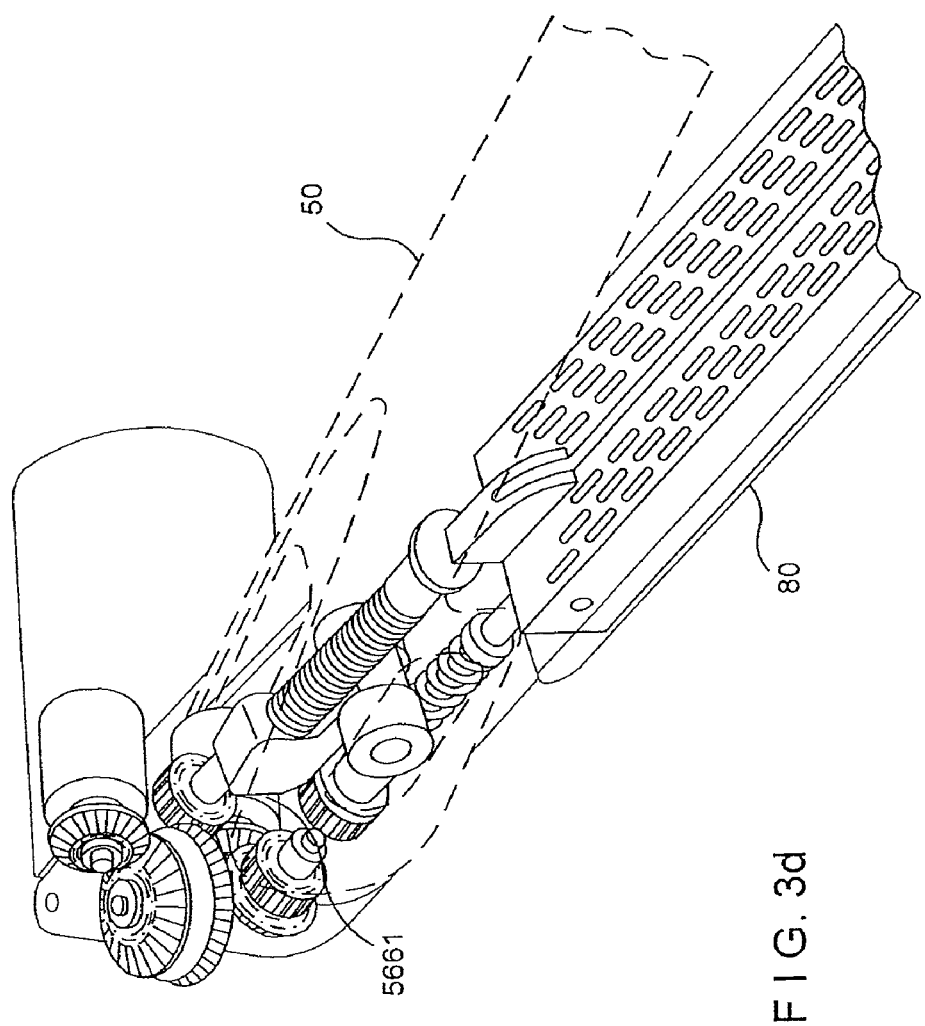
FIG. 3(d) is a perspective view that illustrates a jaw portion being fully pivoted, e.g., articulated, relative to a shaft portion, according to one embodiment of the present invention.
Figure 3E:
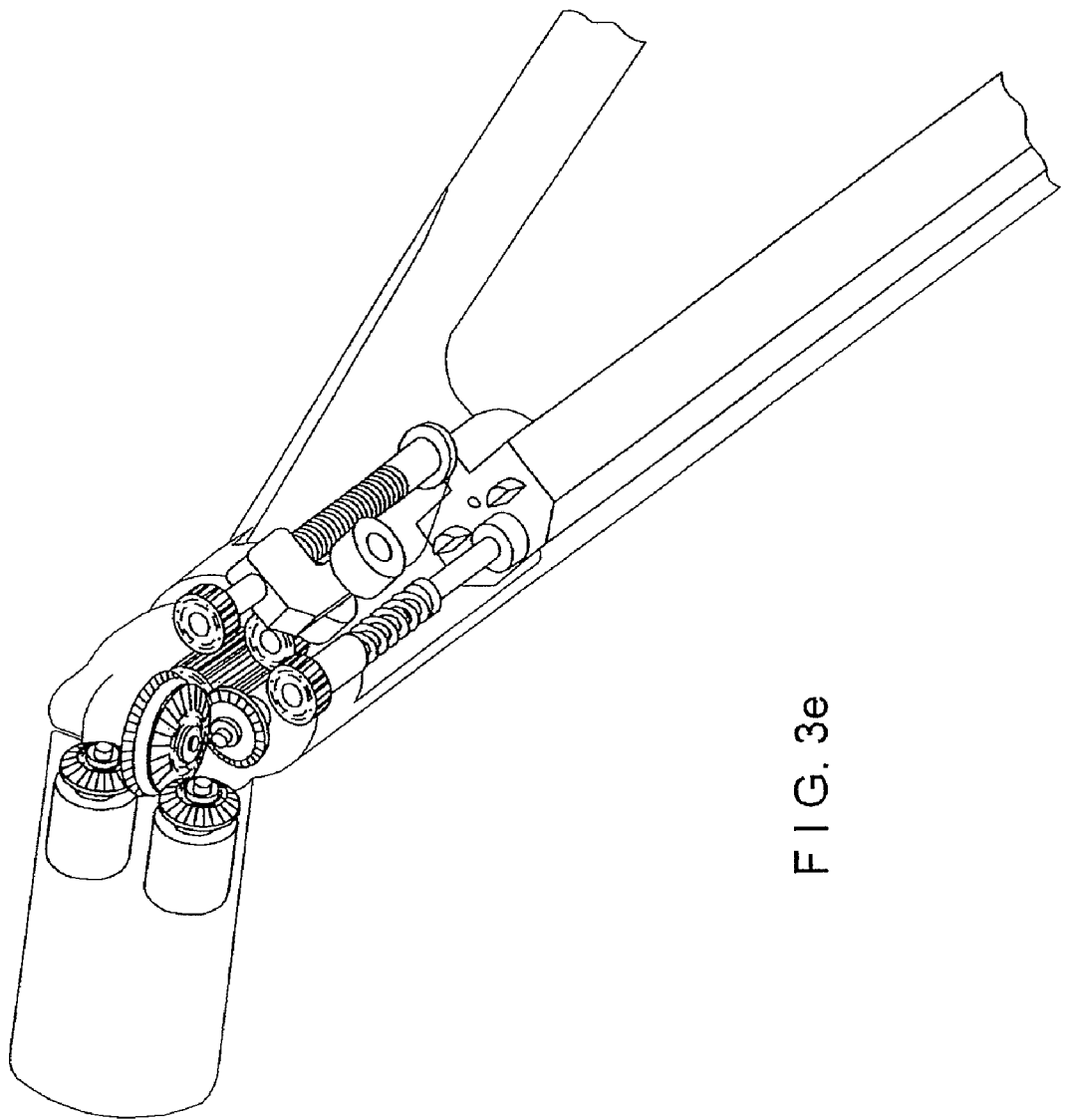
FIG. 3(e) is a bottom perspective view that illustrates the jaw portion being fully pivoted relative to the shaft portion, according to one embodiment of the present invention.
Figure 3F:
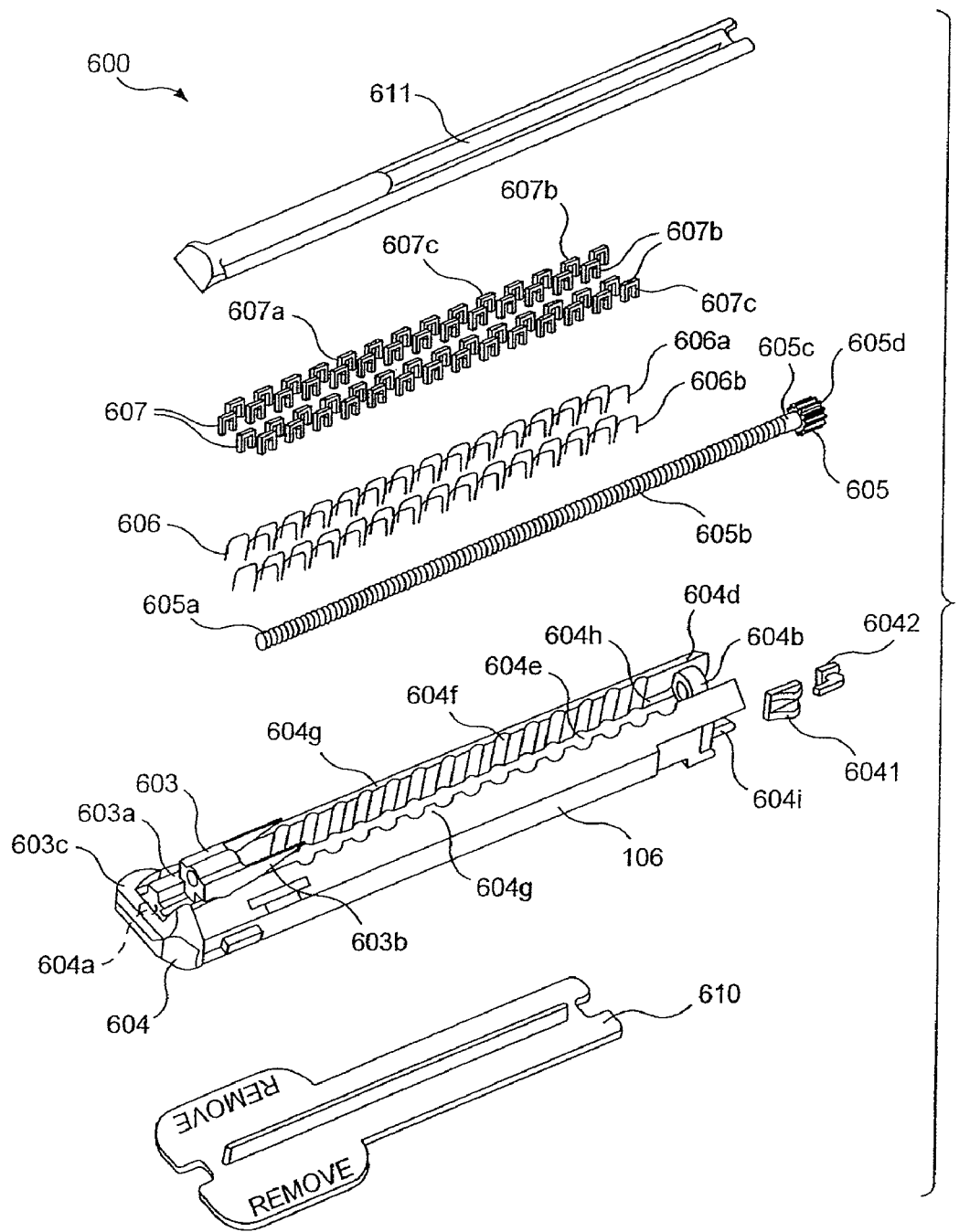
FIG. 3(f) is an exploded view of a replaceable staple cartridge, according to one embodiment of the present invention.
Figure 3H:
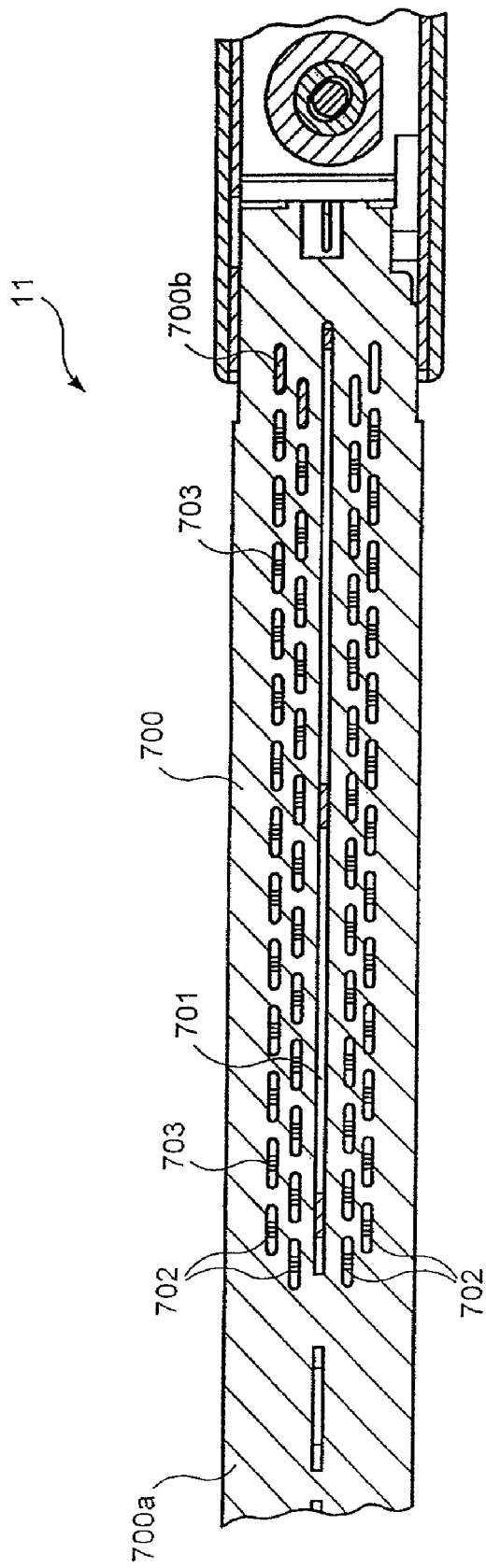
FIG. 3(h) is a bottom view of a first jaw, according to another example embodiment of the present invention.

FIG. 3(h) is a bottom view of the first jaw 50. The first jaw 50 includes an anvil member 700 having a longitudinally-disposed slot 701 that extends from a distal end to a proximal end of the anvil member 700. The slot 701 is aligned with the blade 51 of the second jaw 80 so that the blade 51 extends into and travels along the slot 701 when the blade is moved from the distal end 80a to the proximal end 80b of the second jaw 80. The anvil member 700 also includes a plurality of rows 702 of staple guides 703. The staple guides 703 are configured to receive the prongs 606b of the staples 606 and to bend the prongs 606b so as to close the staples 606. When the surgical device 11 is in the closed position, the rows 702 of the staple guides 703 align with the slots 604h of the staple tray 604 in the second jaw 80.

In operation, the jaw portion 11a is maintained in an initial position in which it is axially aligned with the shaft portion 11b, such as the position shown in FIG. 3(b). In this position, the surgical device 11 may be inserted, e.g., through a trocar, into a surgical site. Depending on the position of the incision and the tissue to be clamped, stapled and cut, the user may then articulate the jaw portion 11a relative to the shaft portion 11b.

In a first articulation process, the jaw portion 11a is pivoted relative to the shaft portion 11b. The plate 518 is arranged in its first position, e.g., such that the two openings in the plate 518 are locked in respective engagement with the teeth 516 of gear element 514 and with the teeth 5661 of the gear element 562b. The first rotatable drive shaft 500 and the second rotatable drive shaft 550 are then rotated in opposite directions. For instance, referring to FIG. 3(b), in order to articulate the jaw portion 11a in a clockwise direction relative to the shaft portion 11b (when viewed from above), the first rotatable drive shaft 500 may be rotated in a counter-clockwise direction (for the sake of simplicity, all references herein to a rotational direction, e.g., clockwise or counterclockwise, refer to a view from the proximal end of the surgical device towards the distal end of the surgical device 11, unless otherwise noted). The gear element 502 attached to the first rotatable drive shaft 500 is thus also caused to rotate in a counter-clockwise direction. By virtue of its engagement with the gear element 504, the counter-clockwise rotation of the gear element 502 causes the gear element 504 to rotate in a counter-clockwise direction (when viewed from above) about the pin 505. By virtue of its engagement with the gear element 506, the counter-clockwise rotation of the gear element 504 causes the gear element 506 to rotate in a clockwise direction.

Simultaneously, the second rotatable drive shaft 550 may be rotated in a clockwise direction. The gear element 552 attached to the second rotatable drive shaft 550 is thus also caused to rotate in a clockwise direction. By virtue of its engagement with the gear element 554, the clockwise rotation of the gear element 552 causes the gear element 554 to rotate in a counter-clockwise direction (when viewed from above) about the pin 505. By virtue of its engagement with the gear element 556, the clockwise rotation of the gear element 554 causes the gear element 556 to rotate in a counter-clockwise direction. The engagement of the plate 518 with the teeth 516 and 5661 prevents the rotation of the gear elements 506 and 566 relative to the surgical device 11. Thus, the jaw portion 11*a* is caused to rotate in a clockwise direction relative to the shaft portion 11*b* (when viewed from above). To rotate the jaw portion 11*a* in the opposite direction, e.g., counter-clockwise relative to the shaft portion 11*b* when viewed from above, the direction of rotation of the first and second rotatable drive shafts 500, 550 are reversed.

Once the jaw portion 11*a* is rotated about the pin 505 to a desired position, the jaw portion 11*a* may also be rotated, in a second articulation process, relative to the shaft portion 11*b* about the longitudinal axis of the jaw portion 11*a*, e.g., illustrated as axis D. The plate 518 is maintained in its first position, such that the two openings in the plate 518 are locked in respective engagement with the teeth 516 of gear element 514 and with the teeth 5661 of the gear element 562*b*. The first rotatable drive shaft 500 and the second rotatable drive shaft 550 are then rotated in the same direction. For instance, referring to FIG. 3(*b*), in order to rotate the jaw portion 11*a* about its longitudinal axis in a counter-clockwise direction relative to the shaft portion 11*b*, the first rotatable drive shaft 500 may be rotated in a counter-clockwise direction. The gear element 502 attached to the first rotatable drive shaft 500 is thus also caused to rotate in a counter-clockwise direction. By virtue of its engagement with the gear element 504, the counter-clockwise rotation of the gear element 502 causes the gear element 504 to rotate in a counter-clockwise direction (when viewed from above) about the pin 505. By virtue of its engagement with the gear element 506, the counter-clockwise rotation of the gear element 504 causes the gear element 506 to rotate in a clockwise direction. Since the gear element 506 is attached to the gear element 510 by the shaft 508, rotation of the gear element 506 in the clockwise direction causes the gear element 510 to also rotate in a clockwise direction. By virtue of its engagement with the gear element 512, the clockwise rotation of the gear element 510 causes the gear element 512 to rotate in a counter-clockwise direction.

The second rotatable drive shaft 550 may also be rotated in a counter-clockwise direction. The gear element 552 attached to the second rotatable drive shaft 550 is thus also caused to rotate in a counter-clockwise direction. By virtue of its engagement with the gear element 554, the counter-clockwise rotation of the gear element 552 causes the gear element 554 to rotate in a clockwise direction (when viewed from above) about the pin 505. By virtue of its engagement with the gear element 556, the clockwise rotation of the gear element 554 causes the gear element 556 to rotate in a clockwise direction. Since the gear element 556 is attached to the gear element 560 by the shaft 558, rotation of the gear element 556 in the clockwise direction causes the gear element 560 to also rotate in a clockwise direction. By virtue of its engagement with the gear element 562*a*, the clockwise rotation of the gear element 560 causes the gear element 562*a* to rotate in a counter-clockwise direction. Also, since both the gear element 562*a* and the gear element 562*b* are adapted to be non-rotatably mounted to, e.g., keyed to, the pin 513, the rotation of the gear element 562*a* in a counter-clockwise direction also causes the gear element 562*b* to rotate in a counter-clockwise direction.

Thus, the gear element 562*b* and the gear element 512 rotate together in a counter-clockwise direction about their shared longitudinal axes, e.g., the central axis of the pin 513. Since the plate 518 is maintained in its first position, the two openings in the plate 518 are locked in respective engagement with the teeth 516 of gear element 514 and with the teeth 5661 of the gear element 562*b*. Thus, the rotation of the gear element 562*b*, and of the gear element 512 in the counter-clockwise direction about the pin 513, causes the gear element 514 and the gear element 564 to also rotate in a counter-clockwise direction about the pin 513, the central axis of which is coaxial with the longitudinal axis D of the jaw portion 11*a*. The gear element is connected to the screw 520, on which is mounted the push block 522. Since the push block 522 is keyed to the internal surface of the jaw portion 11*a*, the rotation of the gear element 514 about the longitudinal axis D causes the jaw portion 11*a* to rotate relative to the shaft portion 11*b* about its longitudinal axis D.

Once the jaw portion 11*a* is rotated relative to the shaft portion 11*b* about its longitudinal axis D to a desired position, the jaws 50, 80 may be opened so as to enable a section of tissue to be disposed therebetween. To perform this operation, the plate 518 is moved distally to its second position, such that the two openings in the plate 518 are not locked in respective engagement with either the teeth 516 of gear element 514 nor with the teeth 5661 of the gear element 562*b*. The first rotatable drive shaft 500 is then rotated in a first direction while the second rotatable drive shaft 550 is not rotated. For instance, referring to FIG. 3(*b*), in order to open the first jaw 50 relative to the second jaw 80, the first rotatable drive shaft 500 may be rotated in a counter-clockwise direction. The gear element 502 attached to the first rotatable drive shaft 500 is thus also caused to rotate in a counter-clockwise direction. By virtue of its engagement with the gear element 504, the counter-clockwise rotation of the gear element 502 causes the gear element 504 to rotate in a counter-clockwise direction (when viewed from above) about the pin 505. By virtue of its engagement with the gear element 506, the counter-clockwise rotation of the gear element 504 causes the gear element 506 to rotate in a clockwise direction. Since the gear element 506 is attached to the gear element 510 by the shaft 508, rotation of the gear element 506 in the clockwise direction causes the gear element 510 to also rotate in a clockwise direction. By virtue of its engagement with the gear element 512, the clockwise rotation of the gear element 510 causes the gear element 512 to rotate in a counter-clockwise direction. By virtue of its engagement with the gear element 514, the counter-clockwise rotation of the gear element 512 causes the gear element 514 to rotate in a clockwise direction. Since the plate 518 is moved to its second position, the gear element 512 rotates about the pin 513 without the pin 513 rotating.

The clockwise rotation of the gear element 514 causes rotation of the threaded screw 520 in a clockwise direction. In an initial stage of operation, e.g., when the surgical device 11 has first been inserted into a patient's body, the push block 522 is located in a distal-most position along the threaded screw 520. Rotation of the threaded screw 520 causes the push block 522, which is adapted to be non-rotatably mounted within, e.g., keyed to, an internal surface of the surgical device 11, to travel in a proximal direction. The proximal movement of the push block 522 causes the pair of rollers 524 to move proximally within their respective slots 5011 on each side of the upper jaw 50. When the push block 522 has moved to the proximal end of the threaded screw 520, the rollers 524 are positioned at a proximal end of the slots 5011, at which position the first jaw 50 is maximally opened relative to the second jaw 80.

Once the first and second jaws 50, 80 have been opened to a desired position relative to each other, the jaws 50, 80 are closed so as to clamp a section of tissue therebetween. Again, with the plate 518 in its second position, e.g., such that the two openings in the plate 518 are not locked in respective engagement with either the teeth 516 of gear element 514 nor with the teeth 5661 of the gear element 562b, the first rotatable drive shaft 500 is rotated in a second direction while the second rotatable drive shaft 550 is not rotated. For instance, referring to FIG. 3(b), in order to close the first jaw 50 relative to the second jaw 80, the first rotatable drive shaft 500 may be rotated in a clockwise direction. The gear element 502 attached to the first rotatable drive shaft 500 is thus also caused to rotate in a clockwise direction. By virtue of its engagement with the gear element 504, the clockwise rotation of the gear element 502 causes the gear element 504 to rotate in a clockwise direction (when viewed from above) about the pin 505. By virtue of its engagement with the gear element 506, the clockwise rotation of the gear element 504 causes the gear element 506 to rotate in a counter-clockwise direction. Since the gear element 506 is attached to the gear element 510 by the shaft 508, rotation of the gear element 506 in the counter-clockwise direction causes the gear element 510 to also rotate in a counter-clockwise direction. By virtue of its engagement with the gear element 512, the counter-clockwise rotation of the gear element 510 causes the gear element 512 to rotate in a clockwise direction. By virtue of its engagement with the gear element 514, the clockwise rotation of the gear element 512 causes the gear element 514 to rotate in a counter-clockwise direction. Since the plate 518 is moved to its second position, the gear element 512 rotates about the pin 513 without the pin 513 rotating.

The counter-clockwise rotation of the gear element 514 causes rotation of the threaded screw 520 in a counter-clockwise direction. As set forth above, the push block 522 may be located in a proximal-most position along the threaded screw 520. Rotation of the threaded screw 520 causes the push block 522, which is keyed to an internal surface of the surgical device 11, to travel in a distal direction. The distal movement of the push block 522 causes the pair of rollers 524 to move distally within their respective slots 5011 on each side of the upper jaw 50. When the push block 522 has moved to the distal end of the threaded screw 520, the rollers 524 are positioned at a distal end of the slots 5011, at which position the first jaw 50 is maximally clamped against the second jaw 80. It should be noted that, while the opening and closing of the first and second jaws 50, 80 may occur in a simple scissor type fashion, in other embodiments, the first and second jaws 50, 80 may open and close in a different manner. An example of one such type of movement is described in additional detail below in connection with FIGS. 3(f) through 3(i).

Once a section of tissue has been clamped between the first and second jaws 50, 80, the section of tissue may be cut and stapled. It should be recognized that, while the present invention is illustrated as using both cutting and stapling elements, the surgical device 11 may employ only one such element, or else may employ a different type of surgical instrument. Before the surgical device 11 is inserted into a patient's body, a staple cartridge 578 is provided within the second jaw 80. In one embodiment, the surgical device 11 is a single use device, in which the staple cartridge is integral to the second jaw 80. Alternatively, the surgical device 11 may have a replaceable staple cartridge, e.g., replaceable staple cartridge 600 as illustrated in FIG. 3(f), thereby permitting the surgical device 11 to be used numerous times with different staple cartridges. In this embodiment, if the surgical device 11 is being used for the first time, the staple cartridge 600 may be pre-installed during manufacture and assembly of the surgical device 11, or else may be installed by the user just prior to using the surgical device 11. If the surgical device 11 is being used for the second or more time, the staple cartridge 600 may be installed by the user just prior to using the surgical device 11. When the staple cartridge 600 is inserted into the second jaw 80, the distal end 574 of the longitudinal rod 568 is received within the proximally facing opening 605d of the wedge driver 605.

To illustrate the cutting/stapling operation of the surgical device 11, reference is first made to FIG. 3(b). With the staple cartridge 600 installed within the second jaw 80 of the surgical device 11, the plate 518 is maintained in its second position, such that the two openings in the plate 518 are not locked in respective engagement with either the teeth 516 of gear element 514 nor with the teeth 5661 of the gear element 562b. The second rotatable drive shaft 550 is then rotated in a first direction while the first rotatable drive shaft 500 is not rotated. For instance, in order to cut and staple a section of tissue disposed between the first and second jaw 50, 80, the second rotatable drive shaft 550 may be rotated in a counter-clockwise direction. The gear element 552 attached to the second rotatable drive shaft 550 is thus also caused to rotate in a counter-clockwise direction. By virtue of its engagement with the gear element 554, the counter-clockwise rotation of the gear element 552 causes the gear element 554 to rotate in a clockwise direction (when viewed from above) about the pin 505. By virtue of its engagement with the gear element 556, the clockwise rotation of the gear element 554 causes the gear element 556 to rotate in a clockwise direction. Since the gear element 556 is attached to the gear element 560 by the shaft 558, rotation of the gear element 556 in the clockwise direction causes the gear element 560 to also rotate in a clockwise direction. By virtue of its engagement with the gear element 562a, the clockwise rotation of the gear element 560 causes the gear elements 562a and 562b to rotate in a counter-clockwise direction. By virtue of its engagement with the gear element 564, the counter-clockwise rotation of the gear element 562b causes the gear element 564 to rotate in a clockwise direction. Since the plate 518 is moved to its second position, the gear element 562b rotates with the pin 513 without the gear element 514 rotating.

The clockwise rotation of the gear element 564 causes rotation of the first longitudinal rod 566 along with the second longitudinal rod 568 in the clockwise direction. The spring 570 that resides between a distal end of the first longitudinal rod 566 and a shoulder 572 of the second longitudinal rod 568 functions to bias the second longitudinal rod 568 in a distal direction, thereby insuring that the distal end 574 of the second longitudinal rod 568 seats within its respective opening 605d of the wedge driver 605.

To further illustrate the cutting/stapling operation of the surgical device 11, reference is next made to FIG. 3(g). FIG. 3(g) is a cross-sectional view of the surgical device 11, according to one embodiment of the present invention, in a fully closed position. In FIG. 3(g), the surgical device 11 is illustrated absent a section of tissue between the clamping surfaces 106, 108 of the first and the second jaws 50, 80.

As illustrated in FIG. 3(g), the surgical device 11 is disposed within the second jaw 80, and the cutting and stapling element 104 includes the replaceable staple cartridge 600 of FIG. 3(g) that is replaceably mountable within the second jaw 80. The replaceable staple cartridge 600, which was shown in an exploded view in FIG. 3(f), is shown assembled and mounted within the second jaw 80 in FIG. 3(g).

As illustrated in FIG. 3(g), the wedge 603 has disposed thereon a blade 51 having a cutting edge 51a. Alternatively, the cutting and stapling elements may be separately disposed. In the example embodiment illustrated in FIG. 3(g), the blade 51 has a tail region 654 with a contact face 653. The blade 51 is rotatably coupled to the wedge 603 around pivot 51b to allow the blade 51 to rotate between a first and a second position. FIG. 3(g) illustrates the wedge 603 and the blade 51 in several positions, labeled as positions A to E, as the wedge 603 and the blade 51 travel from the distal end 604c to the proximal end 604d of the staple tray 604.

In the position labeled A, the wedge 603 and the blade 51 are positioned at the distal end 604c of the staple tray 604. In the position labeled A, the wedge 603 and the blade 51 are housed within a housing 615 and the blade 51 is rotated relative to the wedge 603 so as to be in a retracted position, e.g., the cutting edge 51a facing upwards and is not exposed. The contact face 653 initially faces the proximal end 604d of the staple tray 604.

In operation, rotation of the wedge driver 605 via the distal end 574 of the second longitudinal rod 568 causes the wedge 603 and the blade 51 to advance to the position labeled B, via. In the position labeled B, the wedge 603 and the blade 51 are positioned proximally relative to the distal end 604c of the staple tray 604. Specifically, in the position labeled B, the wedge 603 and the blade 51 are positioned such that the contact face 653 of the blade 51 begins to contact an actuating lip 615a of the housing 615. As the contact face 653 of the blade 51 begins to contact the actuating lip 615a of the housing 615, the blade 51 begins to rotate relative to the wedge 603.

Further rotation of the wedge driver 605 via the distal end 574 of the second longitudinal rod 568 causes the wedge 603 and the blade 51 to advance to the position labeled C. In the position labeled C, the wedge 603 and the blade 51 are positioned still further proximally relative to the distal end 604c of the staple tray 604. Specifically, in the position labeled C, the wedge 603 and the blade 51 are positioned such that the contact face 653 of the blade 51 has fully contacted the actuating lip 615a of the housing 615. When the contact face 653 of the blade 51 has fully contacted the actuating lip 615a of the housing 615, the blade 51 is fully rotated relative to the wedge 603 such that the cutting edge 51a of the blade 51 is in an extended position, e.g., the cutting edge 51a faces the proximal end 604d of the staple tray 604.

Further rotation of the wedge driver 605 via the distal end 574 of the second longitudinal rod 568 causes the wedge 603 and the blade 51 to advance to the position labeled D. In the position labeled D, the wedge 603 and the blade 51 are positioned approximately at the midpoint between the distal end 604c and the proximal end 604d of the staple tray 604. In the position labeled D, the blade 51 is maintained in the extended position having the cutting edge 51a facing the proximal end 604d of the staple tray 604 so as to cut a section of tissue (not shown) that is clamped between the first jaw 50 and the second jaw 80.

Further rotation of the wedge driver 605 via the distal end 574 of the second longitudinal rod 568 causes the wedge 603 and the blade 51 to advance to the position labeled E. In the position labeled E, the wedge 603 and the blade 51 are positioned at the proximal end 604d of the staple tray 604. In the position labeled E, the blade 51 is still maintained in the extended position with the cutting edge 51a facing the proximal end 604d of the staple tray 604. Here, however, the blade 51 is enclosed within a housing 616 so that the cutting edge 51a is not exposed.

The staples 606 housed within the staple tray 604 may simultaneously be fired with the movement of the blade 51 from the proximal end 80b to the distal end 80a of the second jaw 80. For instance, rotation of the wedge driver 605 via the distal end 574 of the second longitudinal rod 568 causes the wedge 603 to be moved through the central channel 604e of the staple tray 604. As the wedge 603 is moved from the distal end 604c to the proximal end 604d of the staple tray 604 through the central channel 604e, the pair of sloped edges 603b of the wedge 603 slideably engage the respective top surfaces 607a of the staple pushers 607 and successively push the staple pushing fingers 607c of the staple pushers 607 into, and thus the staples 606 out of, the slots 604h in the staple tray 604. When the surgical device 11 is in the closed position, the rows 702 of the staple guides 703 align with the slots 604h of the staple tray 604 in the second jaw 80 so that the staples 606 maintained in the slots 604h of the staple tray 604 are pushed by the staple pushing fingers 607c of the staple pushers 607 into, and closed by, corresponding staple guides 703 of the anvil member 700. The staple guides 703 receive the prongs 606b of the staples 606 when the surgical device 11 is fired and bend the prongs 606b so as to close the staples 606, thereby stapling the section of tissue.

It should be recognized that, according to various embodiments of the present invention, the blade 51 and the wedge 603 may be moved in either a proximal or a distal direction in order to cut a section of tissue disposed between the first jaw 50 and the second jaw 80. Furthermore, it should be recognized that, according to various embodiments of the present invention, any mechanical arrangement that is configured to move the blade 51 and the wedge 603 in order to cut and/or staple a section of tissue disposed between the first jaw 50 and the second jaw 80 may be employed.

As set forth above, while the opening and closing of the first and second jaws 50, 80 may occur in a simple scissor type fashion, in other embodiments, the first and second jaws 50, 80 may open and close in a different manner. An example of one such type of movement is described generally below in connection with FIGS. 3(i) through 3(l). Further details and benefits of this type of movement are described in patent application Ser. No. 10/460,291, filed Jun. 11, 2003, which is expressly incorporated herein in its entirety by reference thereto. For the purposes of clarity, those components of the surgical device 11 that are located proximal to the gear element 514 and the gear element 564 are not shown. It should be understood that these gear elements 514, 564 may be driven by the combination of drive components illustrated in FIGS. 3(a) through 3(e), or by any other combination of driving components.

Figure 3I:
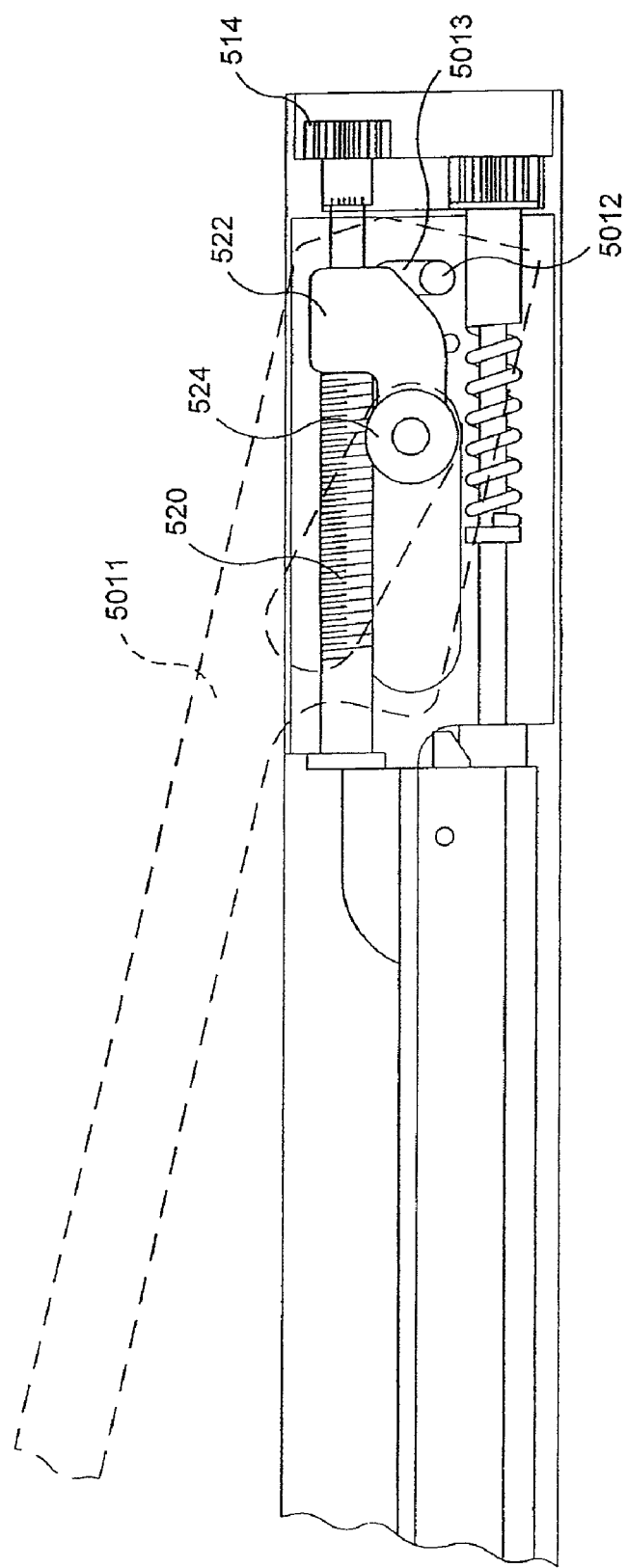

FIG. 3(i) illustrates the first jaw 50 in an open position relative to the second jaw 80. In this position, the push block 522 is at or near a proximal end of the threaded screw 520, and the'rollers 524 attached to the push block 522 are positioned at or near the proximal end of slots 5011 of the first jaw 50. The first jaw 50 includes a pivot pin 5012, which is engaged within a vertical slot 5013 of the second jaw 80. The proximal ends 50b, 80b of the first and second jaws 50, 80, respectively, are biased apart from each other, such that, in the initial position shown in FIG. 3(i), the pin 5012 is positioned at the lower end of the slot 5013.

Figure 3J:
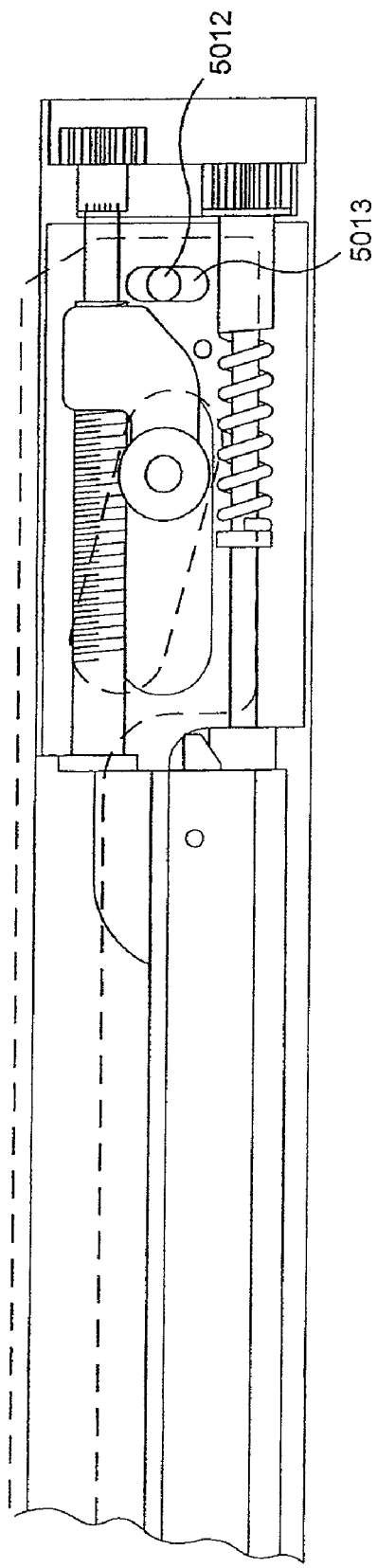
Figure 3K:
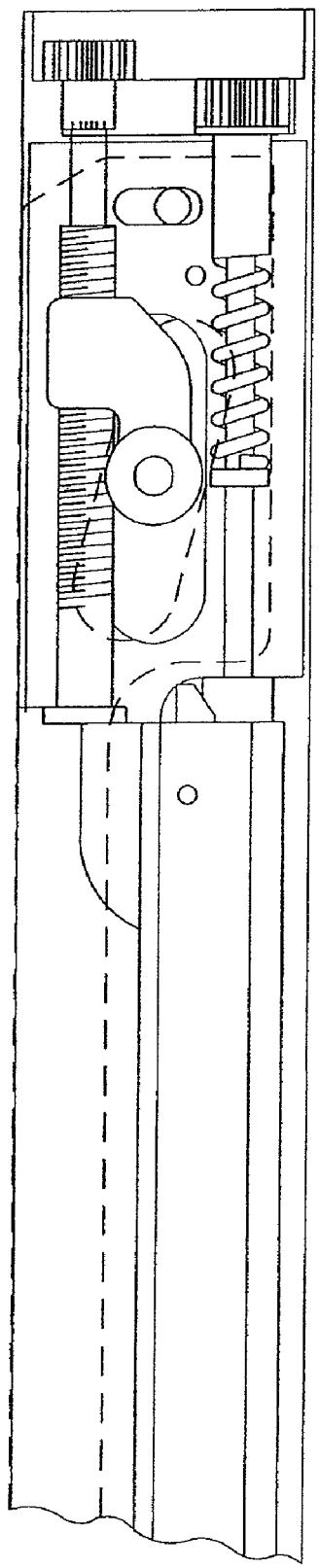
Figure 31:
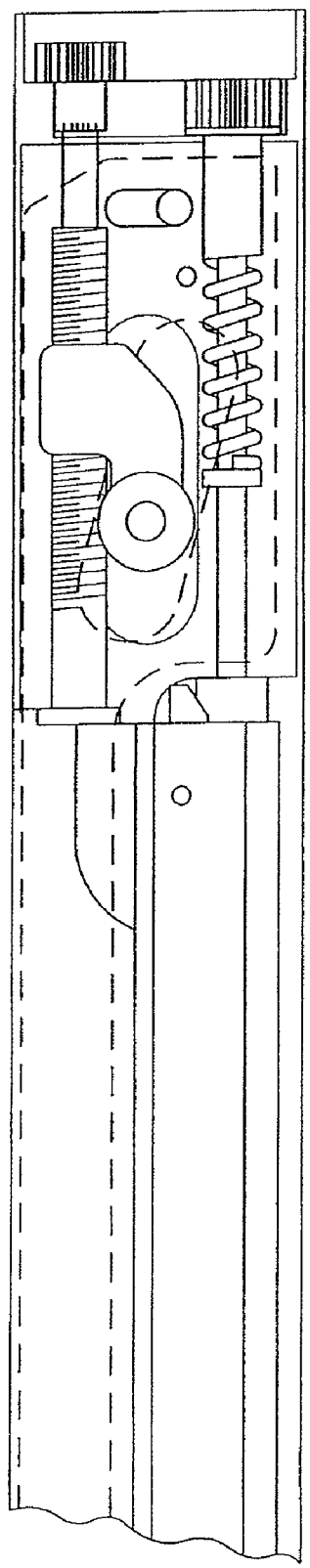

Referring to FIG. 3(j), as the gear element 514 is rotated, the push block 522 moves distally to a first intermediate position of the threaded screw 520, and the rollers 524 attached to the push block 522 are likewise moved distally to a first intermediate position within the slots 5011 of the first jaw 50. In the position shown in FIG. 3(*j*), the pin 5012 has moved within the slot 5013 until it eventually is positioned at the upper end of the slot 5013. In this manner, the distal ends 50*a*, 80*a* of the first and second jaws 50, 80 are brought together prior to the first and second jaws 50, 80 being fully clamped together.

Referring to FIG. 3(*k*), as the gear element 514 is further rotated, the push block 522 continues to move distally to a second intermediate position of the threaded screw 520, and the rollers 524 attached to the push block 522 are likewise continued to move distally to a second intermediate position within the slots 5011 of the first jaw 50. In the position shown in FIG. 3(*k*), the further clamping of the first and second jaws 50, 80 cause the pin 5012 to again move within the slot 5013 until it is eventually positioned at the lower end of the slot 5013. In this manner, the distal ends 50*a*, 80*a* of the first and second jaws 50, 80 remain together while the proximal portions of the first and second jaws 50, 80 are gradually clamped together. Continued distal movement of the push block 522 along the threaded screw 520 eventually places the surgical device 11 in the position illustrated in FIG. 3(*l*), in which the first and second jaws 50, 80 are clamped together at both their distal ends 50*a*, 80*a* and their proximal ends 50*b*, 80*b*.

Figure 4A:
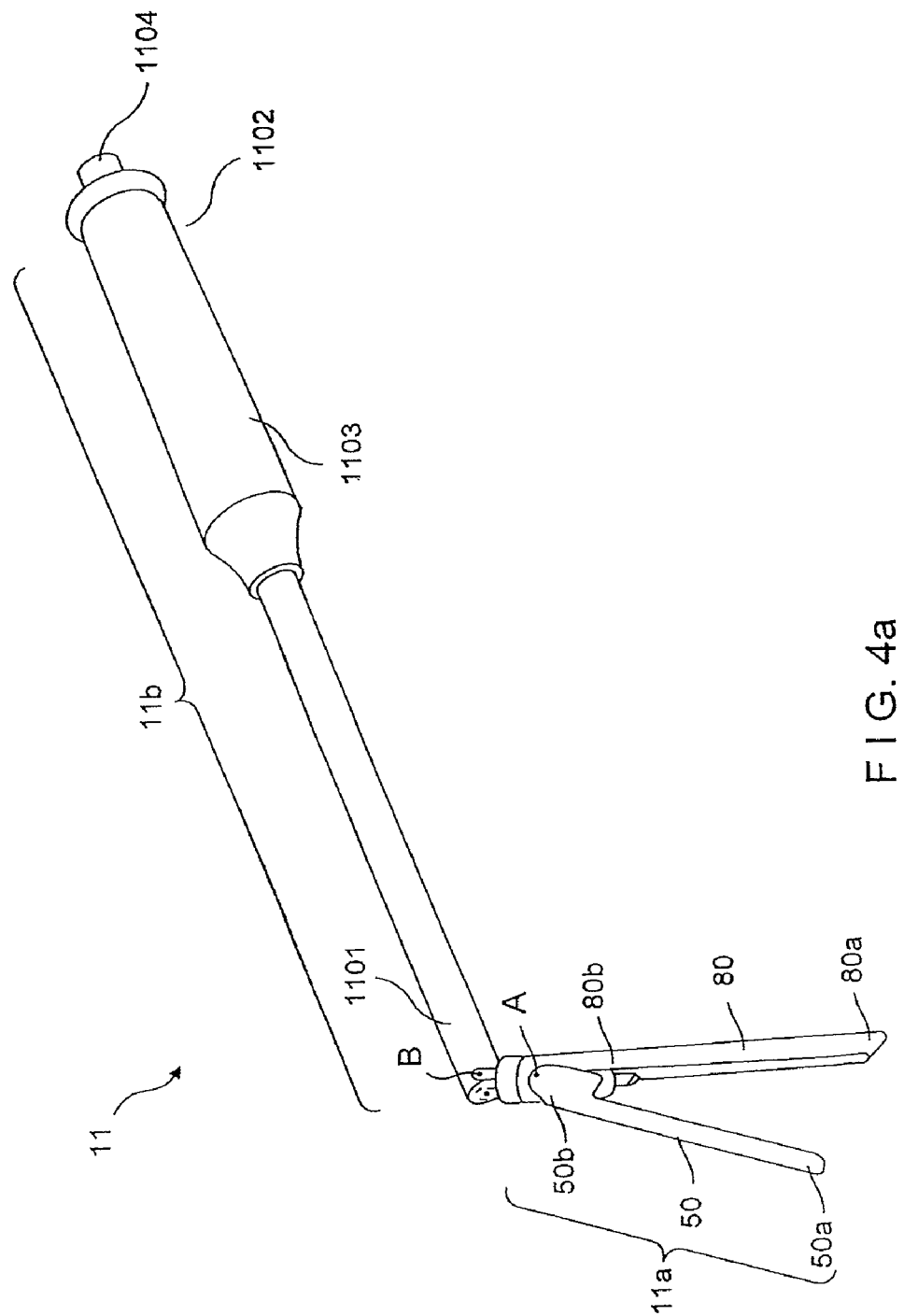
FIG. 4(a) is a perspective view of an articulating clamping, cutting and stapling attachment, according to another example embodiment of the present invention.
Figure 4B:
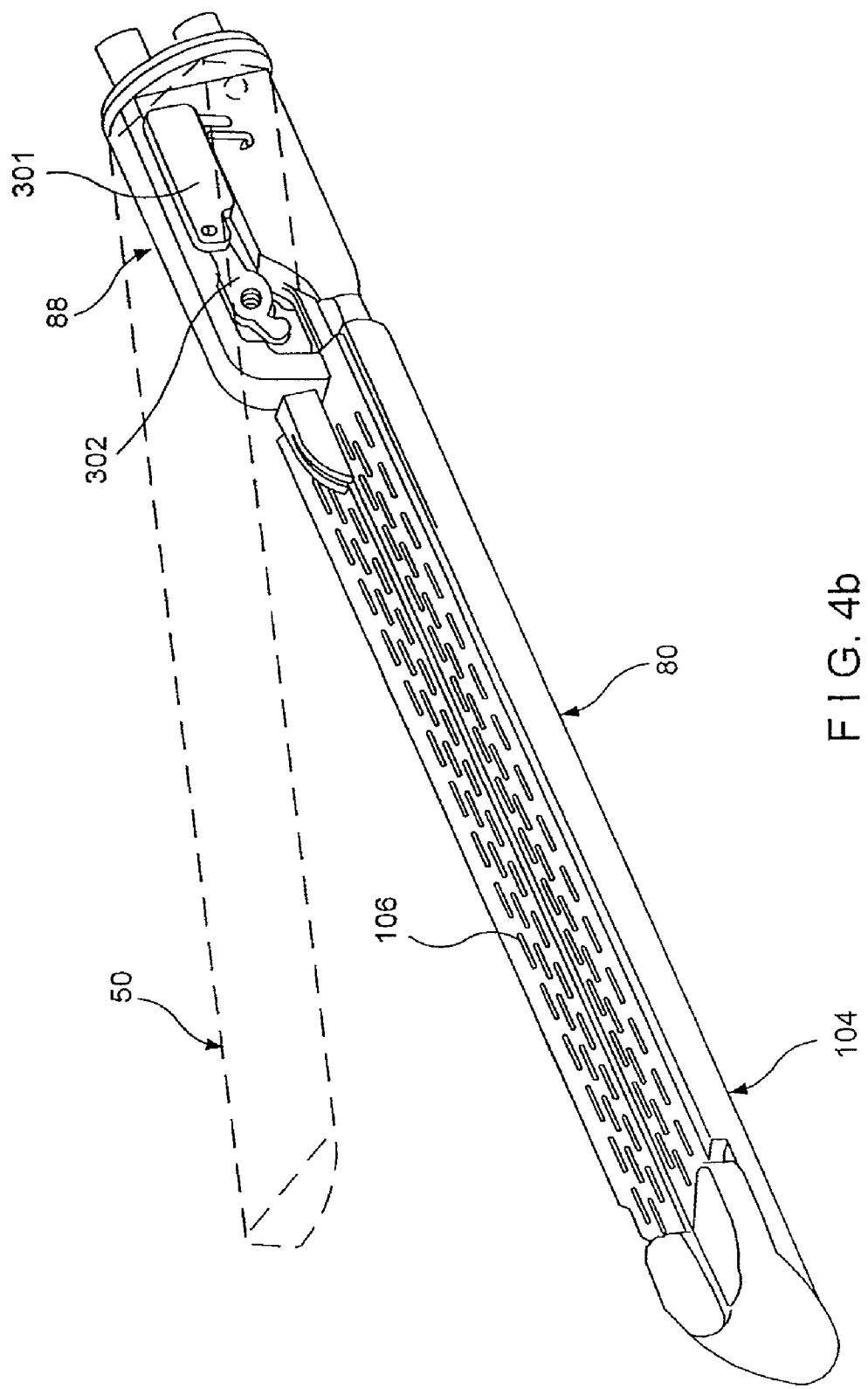
FIG. 4(b) is a perspective view that illustrates additional features of the second jaw of the jaw portion, according to an example embodiment of the present invention.
Figure 5A:
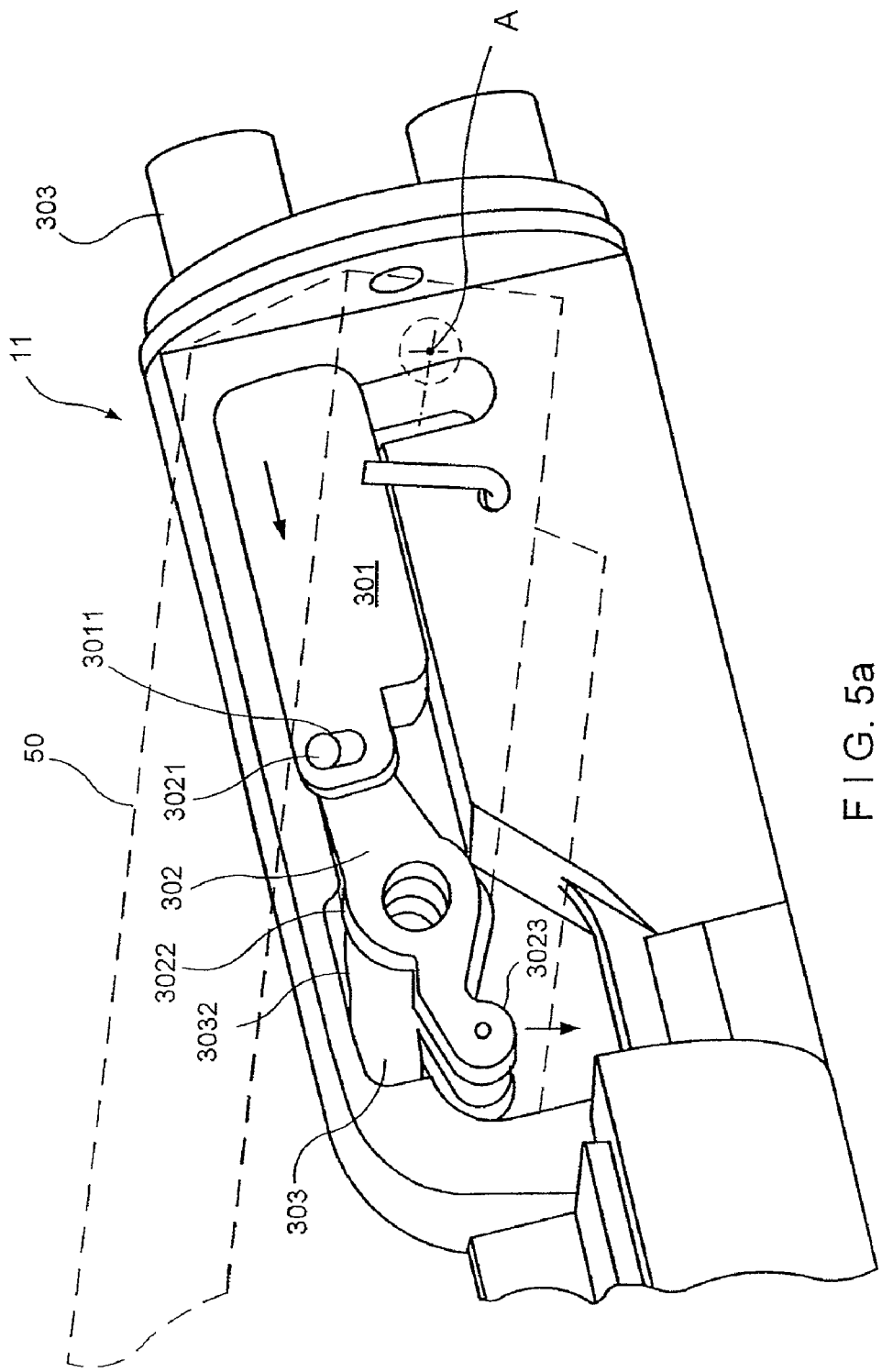
FIG. 5(a) is a perspective view that illustrates the proximal end of the second jaw, according to an example embodiment of the present invention.
Figure 5B:
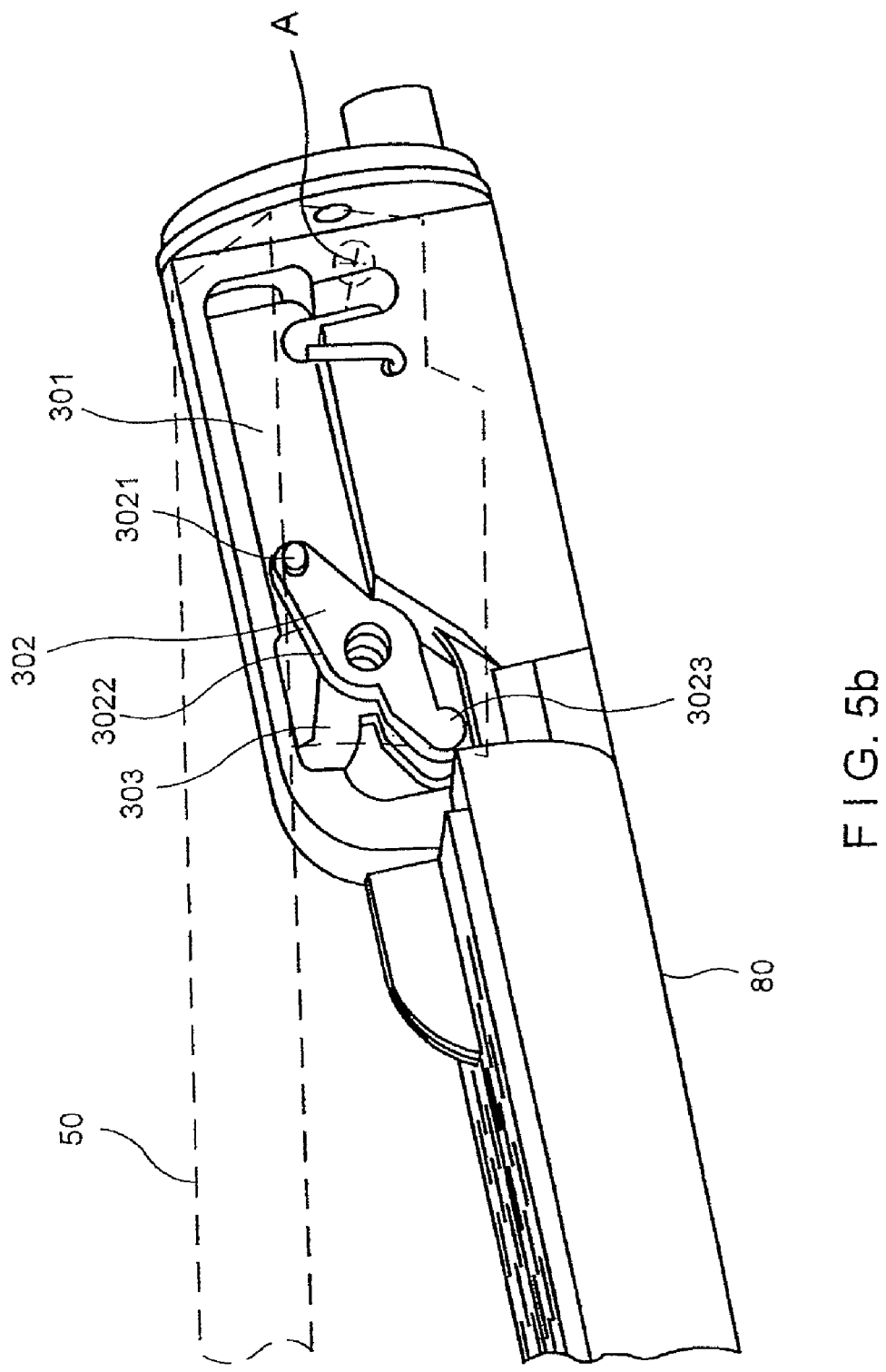
FIG. 5(b) illustrates the surgical device of FIG. 4(a) when moved into a first partially closed position.
Figure 5C:
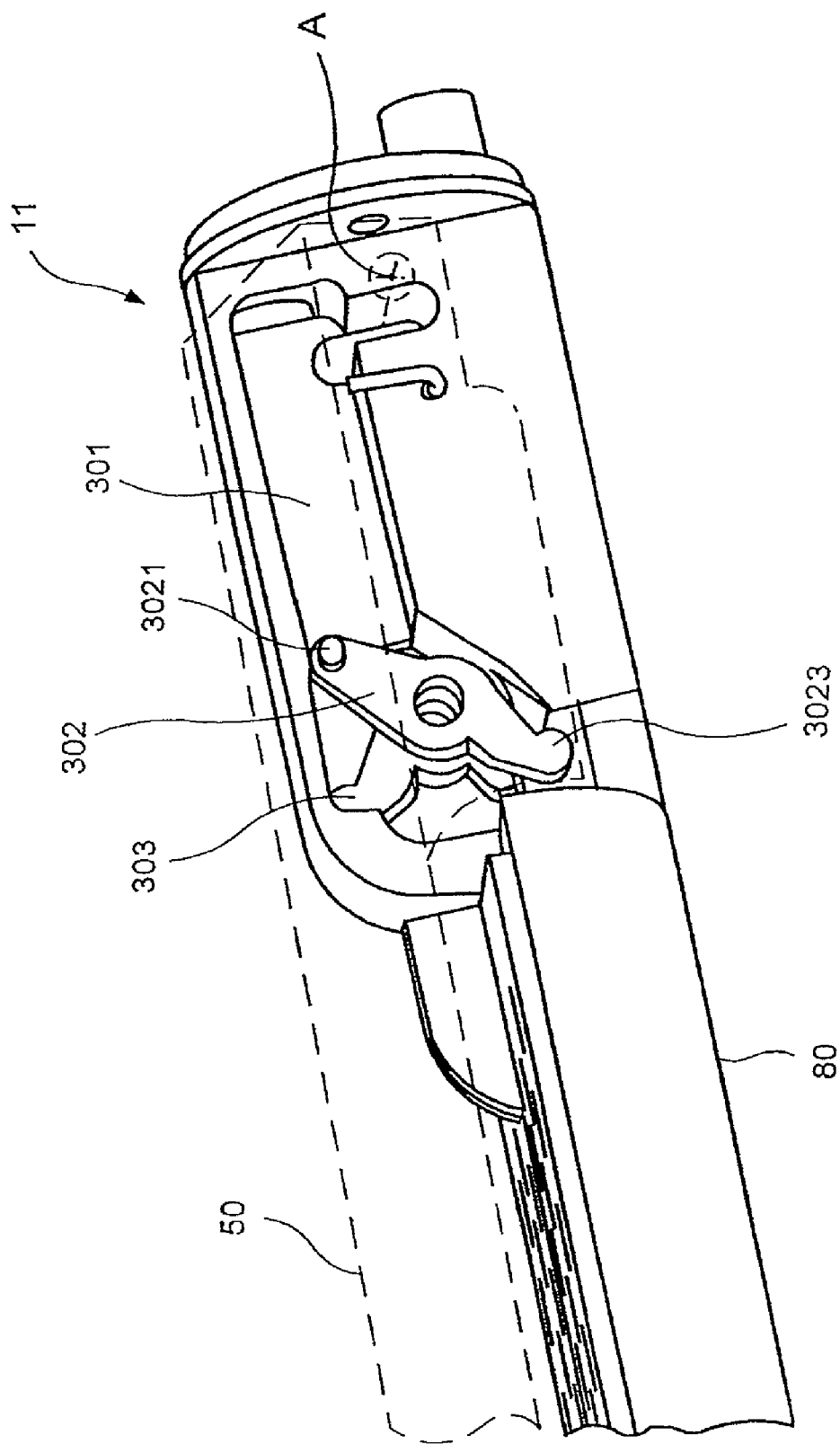
FIG. 5(c) illustrates the surgical device of FIG. 4(a) when moved into a second partially closed position.
Figure 5D:
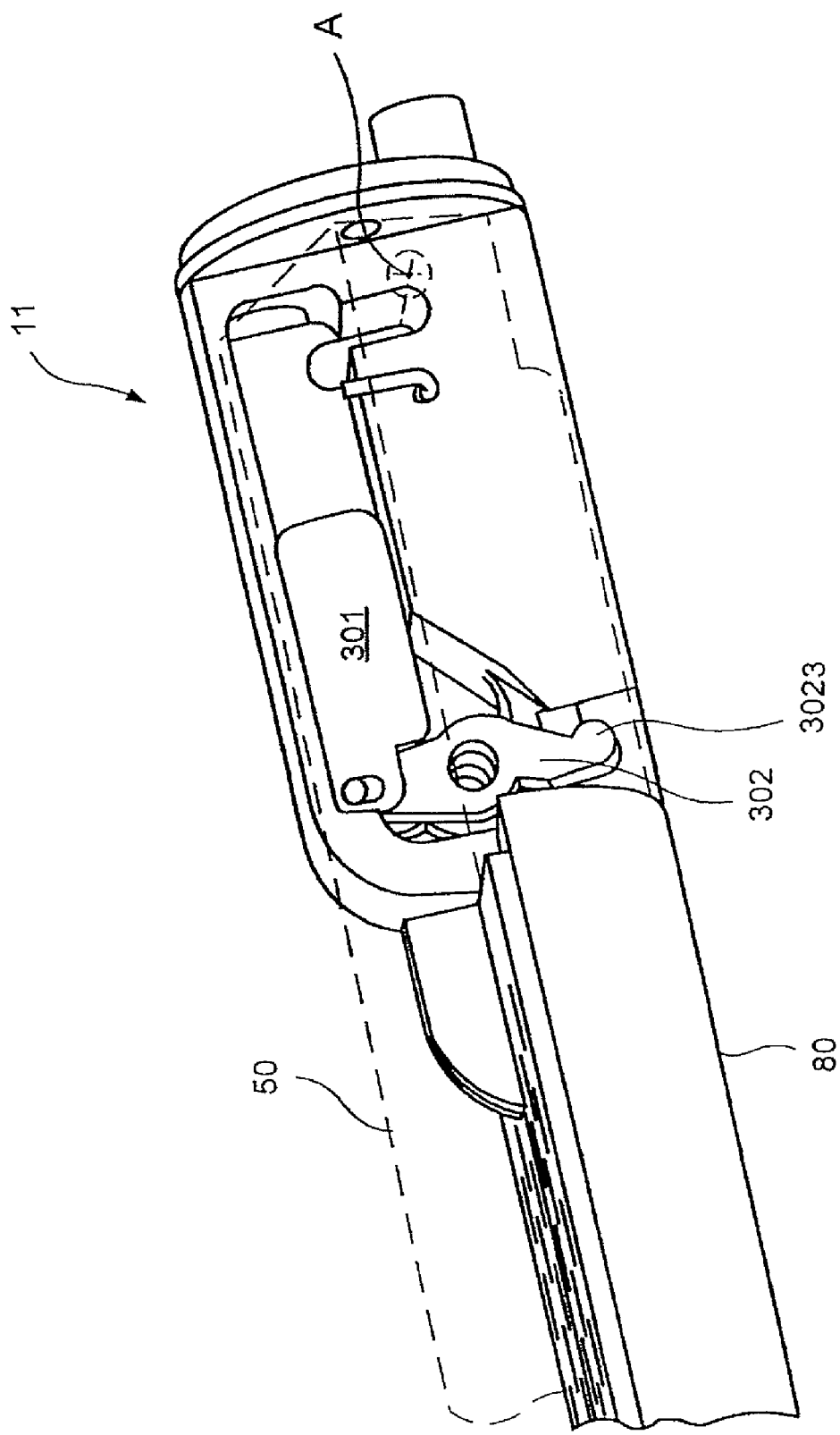
FIG. 5(d) illustrates the surgical device of FIG. 4(a) when moved into a fully closed position.

As set forth above, there are various different mechanisms that may be employed to move the first jaw 50 relative to the second jaw 80. Irrespective of the mechanism employed for this purpose, it is generally desirable to use a mechanism that exerts a strong clamping force on a section of tissue that is disposed between the first jaw 50 and the second jaw 80. FIG. 4(*a*) is a perspective view of the surgical device 11, according to another embodiment of the present invention, which employs a different mechanism for moving the first jaw 50 relative to the second jaw 80.

FIG. 4(*b*) is a perspective view that illustrates additional features of the second jaw 80 of the jaw portion 11*a*. For the purpose of clarity, the first jaw 50 is shown in ghost lines. Specifically, FIG. 4(*b*) illustrates portions of the first driver 88, e.g., a horizontal driver element 301 that is connected to a first rotatable clamping element 302. These and other features of the first driver 88, according to this embodiment, are further illustrated in FIGS. 5(*a*) to 5(*d*).

FIG. 5(*a*) is a perspective view that illustrates the proximal end 80*b* of the second jaw 80. The proximal end 50*b* of the first jaw 50 is shown in ghost lines. FIG. 5(*a*) illustrates the surgical device 11 in a fully open position. In this embodiment, the first driver 88 includes a rotating shaft 303. The first driver 88 also includes the horizontal driver element 301. A proximal end of the horizontal driver element 301 is engaged by the rotating shaft 303. A distal end of the horizontal driver element 301 includes an opening 3011. The first driver 88 also includes a first rotatable clamping element 302. The first rotatable clamping element 302 has a proximal end 3021, a middle portion 3022 and a distal end 3023.

The first driver 88 also includes a second rotatable clamping element 303. The second rotatable clamping element 303 has a proximal end 3032 and a distal end 3031. The proximal end of the first rotatable clamping element 302 is pivotably connected to the opening 3011 at the distal end of the horizontal driver element 301. The middle portion 3022 of the first rotatable clamping element 302 is pivotably connected to the proximal end 3032 of the second rotatable clamping element 303. The distal end 3021 of the first rotatable clamping element 302 is pivotably connected to the first jaw 50. The distal end 3031 of the second rotatable clamping element 303 is pivotably connected to the second jaw 50. Also, the proximal end 50*b* of the first jaw 50 is pivotably connected to the proximal end 80*b* of the second jaw 80 around pivot point A.

Upon engagement of the first driver 88, the surgical device 11 is moved into a first partially closed position, as illustrated in FIG. 5(*b*). Specifically, upon engagement of the first motor 96, the first drive shaft 94 causes rotation of the first drive socket 654 in a first direction. Rotation of the first drive socket 654 causes rotation of the rotating shaft 303 of the first driver 88, which in turn causes the horizontal driver element 301 to move in a distal direction. It should be recognized that the components of the first driver 88, while described in connection with this embodiment as including a rotating shaft 303, may include some or all of the components described in connection with the embodiment illustrated in FIG. 3(*a*) through 3(*e*) as set forth above, or else may include any other arrangement of components suitable for moving the horizontal driver element 301 in a distal direction driving.

Still referring to FIG. 5(*b*), distal movement of the horizontal driver element 301 causes rotation of the first rotatable clamping element 302, such that the distal end 3023 of the second rotatable clamping element 302 begins to move in a downward direction. The downward movement of the distal end 3023 of the second rotatable clamping element 302, by virtue of its pivotable attachment to the first jaw 50, causes the first jaw 50 to rotate relative to the second jaw 80 around pivot point A into the partially closed position.

Upon further engagement of the first driver 88, the surgical device 11 is moved into a second partially closed position, as illustrated in FIG. 5(*c*). Specifically, upon further engagement of the first motor 96, the horizontal driver element 301 is caused to move in a still further distal direction via the rotation of the first drive shaft 94, the first drive socket 654 and the rotating shaft 303 of the first driver 88. Continued distal movement of the horizontal driver element 301 causes further rotation of the first rotatable clamping element 302, such that the distal end 3023 of the second rotatable clamping element 302 continues to move in a downward direction. The continued downward movement of the distal end 3023 of the second rotatable clamping element 302, by virtue of its pivotable attachment to the first jaw 50, causes the first jaw 50 to rotate relative to the second jaw 80 around pivot point A into a nearly fully closed position.

Upon further engagement of the first driver 88, the surgical device 11 is moved into a fully closed position, as illustrated in FIG. 5(*d*). Specifically, upon still further engagement of the first motor 96, the horizontal driver element 301 is caused to move to a fully distal position via the rotation of the first drive shaft 94, the first drive socket 654 and the rotating shaft 303 of the first driver 88. In the fully distal position, the first rotatable clamping element 302 is fully rotated, such that the distal end 3023 of the first rotatable clamping element 302 is in a fully lowered position. In the fully lowered position, the distal end 3023 of the first rotatable clamping element 302 has moved the first jaw 50 around pivot point A to a fully closed position, such that a section of tissue 52 disposed between the first and second jaws 50, 80 is fully clamped between the first and second jaws 50, 80.

Figure 1:
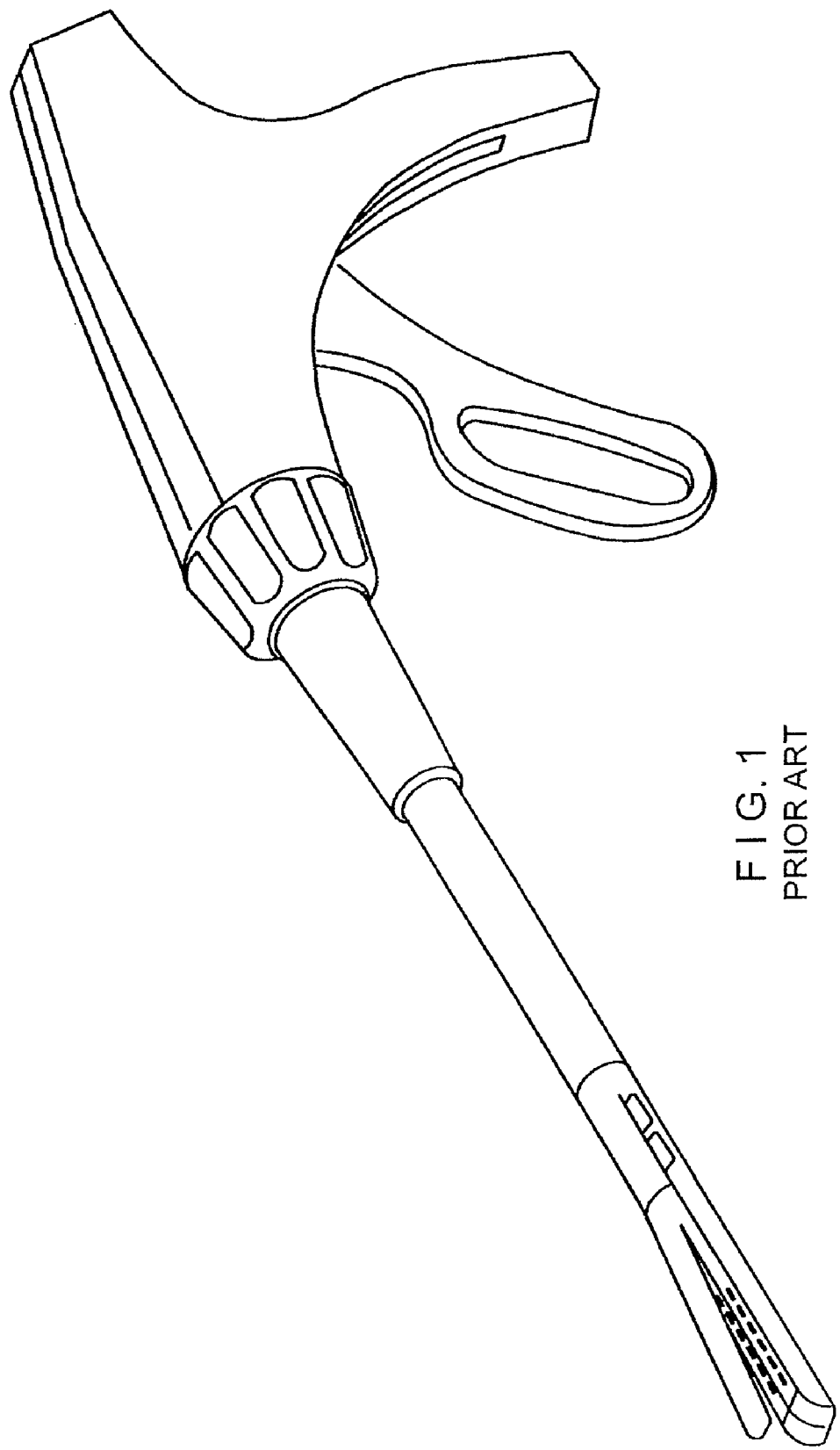
FIG. 1 is a perspective view of a conventional linear clamping, cutting and stapling device.

According to an example embodiment of the present invention, the surgical device 11 may be configured as an attachment to, or may be integral with, a purely mechanical device driver system, such as that illustrated in FIG. 1. In another embodiment, the surgical device 11 may be configured as an attachment to, or may be integral with, an electro-mechanical surgical system, such as an electro-mechanical driver system 1610 illustrated in FIG. 2(*a*).

Specifically, FIG. 2(*a*) is a perspective view of an example embodiment of an electro-mechanical driver component 1610 according to the present invention. Such an electromechanical surgical system is described in, e.g., U.S. patent application Ser. No. 09/723,715, filed on Nov. 28, 2000, now issued as U.S. Pat. No. 6,793,652 on Sep. 21, 2004, U.S. patent application Ser. No. 09/836,781, filed on Apr. 17, 2001, U.S. patent application Ser. No. 09/887,789, filed on Jun. 22, 2001 and U.S. patent application Ser. No. 10/099,634, filed on Mar. 15, 2002, each of which is expressly incorporated herein in their entirety by reference thereto. The electromechanical driver component 1610 may include, for example, a remote power console 1612, which includes a housing 1614 having a front panel 1615. Mounted on the front panel 1615 are a display device 1616 and indicators 1618a, 1618b. A flexible shaft 1620 may extend from the housing 1614 and may be detachably attached thereto via a first coupling 1622. The distal end 1624 of flexible shaft 1620 may include a second coupling 1626 adapted to detachably couple, e.g., the surgical device 11 described above, to the distal end 1624 of the flexible shaft 1620. The second coupling 1626 may also be adapted to detachably attach a different surgical instrument or attachment. In another example embodiment, the distal end 1624 of the flexible shaft 1620 may permanently attach to or be integral with a surgical instrument.

Figure 6A:
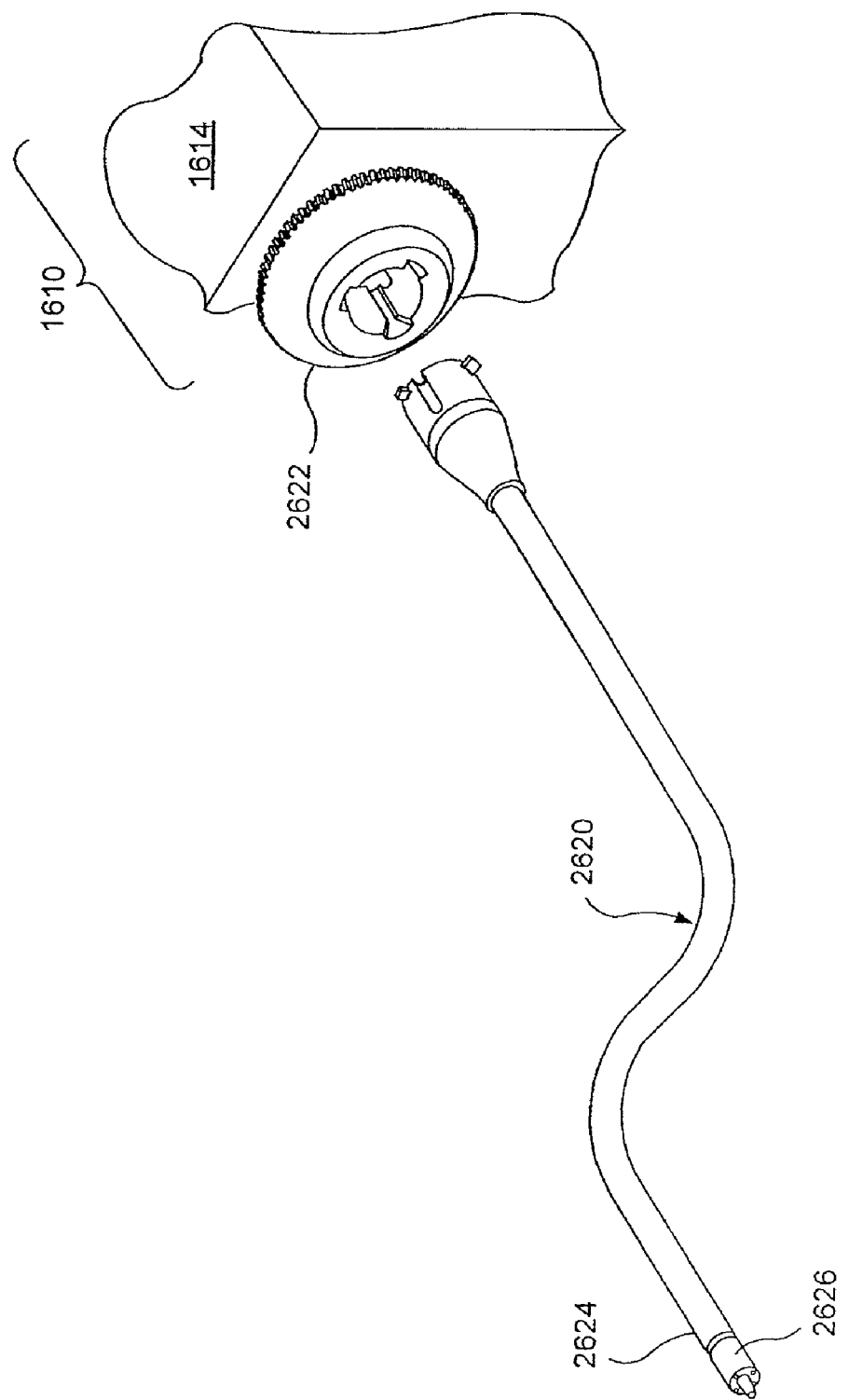
FIG. 6(a) illustrates a flexible shaft and a first coupling, according to an example embodiment of the present invention.
Figure 6C:
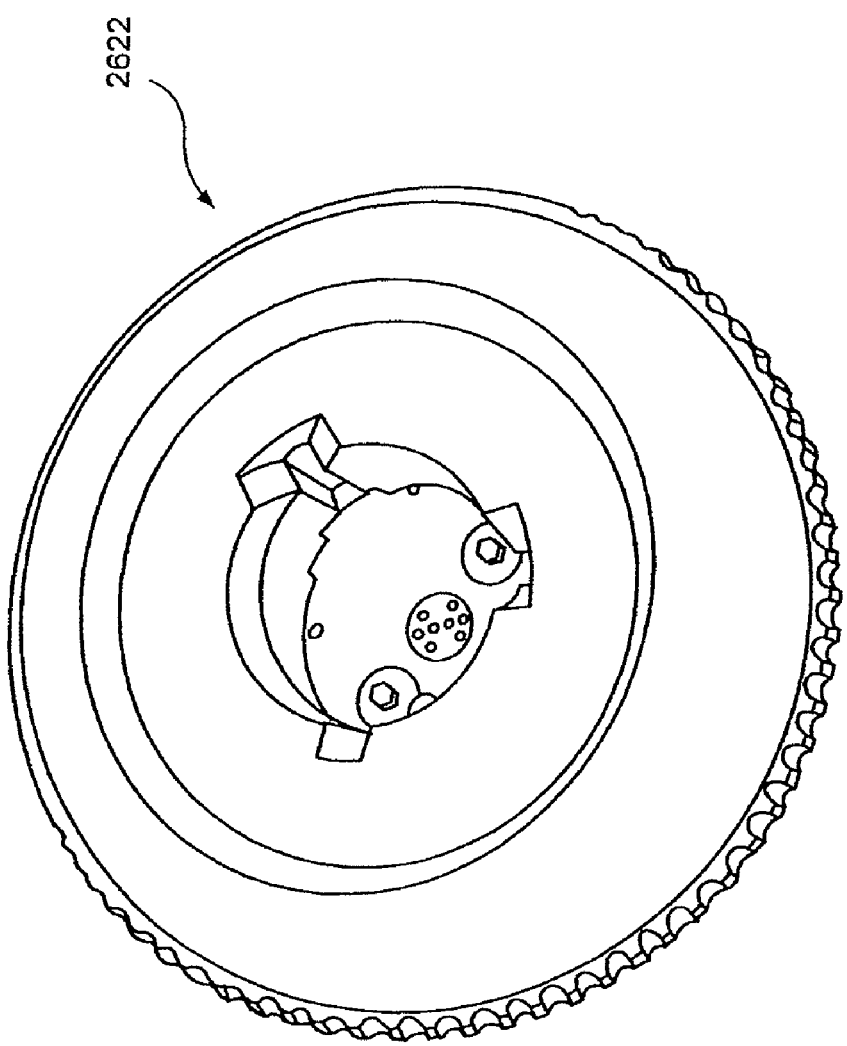
FIG. 6(c) illustrates a front perspective view of the first coupling, according to the example embodiment shown in FIG. 6(b)
Figure 6D:
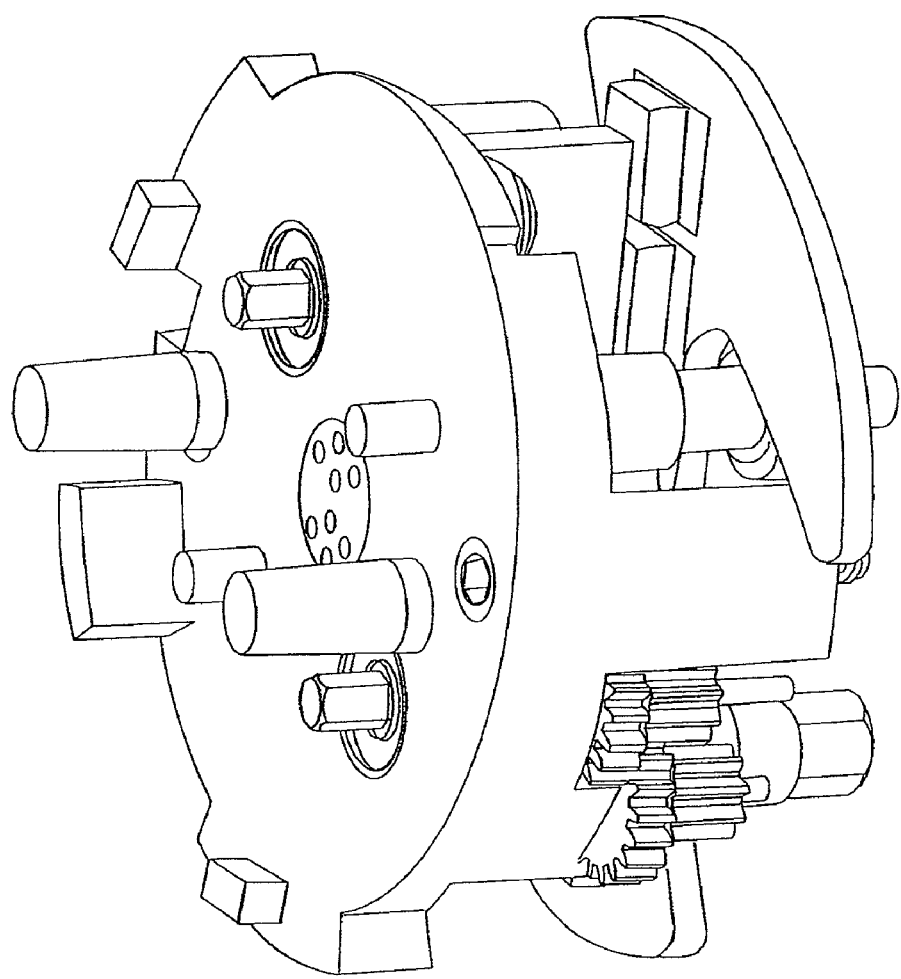
FIG. 6(d) is a side perspective view of some of the internal components of the first coupling, according to an example embodiment of the present invention.
Figure 6E:
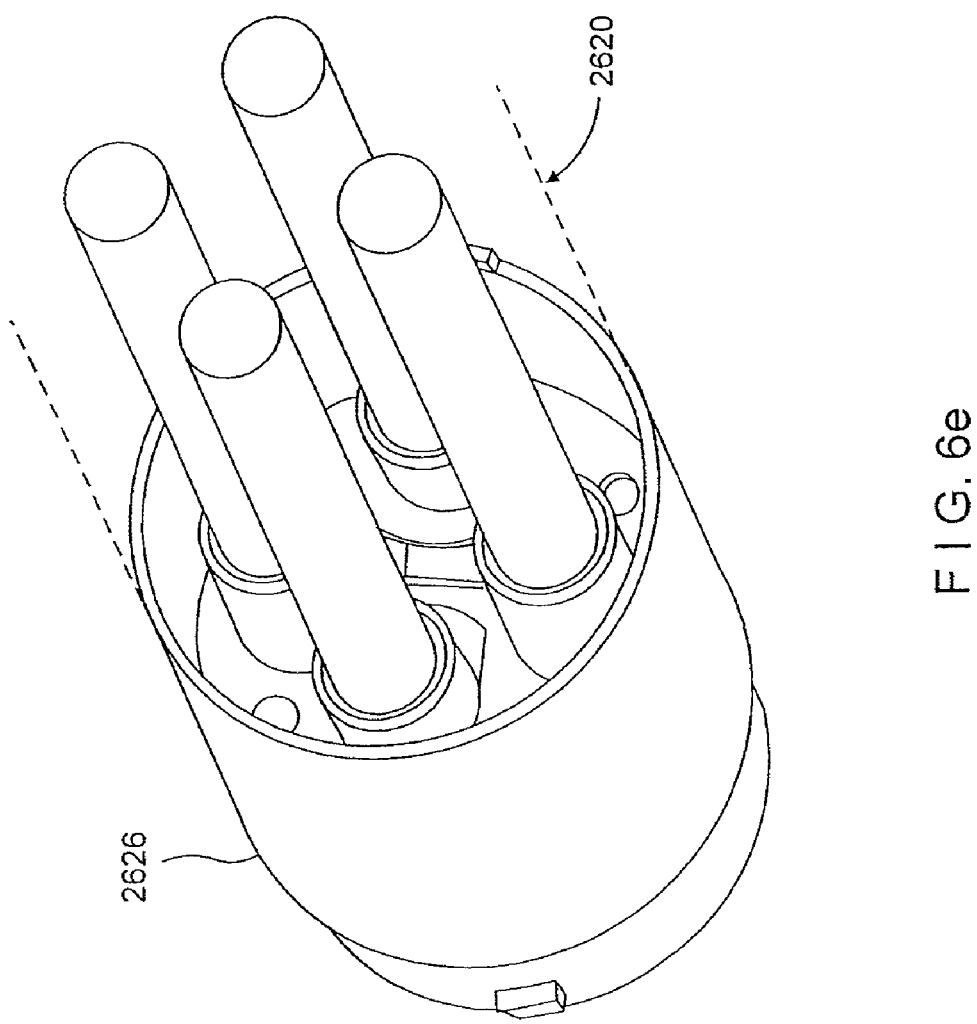
FIG. 6(e) is a rear perspective view of the second coupling at the distal end of the flexible shaft, according to an example embodiment of the present invention.

FIGS. 6(a) through 6(e) illustrate, according to one embodiment of the present invention, an arrangement of couplings and flexible shaft that may be employed in order to connect the surgical device 11 to the electro-mechanical drive component 1610. For instance, FIG. 6(a) illustrates a flexible shaft 2620 that extends from the housing 1614 that is detachably attached thereto via a first coupling 2622. The distal end 2624 of flexible shaft 2620 may include a second coupling 2626 adapted to detachably couple, e.g., the surgical device 11 described above, to the distal end 2624 of the flexible shaft 2620. FIG. 6(b) illustrates a rear perspective view of the first coupling 2622, according to one embodiment of the present invention. FIG. 6(c) illustrates a front perspective view of the first coupling 2622, according to the embodiment shown in FIG. 6(b). FIG. 6(d) is a side perspective view of some of the internal components of the first coupling 2622. FIG. 6(e) is a rear perspective view of the second coupling 2626 at the distal end 2624 of the flexible shaft 2620, according to one embodiment of the present invention. For the purposes of clarity, the flexible shaft 2620 is shown in FIG. 6(e) as ghost lines. Additional features of these components are further described in Applicant's co-pending patent application designated as 60/703,227.

Figure 8:
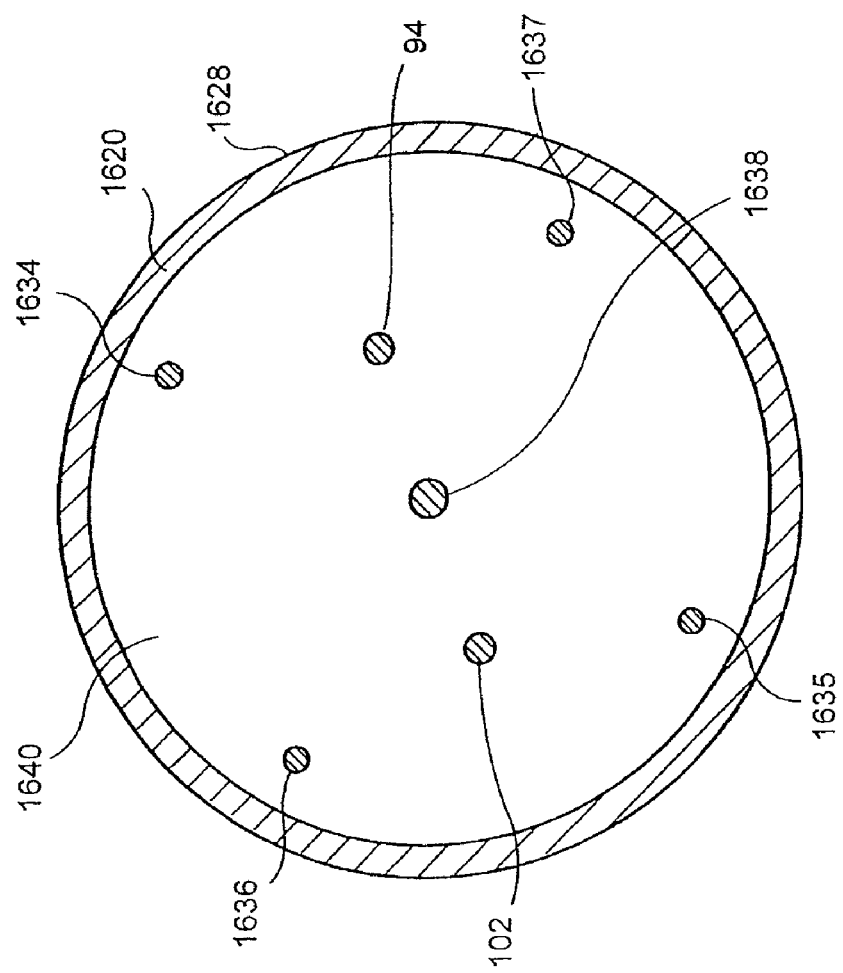
FIG. 8 is a cross-sectional view of the flexible shaft taken along the line 8-8 illustrated in FIG. 7.

While the combination of the flexible shaft 2620 and couplings 2622, 2626 provide one arrangement by which the surgical device 11 may be attached to the electro-mechanical power console 1610, any suitable arrangement may be employed. For instance, FIGS. 7 through 10 illustrate another arrangement by which the surgical device 11 may be attached to the electro-mechanical power console 1610. Referring to FIG. 7, there is seen a side view, partially in section, of the flexible shaft 1620. According to an example embodiment, the flexible shaft 1620 includes a tubular sheath 1628, which may include a coating or other sealing arrangement configured to provide a fluid-tight seal between the interior channel 1640 thereof and the environment. The sheath 1628 may be formed of a tissue-compatible, sterilizable elastomeric material. The sheath 1628 may also be formed of a material that is autoclavable. Disposed within the interior channel 1640 of the flexible shaft 1620, and extending along the entire length thereof, may be a first rotatable drive shaft 94, a second rotatable drive shaft 102, a first steering cable 1634, a second steering cable 1635, a third steering cable 1636, a fourth steering cable 1637 and a data transfer cable 1638. FIG. 8 is a cross-sectional view of the flexible shaft 1620 taken along the line 8-8 illustrated in FIG. 7 and further illustrates the several cables 94, 102, 1634, 1635, 1636, 1637 and 1638. Each distal end of the steering cables 1634, 1635, 1636, 1637 is affixed to the distal end 1624 of the flexible shaft 1620. Each of the several cables 94, 102, 1634, 1635, 1636, 1637, 1638 may be contained within a respective sheath.

The first rotatable drive shaft 94 and the second rotatable drive shaft 102 may be configured, for example, as highly flexible drive shafts, such as, for example, braided or helical drive cables. It should be understood that such highly flexible drive cables may have limited torque transmission characteristics and capabilities. It should also be understood that the surgical device 11, or other attachments connected to the flexible shaft 1620, may require a higher torque input than the torque transmittable by the drive shafts 94, 102. The drive shafts 94, 102 may thus be configured to transmit low torque but high speed, the high-speed/low-torque being converted to low-speed/high-torque by gearing arrangements disposed, for example, at the distal end and/or the proximal end of the drive flexible shaft 1620, in the surgical instrument or attachment and/or in the remote power console 1612. It should be appreciated that such gearing arrangement(s) may be provided at any suitable location along the power train between the motors disposed in the housing 1614 and the attached surgical instrument or other attachment connected to the flexible shaft 1620. Such gearing arrangement(s) may include, for example, a spur gear arrangement, a planetary gear arrangement, a harmonic gear arrangement, cycloidal drive arrangement, an epicyclic gear arrangement, etc.

Figure 9:
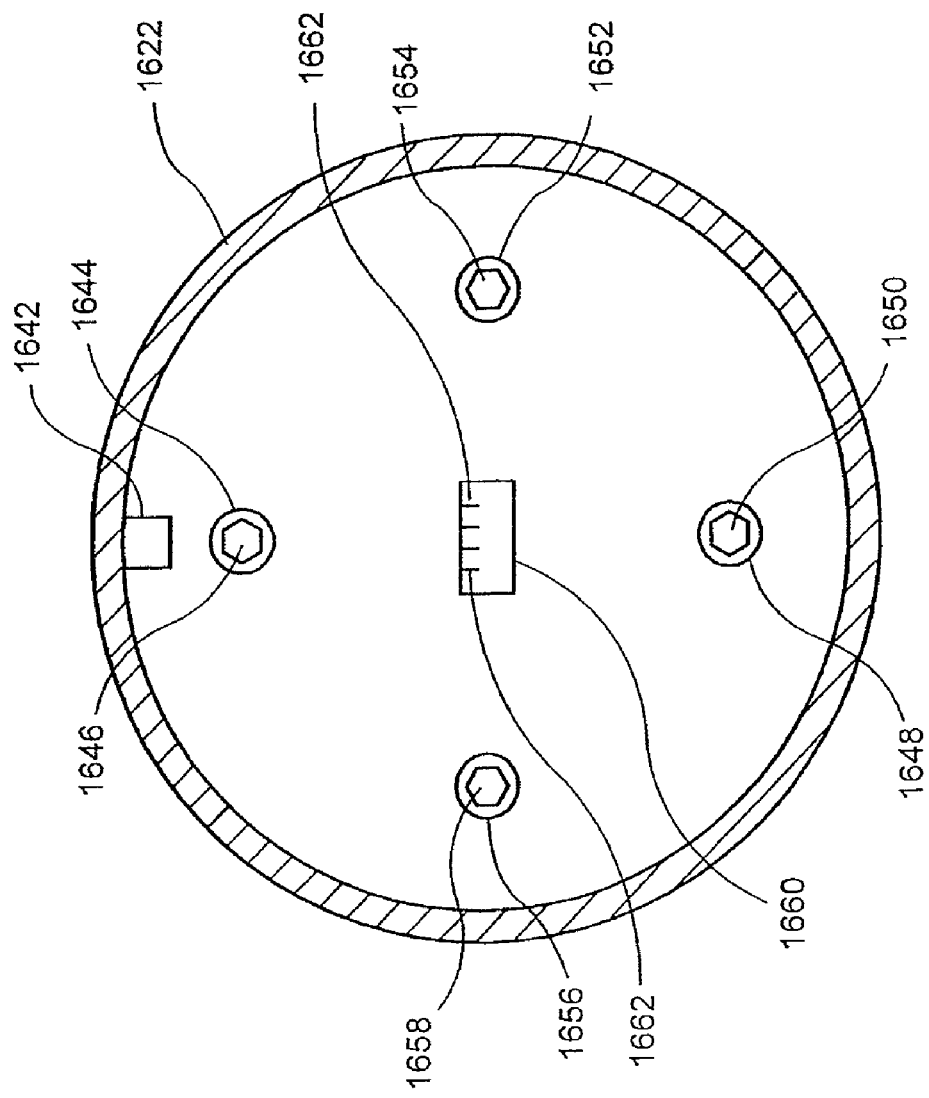
FIG. 9 illustrates a rear end view of first coupling, according to an example embodiment of the present invention.

Referring now to FIG. 9, there is seen a rear end view of first coupling 1622. The first coupling 1622 includes a first connector 1644, a second connector 1648, a third connector 1652 and a fourth connector 1656, each rotatably secured to the first coupling 1622. Each of the connectors 1644, 1648, 1652, 1656 includes a respective recess 1646, 1650, 1654, 1658. As illustrated in FIG. 9, each recess 1646, 1650, 1654, 1658 may be hexagonally shaped. It should be appreciated, however, that the recesses 1646, 1650, 1654, 1658 may have any shape and configuration adapted to non-rotatably couple and rigidly attach the connectors 1644, 1648, 1652, 1656 to respective drive shafts of the motor arrangement contained within the housing 1614. It should be appreciated that complementary projections may be provided on respective drive shafts of the motor arrangement to thereby drive the drive elements of the flexible shaft 1620. It should also be appreciated that the recesses may be provided on the drive shafts and complementary projections may be provided on the connectors 1644, 1648, 1652, 1656. Any other coupling arrangement configured to non-rotatably and releasably couple the connectors 1644, 1648, 1652, 1656 and the drive shafts of the motor arrangement may be provided.

One of the connectors 1644, 1648, 1652, 1656 is non-rotatably secured to the first drive shaft 94, and another one of the connectors 1644, 1648, 1652, 1656 is non-rotatably secured to the second drive shaft 102. The remaining two of the connectors 1644, 1648, 1652, 1656 engage with transmission elements configured to apply tensile forces on the steering cables 1634, 1635, 1636, 1637 to thereby steer the distal end 1624 of the flexible shaft 1620. The data transfer cable 1638 is electrically and logically connected with data connector 1660. The data connector 1660 includes, for example, electrical contacts 1662, corresponding to and equal in number to the number of individual wires contained in the data cable 1638. The first coupling 1622 includes a key structure 1642 configured to properly orient the first coupling 1622 to a mating and complementary coupling arrangement disposed on the housing 1612. The key structure 1642 may be provided on either one, or both, of the first coupling 1622 and the mating and complementary coupling arrangement disposed on the housing 1612. The first coupling 1622 may include a quick-connect type connector, which may engage the first coupling 1622 to the housing 1612 by a simple pushing motion. Seals may be provided in conjunction with any of the several connectors 1644, 1648, 1652, 1656, 1660 to provide a fluid-tight seal between the interior of first coupling 1622 and the environment.

Figure 10:
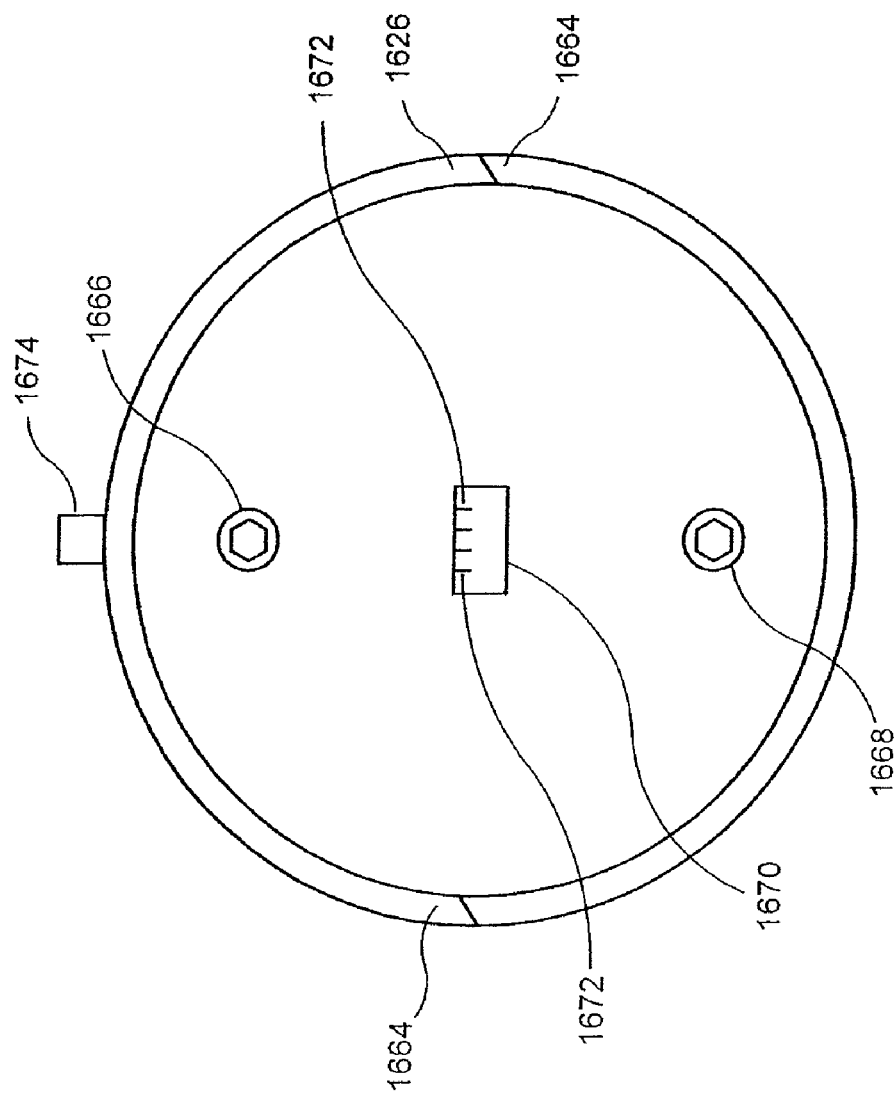
FIG. 10, there is seen a front end view of the second coupling of the flexible shaft, according to an example embodiment of the present invention.

Referring now to FIG. 10, there is seen a front end view of the second coupling 1626 of the flexible shaft 1620. In the example embodiment, the second coupling 1626 includes a first connector 1666 and a second connector 1668, each rotatably secured to the second coupling 1626 and each non-rotatably secured to a distal end of a respective one of the first and second drive shafts 94, 102. A quick-connect type fitting 1664 is provided on the second coupling 1626 to detachably secure the device 11 thereto. The quick-connect type fitting 1664 may be, for example, a rotary quick-connect type fitting, a bayonet type fitting, etc. and may be a fitting complementary to the quick connect sleeve 713 illustrated in FIG. 2(b). A key structure 1674 may be provided on the second coupling 1626 and may be configured to properly align the surgical device 11 to the second coupling 1626. The key structure or other arrangement configured to properly align the surgical device 11 to the flexible shaft 1620 may be provided on either one, or both, of the second coupling 1626 and the surgical device 11. In addition, the key structure may be provided on the device 11, as illustrated in FIG. 2(b) as the slots 713a of the quick connect sleeve 713. A data connector 1670 having electrical contacts 1672 is also provided in the second coupling 1626. Like the data connector 1660 of first coupling 1622, the data connector 1670 of the second coupling 1626 includes contacts 1672 electrically and logically connected to the respective wires of the data transfer cable 1638 and the contacts 1662 of the data connector 1660. Seals may be provided in conjunction with the connectors 1666, 1668, 1670 to provide a fluid-tight seal between the interior of the second coupling 1626 and the environment.

Disposed within the housing 1614 of the remote power console 1612 are electro-mechanical driver elements configured to drive the drive shafts 94, 102 and the steering cables 1634, 1635, 1636, 1637 to thereby operate the electro-mechanical driver component 1610 and the surgical device 11 attached to the second coupling 1626. In the example embodiment illustrated schematically in FIG. 19, five electric motors 96, 100, 1684, 1690, 1696, each operated via a power source, may be disposed in the remote power console 1612. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 11:
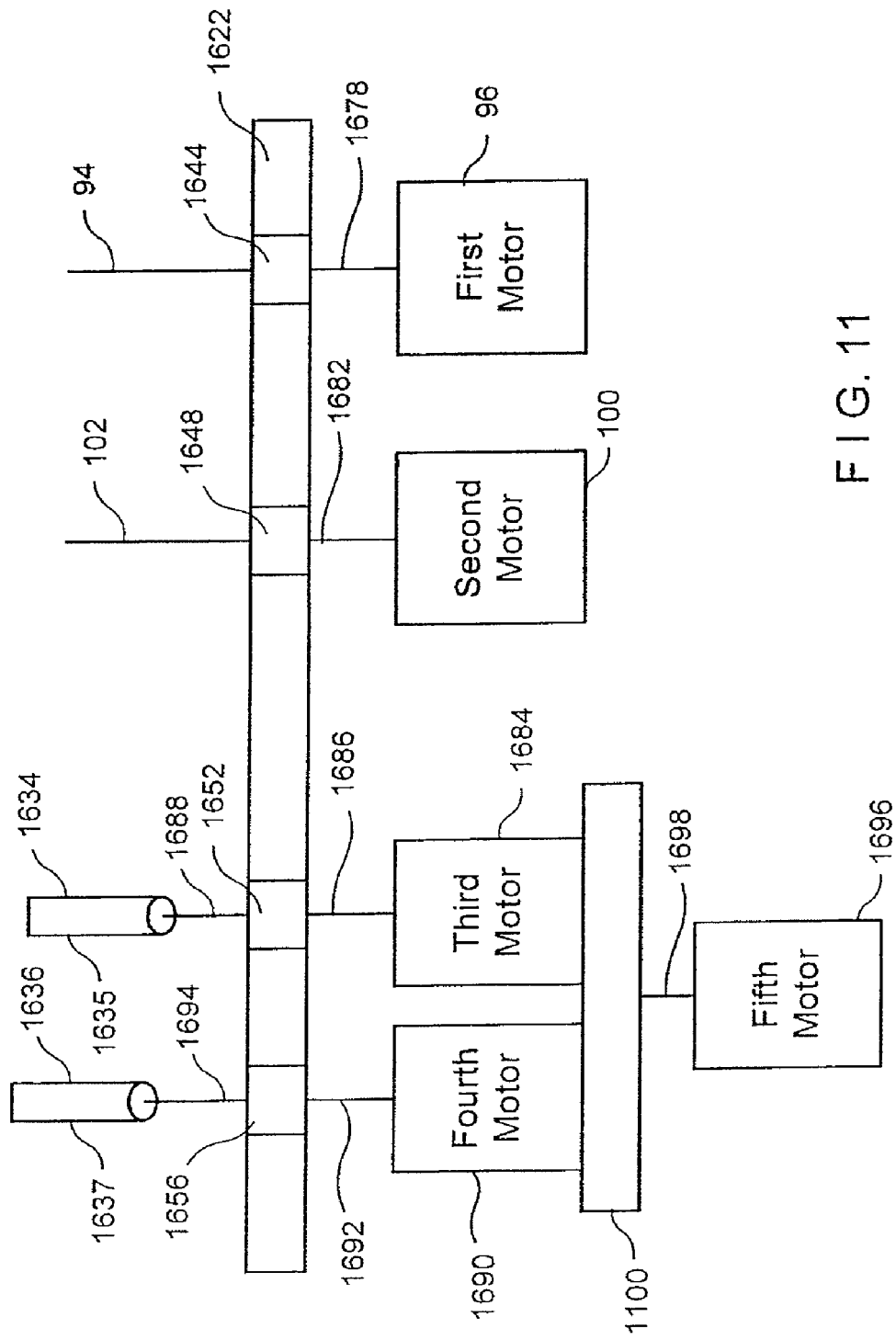
FIG. 11 illustrates schematically an arrangement of motors, according to an example embodiment of the present invention.

FIG. 11 illustrates schematically one possible arrangement of motors. An output shaft 1678 of a first motor 96 engages with the first connector 1644 of the first coupling 1622 when the first coupling 1622, and, therefore, the flexible shaft 1620, is engaged with the housing 1614 to thereby drive the first drive shaft 94 and the first connector 1666 of the second coupling 1626. Similarly, an output shaft 1682 of a second motor 100 engages the second connector 1648 of the first coupling 1622 when the first coupling 1622, and, therefore, flexible shaft 1620 is engaged with the housing 1614 to thereby drive the second drive shaft 102 and the second connector 1668 of the second coupling 1626. An output shaft 1686 of a third motor 1684 engages the third connector 1652 of the first coupling 1622 when the first coupling 1622, and, therefore, the flexible shaft 1620, is engaged with the housing 1614 to thereby drive the first and second steering cables 1634, 1635 via a first pulley arrangement 1688. An output shaft 1692 of a fourth motor 1690 engages the fourth connector 1656 of the first coupling 1622 when the first coupling 1622, and, therefore, the flexible shaft 1620, is engaged with the housing 1614 to thereby drive the third and fourth steering cables 1636, 1637 via a second pulley arrangement 1694. The third and fourth motors 1684, 1690 may be secured on a carriage 1100, which is selectively movable via an output shaft 1698 of a fifth motor 1696 between a first position and a second position to selectively engage and disengage the third and fourth motors 1684, 1690 with the respective pulley arrangement 1688, 1694 to thereby permit the flexible shaft 1620 to become taut and steerable or limp as necessary. It should be appreciated that other mechanical, electrical and/or electro-mechanical mechanisms, etc., may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," which is expressly incorporated herein in its entirety by reference thereto. It should also be appreciated that, in accordance with other embodiments of the present invention, the steering mechanism may not be present at all, the surgical device 11 providing articulation between the jaw portion 11a and the shaft portion 11b so as to maneuver the surgical device 11 within a surgical site.

It should be appreciated that any one or more of the motors 96, 100, 1684, 1690, 1696 may be, for example, a high-speed/low-torque motor, a low-speed/high-torque motor, etc. As indicated above, the first rotatable drive shaft 94 and the second rotatable drive shaft 102 may be configured to transmit high speed and low torque. Thus, the first motor 96 and the second motor 100 may be configured as high-speed/low-torque motors. Alternatively, the first motor 96 and the second motor 100 may be configured as low-speed/high-torque motors with a torque-reducing/speed-increasing gear arrangement disposed between the first motor 96 and the second motor 100 and a respective one of the first rotatable drive shaft 94 and the second rotatable drive shaft 102. Such torque-reducing/speed-increasing gear arrangements may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 1612 or in the proximal end of the flexible shaft 1620, such as, for example, in the first coupling 1622. It should be appreciated that the gear arrangement(s) may be provided at the distal and/or proximal ends of the first rotatable drive shaft 94 and/or the second rotatable drive shaft 102 to prevent windup and breakage thereof.

Figure 12:
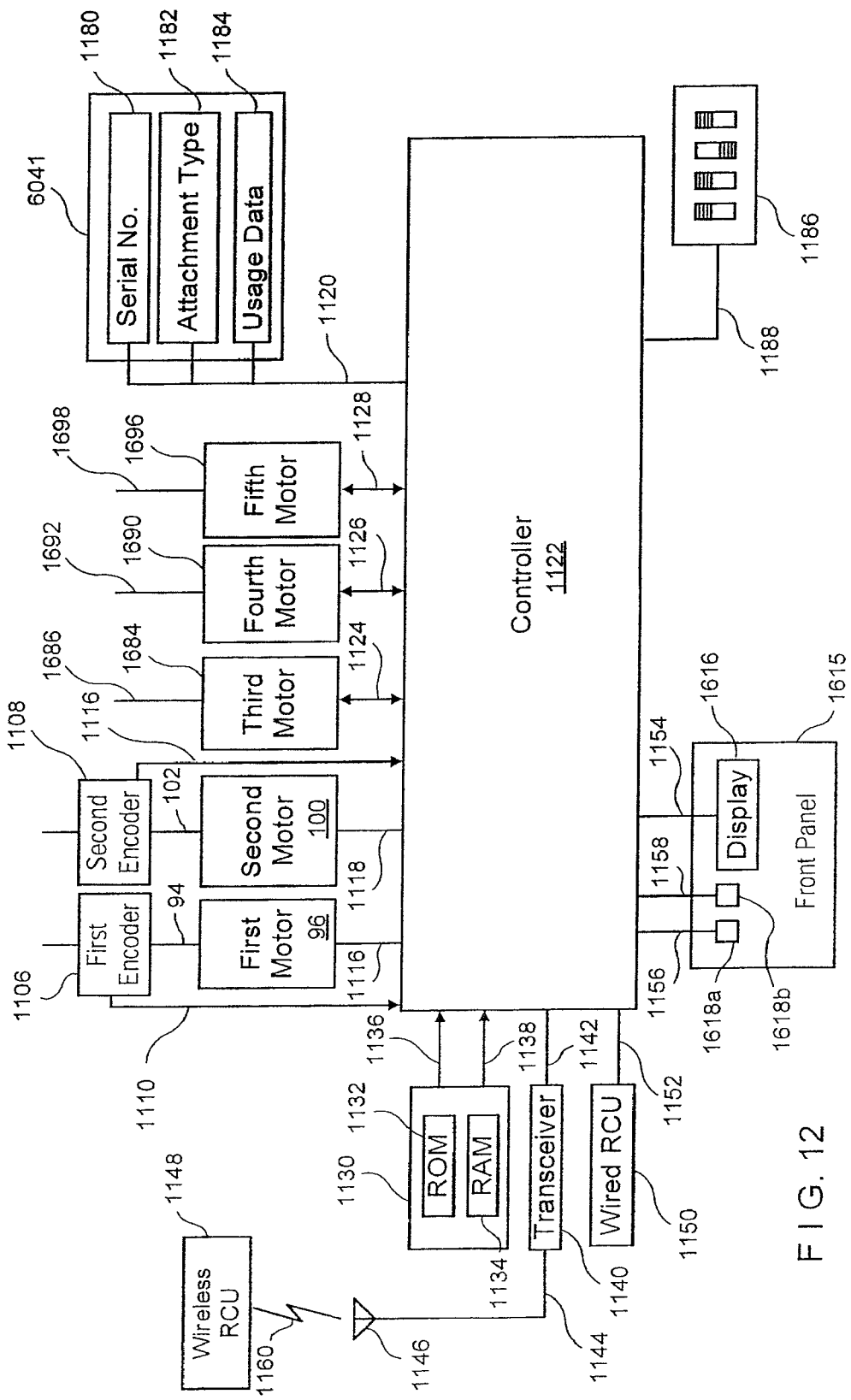
FIG. 12 illustrates a schematic view of the electro-mechanical driver component, according to an example embodiment of the present invention.

Referring now to FIG. 12, there is seen a schematic view of the electro-mechanical driver component 1610. A controller 1122 is provided in the housing 1614 of remote power console 1612 and is configured to control all functions and operations of the electro-mechanical driver component 1610 and the linear clamping, cutting and stapling device 11 or other surgical instrument or attachment attached to the flexible shaft 1620. A memory unit 1130 is provided and may include memory devices, such as, a ROM component 1132, a RAM component 1134, etc. The ROM component 1132 is in electrical and logical communication with the controller 1122 via a line 1136, and the RAM component 1134 is in electrical and logical communication with controller 1122 via line 1138. The RAM component 1134 may include any type of random-access memory, such as, for example, a magnetic memory device, an optical memory device, a magneto-optical memory device, an electronic memory device, etc. Similarly, the ROM component 1132 may include any type of read-only memory, such as, for example, a removable memory device, such as a PC-Card or PCMCIA-type device. It should be appreciated that the ROM component 1132 and the RAM component 1134 may be configured as a single unit or may be separate units and that the ROM component 1132 and/or the RAM component 1134 may be provided in the form of a PC-Card or PCMCIA-type device.

The controller 1122 is further connected to the front panel 1615 of the housing 1614 and, more particularly, to the display device 1616 via a line 1154 and the indicators 1618*a*, 1618*b* via respective lines 1156, 1158. The lines 1116, 1118, 1124, 1126, 1128 electrically and logically connect controller 1122 to first, second, third, fourth and fifth motors 96, 100, 1684, 1690, 1696, respectively. A wired remote control unit ("RCU") 1150 is electrically and logically connected to the controller 1122 via a line 1152. A wireless RCU 1148 is also provided and communicates via a wireless link 1160 with a receiving/sending unit 1146 connected via a line 1144 to a transceiver 1140. The transceiver 1140 is electrically and logically connected to the controller 1122 via a line 1142. The wireless link 1160 may be, for example, an optical link, such as an infrared link, a radio link or any other form of wireless communication link.

A switch device 1186, which may include, for example, an array of DIP switches, may be connected to the controller 1122 via a line 1188. The switch device 1186 may be configured, for example, to select one of a plurality of languages used in displaying messages and prompts on the display device 1616. The messages and prompts may relate to, for example, the operation and/or the status of the electro-mechanical driver component 1610 and/or to the surgical device 11 attached thereto.

According to the example embodiment of the present invention, a first encoder 1106 is provided within the second coupling 1626 and is configured to output a signal in response to and in accordance with the rotation of the first drive shaft 94. A second encoder 1108 is also provided within the second coupling 626 and is configured to output a signal in response to and in accordance with the rotation of the second drive shaft 102. The signal output by each of the encoders 1106, 1108 may represent the rotational position of the respective drive shaft 94, 102 as well as the rotational direction thereof. These encodes may be an arrangement of light sources, e.g., LEDs, and optical fibers as illustrated for instance in FIG. 6(*e*). Alternatively, such encoders 1106, 1108 may include, for example, Hall-effect devices, optical devices, etc. Although the encoders 1106, 1108 are described as being disposed within the second coupling 1626, it should be appreciated that the encoders 1106, 1108 may be provided at any location between the motor system and the surgical device 11. It should be appreciated that providing the encoders 1106, 1108 within the second coupling 1626 or at the distal end of the flexible shaft 1620 may provide an accurate determination of the drive shaft rotation. If the encoders 1106, 1108 are disposed at the proximal end of the flexible shaft 1620, windup of the first and second rotatable drive shafts 94, 102 may result in measurement error.

Figure 13:
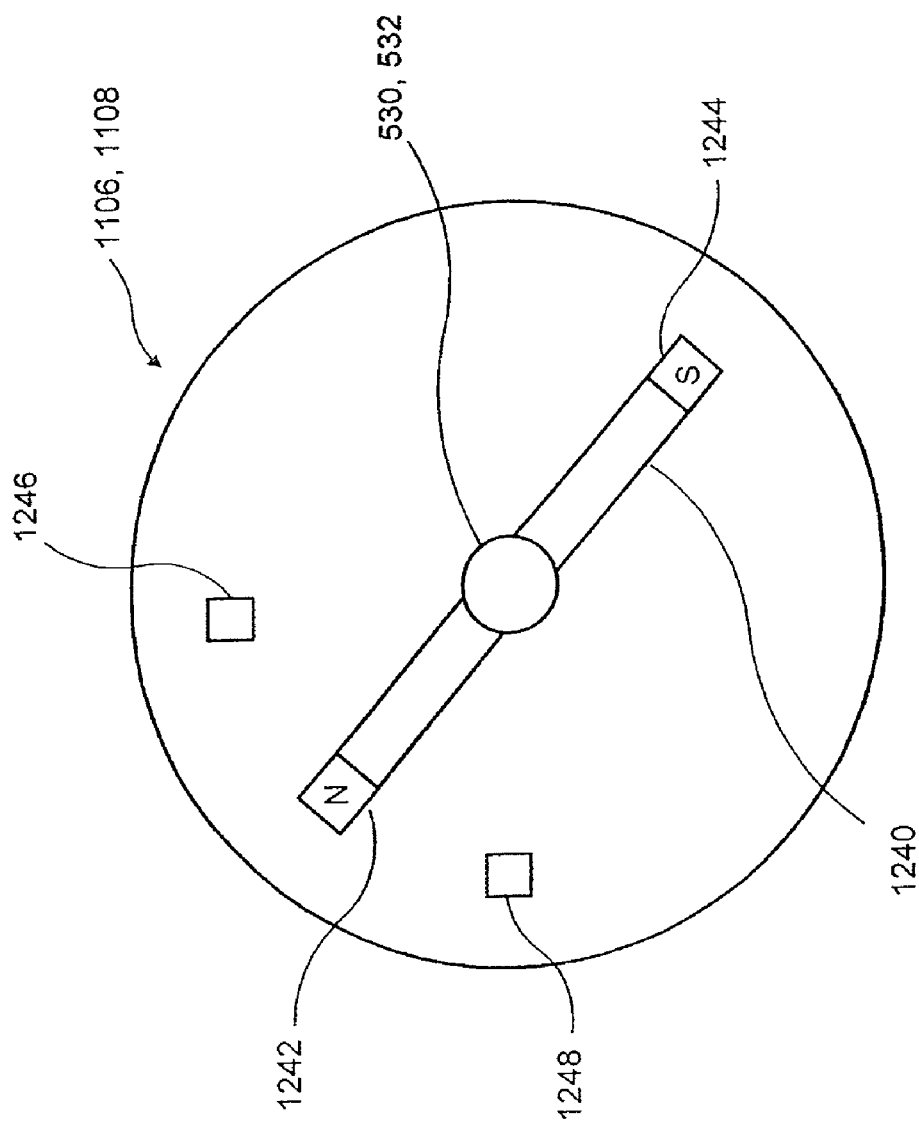
FIG. 13 is a schematic view of an encoder, according to an example embodiment of the present invention.

FIG. 13 is a schematic view of an encoder 1106, 1108, which includes a Hall-effect device. Mounted non-rotatably on the drive shaft 94, 102 is a magnet 1240 having a north pole 1242 and a south pole 1244. The encoder 1106, 1108 further includes a first sensor 1246 and second sensor 1248, which are disposed approximately 90° apart relative to the longitudinal, or rotational, axis of the drive shaft 94, 102. The output of the sensors 1246, 1248 is persistent and changes its state as a function of a change of polarity of the magnetic field in the detection range of the sensor. Thus, based on the output signal from the encoders 1106, 1108, the angular position of the drive shaft 94, 102 may be determined within one-quarter revolution and the direction of rotation of the drive shaft 94, 102 may be determined. The output of each encoder 1106, 1108 is transmitted via a respective line 1110, 1112 of data transfer cable 1638 to controller 1122. The controller 1122, by tracking the angular position and rotational direction of the drive shafts 94, 102 based on the output signal from the encoders 1106, 1108, may thereby determine the position and/or state of the components of the surgical device connected to the electro-mechanical driver component 1610. That is, by counting the revolutions of the drive shaft 94, 102, the controller 1122 may determine the position and/or state of the components of the surgical device connected to the electro-mechanical driver component 1610.

For example, the advancement distance of the first jaw 50 relative to the second jaw 80 and of the wedge 603 may be functions of, and ascertainable on the basis of, the rotation of the respective drive shafts 94, 102. By ascertaining an absolute position of the first jaw 50 and the wedge 603 at a point in time, the relative displacement of the first jaw 50 and the wedge 603, based on the output signal from the encoders 1106, 1108 and the known pitches of the threaded screw 520 and of the wedge driver 605, may be used to ascertain the absolute position of the first jaw 50 and the wedge 603 at all times thereafter. The absolute position of the first jaw 50 and the wedge 603 may be fixed and ascertained at the time that the surgical device 11 is first coupled to the flexible shaft 1620. Alternatively, the position of the first jaw 50 and the wedge 603 relative to, for example, the second jaw 80 may be determined based on the output signal from the encoders 1106, 1108.

As discussed above in connection with FIGS. 2(*b*) and 10, the surgical device 11 may include a data connector 1272 adapted by size and configuration to electrically and logically connect to connector 1670 of second coupling 1626. In the example embodiment, the data connector 1272 includes contacts 1276 equal in number to the number of contacts 1672 of connector 1670. The memory module 6041 is electrically and logically connected with the data connector 1272. Memory module 6041 may be in the form of, for example, an EEPROM, EPROM, etc. and may be contained, for example, within the staple tray 604 of the replaceable staple cartridge 600 in the second jaw 80 of the surgical device 11, as illustrated in FIG. 3(*f*).

Figure 14:
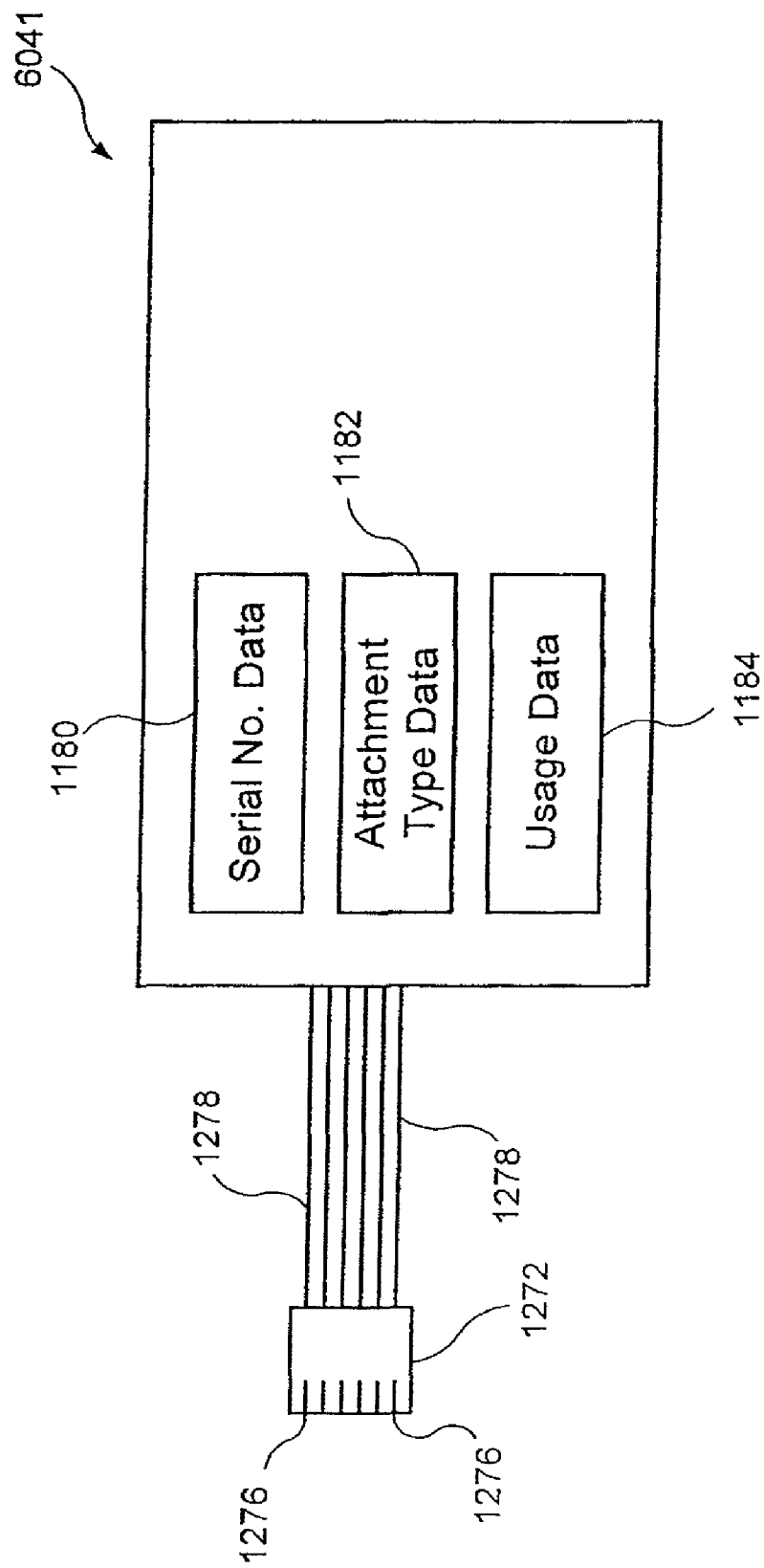
FIG. 14 schematically illustrates the memory module, according to an example embodiment of the present invention.

FIG. 14 schematically illustrates the memory module 6041. As seen in FIG. 14, data connector 1272 includes contacts 1276, each electrically and logically connected to the memory module 6041 via a respective line, e.g., flexible data cable 1278. The memory module 6041 may be configured to store, for example, a serial number data 1180, an attachment type identifier (ID) data 1182 and a usage data 1184. The memory module 6041 may additionally store other data. Both the serial number data 1180 and the ID data 1182 may be configured as read-only data. The serial number data 1180 and/or the ID data 1182 may be stored in a read-only section of the memory module 6041. In the example embodiment, serial number data 1180 may be data uniquely identifying the particular surgical device, whereas the ID data 1182 may be data identifying the type of the attachment, such as, e.g., for an electro-mechanical driver component 1610 to which other types of surgical instruments or attachments are attachable. The usage data 1184 represents usage of the particular attachment, such as, for example, the number of times the first jaw 50 of the surgical device 11 has been opened and closed, or the number of times that the wedge 603 of the surgical device 11 has been advanced. The usage data 1184 may be stored in a read/write section of the memory module 6041.

It should be appreciated that the attachment attachable to the distal end 1624 of the flexible shaft 1620, e.g., surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 12, the controller 1122 is configured to read the ID data 1182 from the memory module 6041 of the surgical device 11 when the surgical device 11 is initially connected to the flexible shaft 1620. The memory module 6041 is electrically and logically connected to the controller 1122 via the line 1120 of the data transfer cable 1638. Based on the read ID data 1182, the controller 1122 is configured to read or select from the memory unit 1130, an operating program or algorithm corresponding to the type of surgical instrument or attachment connected to the flexible shaft 1620. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory module 6041 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical driver component 1610. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory module 6041 of the surgical device 11 and transferred to the controller 1122 via the data transfer cable 1638. Once the appropriate operating program or algorithm is read by or selected by or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 96, 100, 1684, 1690, 1696 via respective lines 1116, 1118, 1124, 1126, 1128 and is configured to control such motors 96, 100, 1684, 1690, 1696 in accordance with the read, selected or transmitted operating program or algorithm via the respective lines 1116, 1118, 1124, 1126, 1128.

Figure 15:
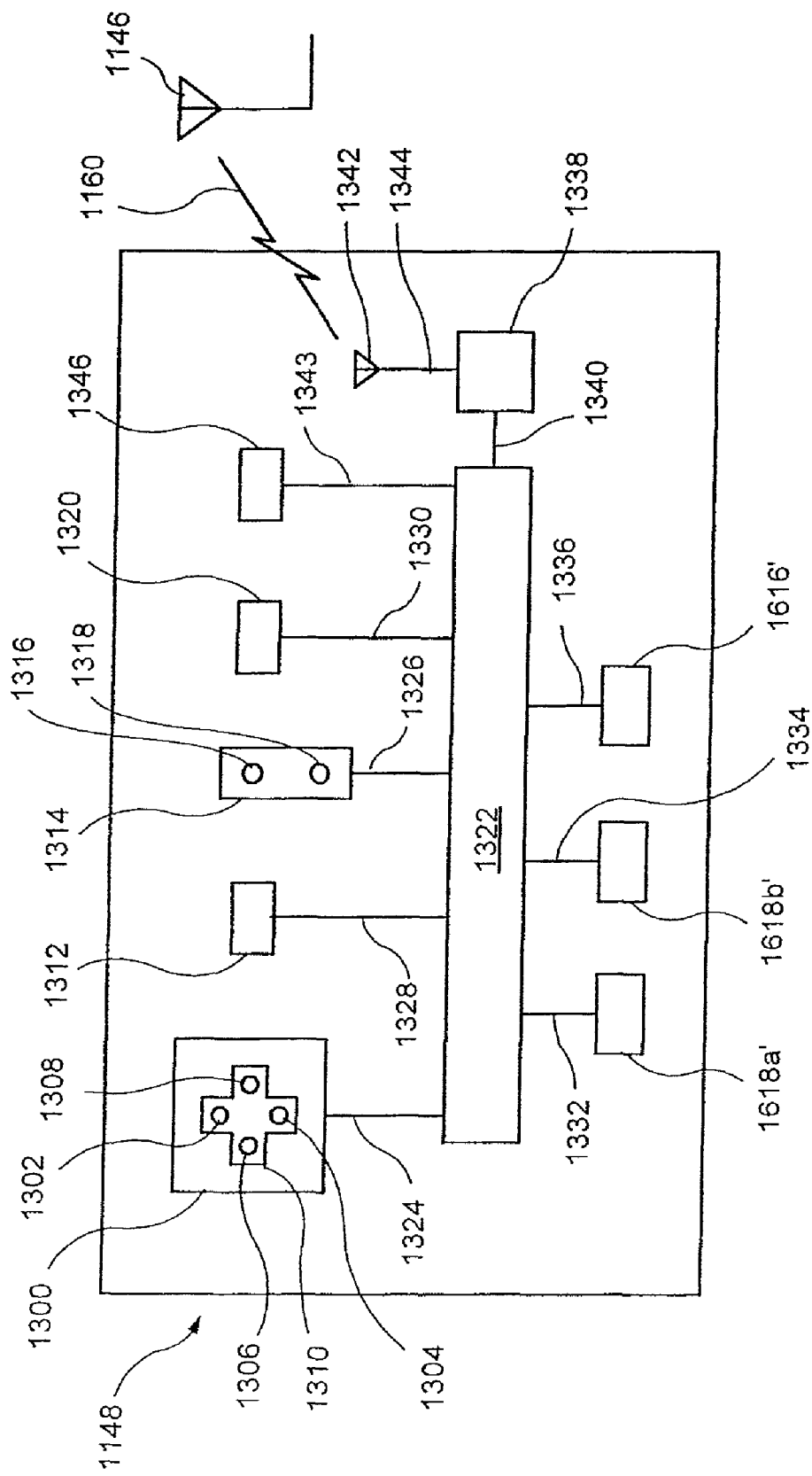
FIG. 15, there is seen a schematic view of a wireless RCU, according to an example embodiment of the present invention.

Referring now to FIG. 15, there is seen a schematic view of wireless RCU 1148. Wireless RCU 1148 includes a steering controller 1300 having a plurality of switches 1302, 1304, 1306, 1308 arranged under a four-way rocker 1310. The operation of switches 1302, 1304, via rocker 1310, controls the operation of first and second steering cables 1634, 1635 via third motor 1684. Similarly, the operation of switches 1306, 1308, via rocker 1310, controls the operation of third and fourth steering cables 1636, 1637 via fourth motor 1692. It should be appreciated that rocker 1310 and switches 1302, 1304, 1306, 1308 are arranged so that the operation of switches 1302, 1304 steers the flexible shaft 1620 in the north-south direction and that the operation of switches 1306, 1308 steers the flexible shaft 1620 in the east-west direction. Reference herein to north, south, east and west is made to a relative coordinate system. Alternatively, a digital joystick, an analog joystick, etc. may be provided in place of rocker 1310 and switches 1302, 1304, 1306, 1308. Potentiometers or any other type of actuator may also be used in place of switches 1302, 1304, 1306, 1308.

The wireless RCU 1148 further includes a steering engage/disengage switch 1312, the operation of which controls the operation of fifth motor 696 to selectively engage and disengage the steering mechanism. The wireless RCU 1148 also includes a two-way rocker 1314 having first and second switches 1316, 1318 operable thereby. The operation of these switches 1316, 1318 controls certain functions of the electro-mechanical driver component 1610 and any surgical instrument or attachment, such as the surgical device 11, attached to the flexible shaft 1620 in accordance with the operating program or algorithm corresponding to the attached device. For example, operation of the two-way rocker 1314 may control the opening and closing of the first jaw 50 and the second jaw 80 of the surgical device 11. The wireless RCU 1148 is provided with yet another switch 1320, the operation of which may further control the operation of the electro-mechanical driver component 1610 and the device attached to the flexible shaft 1620 in accordance with the operating program or algorithm corresponding to the attached device. For example, operation of the switch 1320 may initiate the advancement of the wedge 603 of the surgical device 11.

The wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. The wireless RCU 1148 may include indicators 1618a', 1618b', corresponding to the indicators 1618a, 1618b of front panel 1615, and a display device 1616', corresponding to the display device 1616 of the front panel 1615. If provided, the indicators 1618a', 1618b' are electrically and logically connected to controller 1322 via respective lines 1332, 1334, and the display device 1616' is electrically and logically connected to controller 1322 via line 1336. The controller 1322 is electrically and logically connected to a transceiver 1338 via line 1340, and the transceiver 1338 is electrically and logically connected to a receiver/transmitter 1342 via line 1344. A power supply, for example, a battery, may be provided in wireless RCU 1148 to power the same. Thus, the wireless RCU 1148 may be used to control the operation of the electro-mechanical driver component 1610 and the device 11 attached to the flexible shaft 1620 via wireless link 1160.

The wireless RCU 1148 may include a switch 1346 connected to a controller 1322 via line 1348. Operation of the switch 1346 transmits a data signal to the transmitter/receiver 1146 via wireless link 1160. The data signal includes identification data uniquely identifying the wireless RCU 1148. This identification data is used by the controller 1122 to prevent unauthorized operation of the electro-mechanical driver component 1610 and to prevent interference with the operation of the electro-mechanical driver component 610 by another wireless RCU. Each subsequent communication between the wireless RCU 1148 and the electro-mechanical device surgical 610 may include the identification data. Thus, the controller 1122 may discriminate between wireless RCUs and thereby allow only a single, identifiable wireless RCU 1148 to control the operation of the electro-mechanical driver component 1610 and the surgical device 11 attached to the flexible shaft 1620.

Based on the positions of the components of the surgical device attached to the flexible shaft 1620, as determined in accordance with the output signals from the encoders 1106, 1108, the controller 1122 may selectively enable or disable the functions of the electro-mechanical driver component 1610 as defined by the operating program or algorithm corresponding to the attached device. For example, for the surgical device 11, the firing function controlled by the operation of the switch 1320 may be disabled unless the space or gap between the first jaw 50 and the second jaw 80 is determined to be within an acceptable range.

Figure 16:
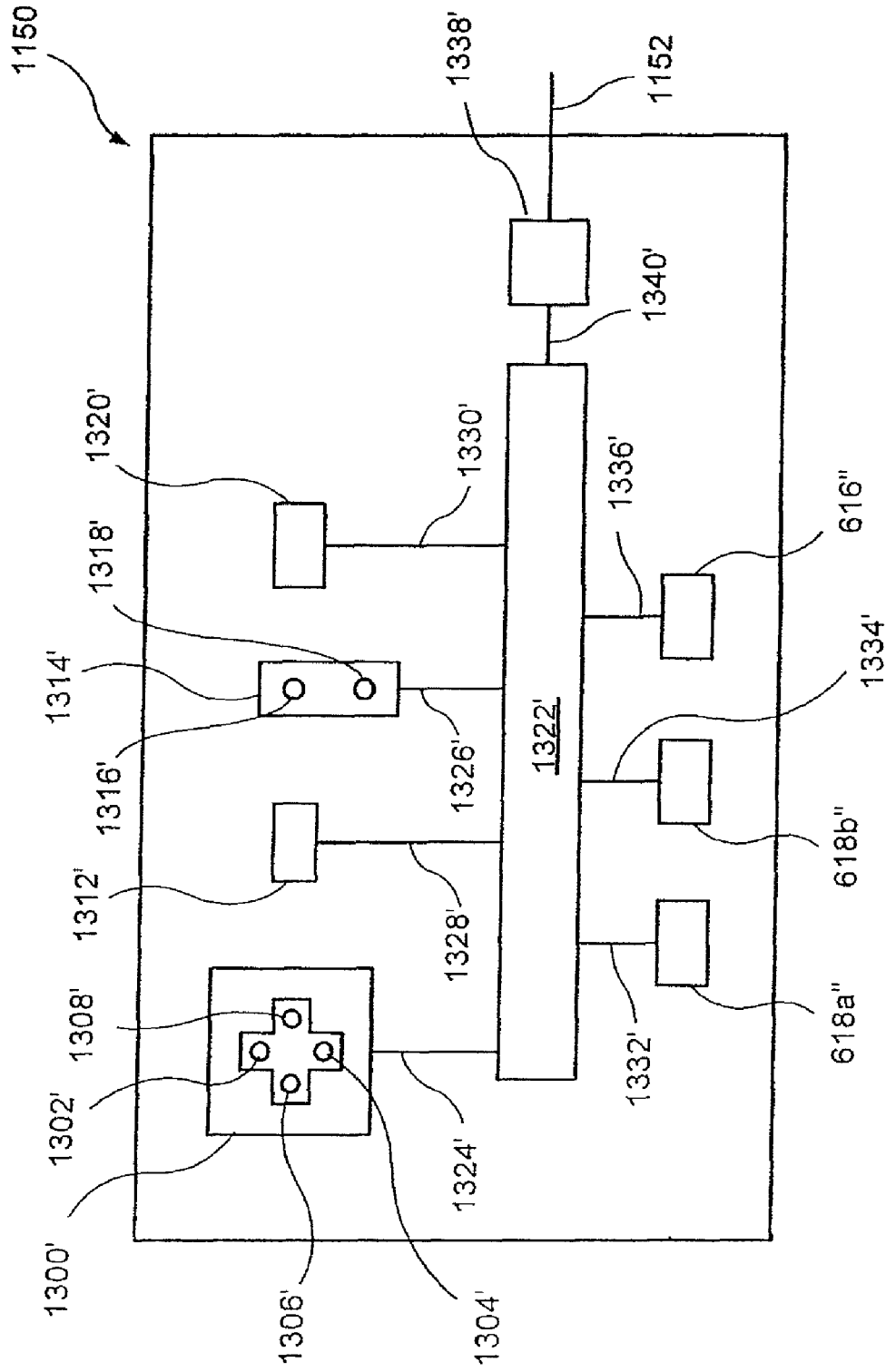
FIG. 16, there is seen a schematic view of a wired RCU, according to an example embodiment of the present invention.

Referring now to FIG. 16, there is seen a schematic view of a wired RCU 1150. In the example embodiment, wired RCU 1150 includes substantially the same control elements as the wireless RCU 1148 and further description of such elements is omitted. Like elements are indicated in FIG. 16 with an accompanying prime. It should be appreciated that the functions of the electro-mechanical driver component 1610 and the device attached to the flexible shaft 1620, e.g., the surgical device 11, may be controlled by the wired RCU 1150 and/or by the wireless RCU 1148. In the event of a battery failure, for example, in the wireless RCU 1148, the wired RCU 1150 may be used to control the functions of the electro-mechanical driver component 1610 and the device attached to the flexible shaft 1620.

As described hereinabove, the front panel 1615 of the housing 1614 includes the display device 1616 and the indicators 1618a, 1618b. The display device 1616 may include an alpha-numeric display device, such as an LCD display device. The display device 1616 may also include an audio output device, such as a speaker, a buzzer, etc. The display device 1616 is operated and controlled by controller 1122 in accordance with the operating program or algorithm corresponding to the device attached to the flexible shaft 1620, e.g., the surgical device 11. If no surgical instrument or attachment is so attached, a default operating program or algorithm may be read by or selected by or transmitted to controller 1122 to thereby control the operation of the display device 1616 as well as the other aspects and functions of the electro-mechanical driver component 1610. If the surgical device 11 is attached to the flexible shaft 1620, the display device 1616 may display, for example, data indicative of the gap between the first jaw 50 and the second jaw 80 as determined in accordance with the output signal of encoders 1106, 1108, as more fully described hereinabove.

Similarly, the indicators 1618a, 1618b are operated and controlled by the controller 1122 in accordance with the operating program or algorithm corresponding to the device attached to the flexible shaft 1620, e.g., the surgical device 11. The indicator 1618a and/or the indicator 1618b may include an audio output device, such as a speaker, a buzzer, etc., and/or a visual indicator device, such as an LED, a lamp, a light, etc. If the surgical device 11 is attached to the flexible shaft 1620, the indicator 1618a may indicate, for example, that the electro-mechanical driver component 1610 is in a power ON state, and the indicator 618b may, for example, indicate whether the gap between the first jaw 50 and the second jaw 80 is determined to be within the acceptable range. It should be appreciated that although two indicators 1618a, 1618b are described, any number of additional indicators may be provided as necessary. Additionally, it should be appreciated that although a single display device 1616 is described, any number of additional display devices may be provided as necessary.

The display device 1616' and the indicators 1618a', 1618b' of wired RCU 1150 and the display device 1616" and indicators 1618a", 1618b" of the wireless RCU 1148 are similarly operated and controlled by respective controller 1322, 1322' in accordance with the operating program or algorithm of the device attached to the flexible shaft 1620.

As set forth above, one problem with conventional surgical devices, and in particular with the conventional linear clamping, cutting and stapling devices such as that illustrated in FIG. 1, is that the opposing jaws may be difficult to maneuver within a patient. It may be necessary for a surgeon to move the opposing jaws between various angles in order to position the desired tissue between the opposing jaws. However, it may also be desirable to make an incision in a patient that is as small as possible, and the small size of an incision limits the degree to which the opposing jaws may be maneuvered. Example embodiments of the present invention may provide improved maneuverability of a surgical device, e.g., the surgical device 11, within a patient.

Another problem with the conventional surgical devices, and in particular with the foregoing linear clamping, cutting and stapling devices such as that illustrated in FIG. 1, is that the opposing jaws may not be sufficiently hemostatic. Specifically, the opposing jaws of the foregoing surgical devices may not be clamped together with sufficient force, thereby reducing the effectiveness of the surgical device. Example embodiments of the present invention may provide improved clamping of a section of tissue disposed between the jaws of a surgical device, e.g., the surgical device 11, thereby providing a sufficiently hemostatic condition with respect to the clamped section of tissue.

Furthermore, and as previously mentioned, one problem of conventional cutting and stapling devices is that the opposing jaws of the mechanism may not adequately clamp a section of tissue clamped therebetween, and they may not prevent a section of tissue clamped therebetween from escaping out from between the distal ends of the jaws during the operation of the device. This follows because the scissor-type gripping elements of conventional clamping, cutting and stapling devices, such as the device illustrated in FIG. 1, pivot relative to each other around a fixed pivot point at a proximal end of the gripping elements. Thus, since the distance between the gripping elements is always less at a proximal end of the gripping elements than at the distal ends of the gripping elements, the clamping force on a section of tissue disposed between the gripping elements is greatest near the proximal ends of the gripping elements and gradually decreases in the distal direction. The relatively high clamping force at the proximal ends of the gripping elements coupled with the relatively low clamping force at the distal ends of the gripping elements causes the section of tissue to be pushed towards, and eventually out from between, the distal ends of the gripping elements. Thus, the section of tissue may not be adequately cut and stapled, and the inadequately cut and stapled end of the tissue may permit its contents to spill into the open abdomen of the patient, increasing the likelihood of infection and other complications.

In contrast, and as previously described in detail in connection with FIGS. 3(i) to 3(l), the surgical device 11 may provide an arrangement in which the distal ends 50a, 80a of the first and second jaws 50, 80 are urged towards each other during the operation of the surgical device 11, such that the clamping force between the distal ends 50a, 80a of the first and second jaws 50, 80 is greater in the surgical device 11 than the clamping force between the distal ends of the jaws of a conventional clamping, cutting and stapling device. The increased clamping force at the distal ends 50a, 80a of the first and second jaws 50, 80 may prevent a section of tissue which is disposed between the first and second jaws 50, 80 from escaping out from between the distal ends 50a, 80a of the first and second jaws 50, 80.

Figure 17:
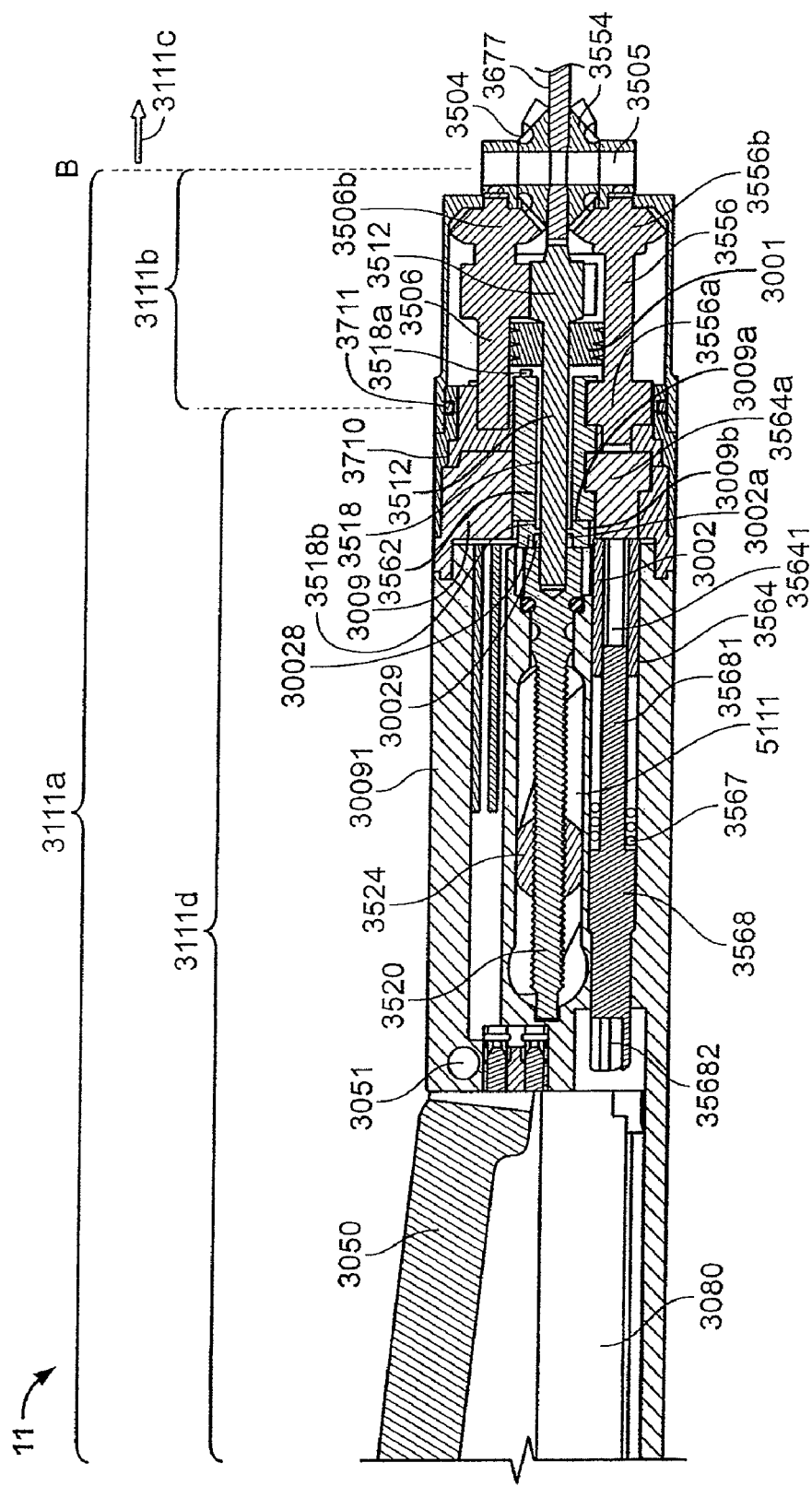
FIG. 17 is a side cross-sectional view of a surgical device, according to an example embodiment of the present invention.
Figure 18:
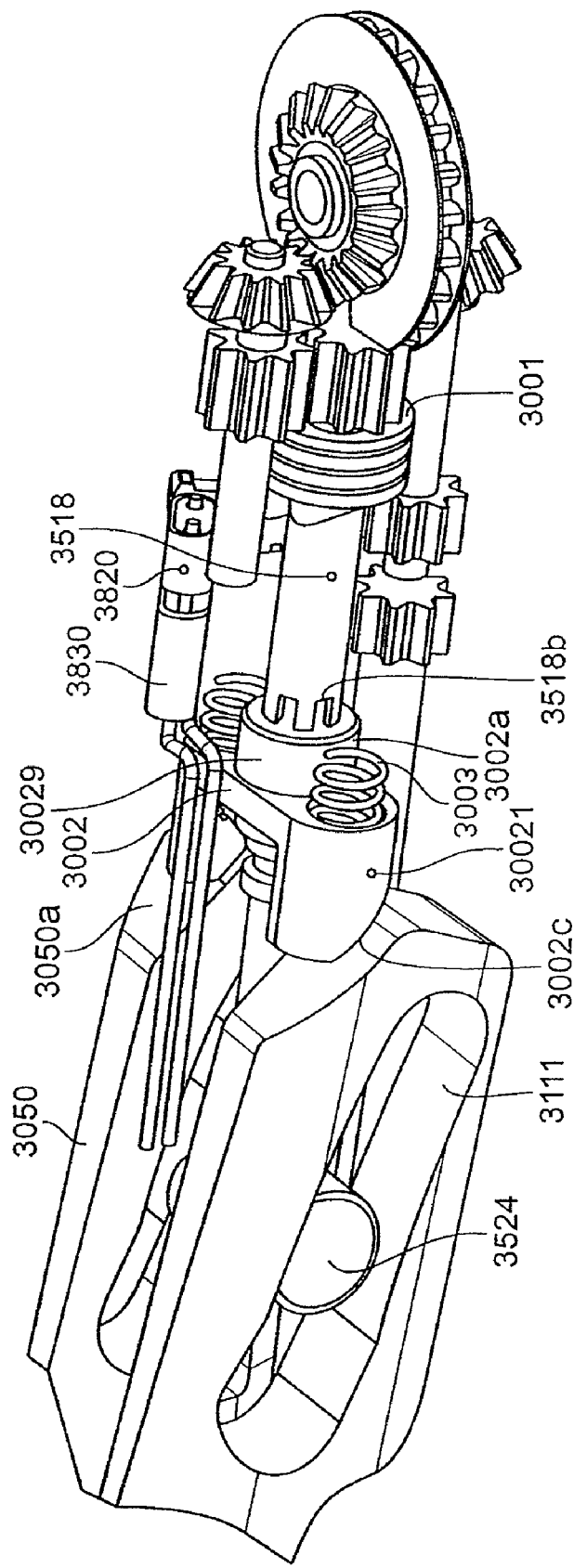
FIG. 18 is a perspective view of some of the internals components of the surgical device of FIG. 17.
Figure 19:
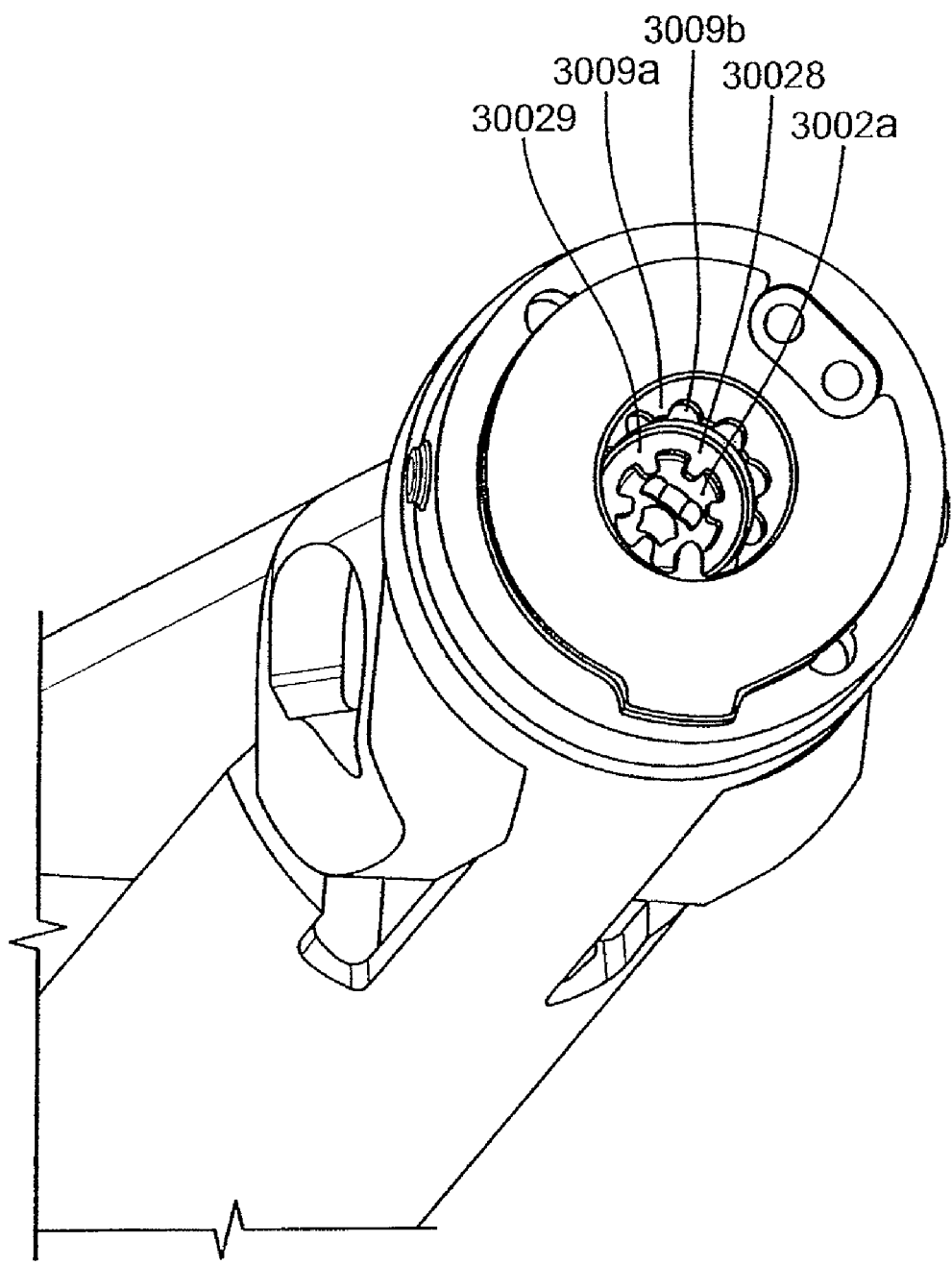
FIG. 19 is rear perspective view of some of the internals components of the surgical device of FIG. 17.

As set forth above, FIGS. 17 to 19 illustrate another embodiment of the present invention. Like the previously described embodiment, the embodiment illustrated in FIGS. 17 to 19 illustrate an arrangement in which two rotatable drive shafts may be employed to selectively move a jaw portion relative to a shaft portion, to rotate the jaw portion about its longitudinal axis, to move a first, e.g., upper, jaw relative to a second, e.g., lower, jaw, and to fire a stapling and cutting cartridge. This particular embodiment provides an arrangement in which a position of the first and second jaws relative to each other engages and disengages a gear element so as to selectively rotate the jaw portion, or a portion thereof, about its longitudinal axis and to fire a stapling and cutting cartridge.

FIG. 17 is a side cross-sectional view that illustrates various features of this embodiment. In this embodiment, an arrangement is provided that is configured to move, e.g., articulate, a jaw portion 3111a relative to a shaft portion 3111c. In addition, the arrangement is configured to rotate at least a portion of the jaw portion 3111a about its longitudinal axis, and more specifically, in the embodiment shown, to rotate a distal portion 3111d of the jaw portion 3111a relative to a joint portion 3111b of the jaw portion 3111a. Still further, the arrangement is configured to move, e.g., open and close, an upper jaw 3050 relative to the lower jaw 3080, and to fire a stapling and cutting cartridge located in the lower jaw 3080.

Referring to FIG. 17, there is illustrated an upper bevel gear element 3504 that is rotatably mounted about a pin 3505, the central axis of which is coaxial with the pivot axis B around which the jaw portion 3111a pivots relative to the shaft portion 3111c. The gear element 3504 is meshingly engaged with a bevel gear element 3506b of a clamping gear shaft 3506 arranged longitudinally within the jaw portion 3111a. The clamping gear shaft 3506 also includes a spur gear element 3506a. The clamping gear shaft 3506, including the bevel and spur gear elements 3506a and 3506b, rotates within the joint portion 3111b about a longitudinal axis of the clamping gear shaft 3506. The spur gear element 3506a is meshingly engaged with a spur gear element 3512a of a gear shaft 3512. A proximal end of the gear shaft 3512 is rotatably mounted within a distal recess 36771 of an articulation gear 3677, while a distal end of the gear shaft 3512 engages a threaded clamping screw 3520 (additional details of which are set forth below). In this manner, the gear shaft 3512 is rotatably mounted within the joint portion 3111b and the distal portion 3111d of the jaw portion 3111a. The threaded clamping screw 3520 is arranged longitudinally and is rotatable about its longitudinal axis via engagement with the distal end of the gear shaft 3512.

Mounted on the threaded screw 3520 is an inner shaft 3524. Opposite lateral ends of the inner shaft 3524 are seated within respective slots 5111 on each side of the upper jaw 3050. The upper jaw 3050 is rotatably mounted to the jaw body housing 30091 about a pin 3051, which is distally located with respect to the slots 5111.

A keying tube 3518 is coaxially mounted about, and is longitudinally slideable relative to, the gear shaft 3512. The keying tube 3518 includes at its proximal end an endplate 3518a that engages the joint portion 3111b in a manner that prevents rotation of the keying tube 3518 relative to the joint portion 3111b. Spring washers 3001 engage a proximally-facing surface of the endplate 3518a so as to bias the keying tube 3518 distally. The keying tube 3518 includes a set of teeth 3518b at a distal end thereof. The teeth 3518b are selectively engageable with correspondingly-shaped recesses 3002a of a proximal member 30029 of a cam block 3002.

The cam block 3002 is non-rotatably mounted and axially movable within the distal portion 3111d of the jaw portion 3111a. A portion of the proximal member 30029 of the cam block 3002 extends proximally through a longitudinally-arranged bore of the jaw body housing 3009. Specifically, the cam block 3002 is moveable in an axial direction between a first position (the position illustrated in FIG. 17), in which the correspondingly-shaped recesses 3002a are not in engagement with the teeth 3518b, and a second position, in which the cam block 3002 is moved proximally relative to the first position and the correspondingly-shaped recesses 3002a are rotatably-locked in engagement with the teeth 3518b.

An idler gear 3562 is coaxially mounted about the keying tube 3518. A distal end of idler gear 3562 is selectively engageable with correspondingly-shaped recesses 3009b on a proximally-facing surface of the jaw body housing 3009, the correspondingly-shaped recesses 3009b being circumferentially arranged about a longitudinal bore through the jaw body housing 3009. Longitudinally moveable within the central bore of the jaw body housing 3009 is the proximal member 30029 of the cam block 3002. A proximal face 30028 of the cam block 3002 is thereby moveable longitudinally through the bore of the jaw body housing 3009 such that the distal face of idler gear 3562 is selectively engageable with, e.g., contacted by, the proximal face 30028 of the cam block 3002. A proximal face of the idler gear 3562 abuts a distal face of the endplate 3518a of the keying tube 3518, and is therefore biased distally by virtue of the distal biasing experienced by the keying tube 5318 by the spring washers 3001.

The idler gear 3562 is moveable in an axial direction between a first position and a second position. In the first position (the position illustrated in FIG. 17), the distal end of the idler gear 3562 is seated within the correspondingly-shaped recesses 3009b on the proximally-facing surface of the jaw body housing 3009 so as to be locked in non-rotatable engagement relative to the jaw body housing 3009. In addition, in this first position, the proximal face 30028 of the cam block 3002 is axially spaced apart from the distal face of the idler gear 3562.

In the second position, the cam block 3002 is moved proximally relative to the position shown in FIG. 17 such that the proximal face 30028 of the cam block 3002 engages, e.g., contacts and gradually pushes, the distal face of the idler gear 3562. In this manner, the biasing force of the spring washers 3001 is overcome and the idler gear 3562 is caused to move proximally. Proximal movement of the idler gear 3562 eventually causes the distal face of the idler gear 3562 to be moved out of engagement with the recesses 3009b of the jaw body housing 3009. Once the idler gear 3562 is fully out of engagement with the recesses 3009b of the jaw body housing 3009, the idler gear 3562 is rotatable about the keying tube 3518.

In addition, a lower bevel gear element 3554 is rotatable about the pin 3505. The lower bevel gear element 3554 is meshingly engaged with a bevel gear element 3556b of a gear shaft 3556 longitudinally arranged within the jaw portion 3111a. The gear shaft 3556 also includes a spur gear element 3556a. The gear shaft 3556, including the bevel and spur gear elements 3556a and 3556b, rotates within the joint portion 3111b about a longitudinal axis of the gear shaft 3556. The gear element 3556a is meshingly engaged with a proximal section of idler gear 3562.

Meshingly engaged to a distal section of idler gear 3562 is a gear element 3564a of a gear shaft 3564. The gear shaft 3564 is mounted within jaw portion 3111a and is rotatable about its longitudinal axis. A distal end of the gear shaft 3564 has a recess 35641 that has a cross-section that engages a correspondingly-shaped proximal end 35681 of a longitudinal rod 3568. The longitudinal rod 3568 has a shoulder 3568a. Between the gear shaft 3564 and the shoulder 3568a of the longitudinal rod 3568 is a spring 3567. The distal end 35682 of the longitudinal rod 3568 is configured to engage a respective opening in a wedge driver. The wedge driver rotates so as to drive a stapling/cutting wedge along a staple cartridge, such as described hereinabove.

The jaw body housing 3009 has, along a proximal portion of its outer circumference, a recess. A distal end of a seal sleeve 3710 fits over the recess, the seal sleeve 3710 having an outer circumferential surface at its distal end that is contiguous with the outer circumferential surface of the jaw body housing 3009. In addition, the seal sleeve 3710 has, along a proximal portion of its outer circumference, a recess. Arranged circumferentially around this recess is a groove into which an O-ring seal 3711 is positioned. A joint portion housing 3715 fits over the recess, the joint portion housing 3715 having an outer circumferential surface that is generally contiguous with the outer circumferential surface of the distal portion of the seal sleeve 3710. A distal portion of the joint portion housing 3715 maintains the O-ring seal 3711 within the groove of the seal sleeve 3710. The O-ring seal 3711 enables a seal to be maintained between the seal sleeve 3710, and the components arranged distally thereto, and the joint portion housing 3715 when these components are rotated relative to each other. In this manner, a jaw portion 3111a (or at least a portion thereof, e.g., a distal portion 3111d) is rotatable about its longitudinal axis.

Additional details of the cam block 3002 are shown in FIG. 18. Referring to FIG. 18, the cam block 3002 is, as set forth above, mounted so as to be axially movable within the distal portion 3111d of the jaw portion 3111a. As shown, the cam block 3002 includes a pair of arms 30021 that are disposed on laterally opposite sides relative to each other. Each one of the pair of arms 30021 includes a surface 3002c. The surfaces 3002c of the cam block 3002 engage respective cam surfaces 3050a of the upper jaw 3050 as the upper jaw 3050 is moved relative to the lower jaw 3080. As set forth above, the proximal member 30029 of the cam block 3002 extends proximally, e.g., through a central bore of the jaw body housing 3009 (hidden in this view). Each one of a pair of springs 3003 is located between a proximal-facing surface of the cam block 3002 and a distal-facing surface of the jaw body housing 3009 (hidden in this view) to bias the cam block 3002 distally. As set forth above, the cam block 3002 is longitudinally moveable between a first position (the position shown in FIG. 18), in which the correspondingly-shaped recesses 3002a are not in engagement with the teeth 3518b, and a second position, in which the cam block 3002 is caused to move proximally relative to the first position. In this second position, the correspondingly-shaped recesses 3002a are locked in engagement with the teeth 3518b of the keying tube 3518. Movement of the cam block 3002 between the first and second positions is caused by the surfaces 3002c of the cam block 3002 engaging the respective cam surfaces 3050a of the upper jaw 3050 as the upper jaw 3050 is moved relative to the lower jaw 3080, as will be described in additional detail below.

FIG. 18 also illustrates a distal reload contact 3820 and a proximal reload contact 3830. The distal reload contact 3830 contacts and communicates with the proximal reload contact in order to provide signals that the distal portion 3111d has been rotated relative to the joint portion 3111b back to its initial position upon a new staple cartridge being loaded in the surgical device.

Additional details of the various surfaces and recesses that engage the keying tube 3518 and the idler gear 3562 are illustrated in FIG. 19. Specifically, FIG. 19 shows, in the central-most region of the surgical device 3000, a longitudinally-disposed central bore 3521 of the threaded clamping screw 3520. As set forth above, the longitudinally-disposed central bore 3521 of the threaded clamping screw 3520 has a cross-section that is configured to receive and rotatably engage a correspondingly-shaped end of the gear shaft 3512, such that rotation of the gear shaft 3512 causes rotation of the threaded clamping screw 3520.

Located radially outside of the longitudinally-disposed central bore 3521 of the threaded clamping screw 3520 is shown the proximal face 30028 of the proximal member 30029 of the cam block 3002. The proximal face 30028 includes the recesses 3002a. As set forth above, the recesses 3002a are configured to selectively engage with teeth 3518b of the keying tube 3518. Since the keying tube 3518 is non-rotatably arranged within the jaw portion 3111a, engagement of the recesses 3002a of the proximal member 30029 of the cam block 3002 with the teeth 3518b of the keying tube 3518 prevent relative rotation between the cam block 3002 and the keying tube 3518.

Located radially outside of the proximal face 30028 of the proximal member 30029 of the cam block 3002 is shown the proximally-facing surface 3009a of the jaw body housing 3009. The proximally-facing surface 3009a of the jaw body housing 3009 includes the recesses 3009b. As set forth above, the recesses 3009b are configured to selectively engage a distal end of the idler gear 3562. When the recesses 3009b of the jaw body housing 3009 are engaged with the distal end of the idler gear 3562, the idler gear 3562 is prevented from rotating relative to the jaw body housing 3009. As set forth above, the idler gear 3562 is biased distally by the spring washers 3001 so as to seat within the recesses 3009b. When the cam block 3002 is moved proximally to a position at which the proximal face 30028 of the cam block 3002 is proximal relative to the proximally-facing surface 3009a of the jaw body housing 3009, the idler gear 3562 is moved by the cam block 3002 out of the recesses 3009b and is free to rotate relative thereto.

In operation, the jaw portion 3111a is maintained in an initial position in which it is axially aligned with the shaft portion 3111c. In this position, the surgical device 3111 may be inserted, e.g., through a trocar or cannula, into a surgical site. Depending on the position of the incision and the tissue to be clamped, stapled and cut, the user may then articulate the jaw portion 3111a relative to the shaft portion 3111c, either in the manner set forth above or in any other manner.

Once the jaw portion 3111a is articulated about the pin 3505 to a desired position, the first jaw 3050 may be moved, e.g., opened, relative to the second jaw 3080 so as to enable a section of tissue to be disposed therebetween. In order to open the first jaw 3050 relative to the second jaw 3080, the gear element 3504 may be caused to rotate in a counter-clockwise direction (when viewed from above) about the pin 3505. By virtue of its engagement with the gear element 3506b, the counter-clockwise rotation of the gear element 3504 causes the gear element 3506b to rotate in a clockwise direction (for the sake of simplicity, all references herein to a rotational direction, e.g., clockwise or counterclockwise, refer to a view from the proximal end of the surgical device towards the distal end of the surgical device 11, unless otherwise noted; furthermore, it should be recognized that, while the disclosure hereinbelow includes, for each of the components of the surgical device 11, various references to rotational directions in order to perform a specific function, these directions are merely exemplary because certain components may be differently configured, e.g., threaded portions may have a right-hand thread as opposed to a left-hand thread, etc., such that the rotational directions set forth herein may be reversed in order to perform the same below-described functions). Since the gear element 3506b and the gear element 3506a are fixed features of the gear shaft 3506, rotation of the gear element 3506b in the clockwise direction causes the gear element 3506a to also rotate in a clockwise direction. By virtue of its engagement with the gear element 3512a of gear shaft 3512, the clockwise rotation of the gear element 3506a causes the gear element 3512a and the gear shaft 3512, of which gear element 3512a is a fixed feature, to rotate in a counter-clockwise direction.

Due the engagement of the distal end of the gear shaft 3512 with the threaded clamping screw 3520, rotation of the gear shaft 3512 in the counter-clockwise direction causes the threaded clamping screw 3520 to also rotate in the counter-clockwise direction. Since the inner shaft 3524 is threadedly engaged with the outer threads of the threaded clamping screw 3520, rotation of the threaded clamping screw 3520 in a counter-clockwise direction causes the inner shaft 555 to move in a distal direction within the slots 5111 of the first and second jaws 3050 and 3080, respectively. This distal movement of the inner shaft 3524 allows the first and second jaws to move, e.g., open, relative to each other. Additional details of this clamping arrangement may be found, for example, in Applicant's co-pending U.S. patent application Ser. No. 11/191,851, entitled "Surgical Device," filed Jul. 27, 2005, the disclosure of which is hereby incorporated by reference in its entirety.

Also, the opening of the first and second jaws 3050, 3080 relative to each other allows the cam block 3002 and the idler gear 3562 to move distally. Specifically, as the jaws are opened relative to each other, the cam block 3002 and the idler gear 3562 are moved distally until the recesses 3002a are spaced apart from and out of engagement with the teeth 3518b. Also, distal movement of the cam block 3002 causes the proximal face 30028 of the cam block 3002 to withdraw from the distal face of the idler gear 3562, such that the biasing force of the spring washers 3001 causes the idler gear 3562 to move distally. Continued distal movement of the idler gear 3562 eventually causes the distal face of the idler gear 3562 to engage the recesses 3009b of the jaw body housing 3009, until the idler gear 3562 is prevented from rotating relative to the keying tube 3518.

Once the first and second jaws 3050, 3080 have been opened sufficiently, the jaw portion 3111a, or at least a portion thereof, e.g., the distal portion 3111d, may be rotated about its longitudinal axis. Specifically, in the embodiment shown, the distal portion 3111d may be rotated relative to the joint portion 3111b about the longitudinal axis of the joint portion 3111b, e.g., illustrated as axis D. Referring to FIG. 17, in order to rotate the distal portion 3111d in a counter-clockwise direction relative to the joint portion 3111b about the longitudinal axis of the joint portion 3111b, the gear element 3554 may be caused to rotate in a clockwise direction (when viewed from above) about the pin 3505. By virtue of its engagement with the gear element 3556b, the clockwise rotation of the gear element 3554 causes the gear element 3556b to rotate in a clockwise direction. Since the gear element 3556b and the gear element 3556a are fixed features of the gear shaft 3556, rotation of the gear element 3556b in the clockwise direction causes the gear element 3556a to also rotate in a clockwise direction. By virtue of its engagement with the idler gear 3562, the clockwise rotation of the gear element 3556a causes the idler gear 3562 to rotate in a counter-clockwise direction. Since the idler gear is maintained in its first position, the distal end of the idler gear 3562 is locked in engagement with the correspondingly-shaped opening 3009b of the jaw body housing 3009. Thus, the rotation of the idler gear 3562 in the counter-clockwise direction about the central axis of the idler gear 3562 causes the jaw body housing 3009 (and all of the components distal thereto, to rotate in the counter-clockwise direction relative to the joint portion housing 3715 about the longitudinal axis D. It is noted that the arrangement of the cam block 3002 and the idler gear 3562 in this embodiment is such that firing of the staple cartridge may not occur with the jaws open—rather, upon closure of the jaws relative to each other, the staple cartridge may be fired, as set forth below.

Once the jaw portion 3111a, or a portion thereof, is rotated in this manner about the longitudinal axis D to a desired position, the jaws 3050, 3080 may be closed, e.g., so as to clamp a section of tissue that is disposed therebetween. To perform this operation, the gear element 3504 may be caused to rotate in a clockwise direction (when viewed from above) about the pin 3505. By virtue of its engagement with the gear element 3506b, the clockwise rotation of the gear element 3504 causes the gear element 3506b to rotate in a counter-clockwise direction. Since the gear element 3506b and the gear element 3506a are fixed features of the gear shaft 3506, rotation of the gear element 3506b in the counter-clockwise direction causes the gear element 3506a to also rotate in a counter-clockwise direction. By virtue of its engagement with the gear element 3512a of gear shaft 3512, the counter-clockwise rotation of the gear element 3506a causes the gear element 3512a and the gear shaft 3512, of which gear element 3512a is a fixed feature, to rotate in a clockwise direction.

Due the engagement of the distal end of the gear shaft 3512 with the threaded clamping screw 3520, rotation of the gear shaft 3512 in the clockwise direction causes the threaded clamping screw 3520 to also rotate in the clockwise direction. Since the inner shaft 3524 is threadedly engaged with the outer threads of the threaded clamping screw 3520, rotation of the threaded clamping screw 3520 in a clockwise direction causes the inner shaft 555 to move in a proximal direction within the slots 5111 of the first and second jaws 3050 and 3080, respectively. This proximal movement of the inner shaft 3524 causes the first and second jaws to move, e.g., close, relative to each other.

Also, the closing of the first and second jaws 3050, 3080 relative to each other moves the cam block 3002 back to its initial position, which in turn moves the idler gear 3562 back to its initial position. Specifically, the cam block 3002 is moved proximally until the correspondingly-shaped recesses 3002a are locked in engagement with the teeth 3518b. Also, proximal movement of the cam block 3002 causes the proximal face 30028 of the cam block 3002 to push against the distal face of the idler gear 3562. In this manner, the biasing force of the spring washers 3001 is overcome in order to move the idler gear 3562 proximally until the distal end of the idler gear 3562 is disengaged from the correspondingly-shaped recesses 3009b on the proximally-facing surface of the jaw body housing 3009. With the jaws closed, the idler gear 3562 is free to rotate about the keying tube 3518.

Once a section of tissue has been clamped between the first and second jaws 3050, 3080, the section of tissue may be cut and/or stapled. It should be recognized that, while the present invention is illustrated as using both cutting and stapling elements, the surgical device 11 may employ only one such element, or else may employ a different type of surgical instrument.

Before the surgical device 11 is inserted into a patient's body, a staple cartridge is provided within the second jaw 3080. In an embodiment, the surgical device 11 is a single-use device, in which the staple cartridge is integral to the second jaw 3080. Alternatively, the surgical device 11 may have a replaceable staple cartridge, e.g., replaceable staple cartridge 600 as illustrated in FIG. 3(f), thereby permitting the surgical device 11 to be used numerous times with different staple cartridges. In this embodiment, if the surgical device 11 is being used for the first time, the staple cartridge 600 may be pre-installed during manufacture and assembly of the surgical device 11, or else may be installed by the user just prior to using the surgical device 11. If the surgical device 11 is being used for the second or more time, the staple cartridge 600 may be installed by the user just prior to using the surgical device 11. When the staple cartridge 600 is inserted into the second jaw 3080, the distal end 35682 of the longitudinal rod 3568 is received within the proximally-facing opening 605d of the wedge driver 605.

Referring to FIG. 17, in order to fire the stapling cartridge, the gear element 3554 may be caused to rotate in a clockwise direction (when viewed from above) about the pin 3505. By virtue of its engagement with the gear element 3556b, the clockwise rotation of the gear element 3554 causes the gear element 3556b to rotate in a clockwise direction. Since the gear element 3556b and the gear element 3556a are fixed features of the gear shaft 3556, rotation of the gear element 3556b in the clockwise direction causes the gear element 3556a to also rotate in a clockwise direction. By virtue of its engagement with the idler gear 3562, the clockwise rotation of the gear element 3556a causes the idler gear 3562 to rotate in a counter-clockwise direction. Since the idler gear is free to rotate about the keying tube 3518, the rotation of the idler gear 3562 in the counter-clockwise direction about the central axis of the idler gear 3562 causes the gear shaft 3564 to rotate in a clockwise direction. The engagement of the recess 35641 at the distal end of the gear shaft 3564 with the correspondingly-shaped proximal end 35681 of the longitudinal rod 3568 is such that rotation of the gear shaft 3564 in a clockwise direction causes the longitudinal rod 35681 to also rotate in a clockwise direction. The distal end 35682 of the longitudinal rod 3568 engages the opening 605d of the wedge driver 605 (shown in FIG. 3(f)). The wedge driver 605 rotates so as to drive a stapling/cutting wedge along a staple cartridge, such as described hereinabove.

It should be recognized that, according to various embodiments of the present invention, the blade 51 and the wedge 603 may be moved in either a proximal or a distal direction in order to cut and/or staple a section of tissue disposed between the first jaw 3050 and the second jaw 3080. Furthermore, it should be recognized that, according to various embodiments of the present invention, any mechanical arrangement that is configured to move the blade 51 and the wedge 603 in order to cut and/or staple a section of tissue disposed between the first jaw 3050 and the second jaw 3080 may be employed.

Once the section of tissue may be cut and/or stapled, the surgical device 11 may be employed to return the wedge 603 and the blade 51 to their initial positions. This may be particularly desirable when the surgical device 11 employs replaceable staple cartridges, e.g., replaceable staple cartridge 600 as illustrated in FIG. 3(f), thereby permitting the surgical device 11 to be used numerous times with different staple cartridges. Once the wedge 603 and the blade 51 have been moved to their initial positions, the surgical device 11 may be used for a second or more time. To do so, the user may remove the spent staple cartridge 600 and insert in the surgical device 11 a new staple cartridge 600, the distal end of the longitudinal rod 3568 being received within the proximally-facing opening 605d of the wedge driver 605 of the new staple cartridge 600. Of course, it should be recognized that this step of returning the wedge 603 and the blade 51 to their initial positions may be performed either prior to, or subsequent to, removal of the surgical device 11 from the patient's body.

In order to return the wedge 603 and the blade 51 to their initial positions, the gear element 3554 may be caused to rotate in a counter-clockwise direction (when viewed from above) about the pin 3505. By virtue of its engagement with the gear element 3556b, the counter-clockwise rotation of the gear element 3554 causes the gear element 3556b to rotate in a counter-clockwise direction. Since the gear element 3556b and the gear element 3556a are fixed features of the gear shaft 3556, rotation of the gear element 3556b in the counter-clockwise direction causes the gear element 3556a to also rotate in a counter-clockwise direction. By virtue of its engagement with the idler gear 3562, the counter-clockwise rotation of the gear element 3556a causes the idler gear 3562 to rotate in a clockwise direction. Since the idler gear is free to rotate about the keying tube 3518, the rotation of the idler gear 3562 in the clockwise direction about the central axis of the idler gear 3562 causes the gear shaft 3564 to rotate in a counter-clockwise direction. The engagement of the recess 35641 at the distal end of the gear shaft 3564 with the correspondingly-shaped proximal end 35681 of the longitudinal rod 3568 is such that rotation of the gear shaft 3564 in a counter-clockwise direction causes the longitudinal rod 3568 to also rotate in a counter-clockwise direction. The distal end 35682 of the longitudinal rod 3568 engages the opening 605d of the wedge driver 605 (shown in FIG. 3(f)), and counter-clockwise rotation of the wedge driver 605 moves the wedge 603 back to its initial position so that the surgical device may be ready to accommodate a new staple cartridge 600, if appropriate.

Once the wedge 603 has been moved back to its initial position, the first jaw 3050 may again be moved, e.g., opened, relative to the second jaw 3080 so as to release the stapled sections of the tissue from therebetween. In order to open the first jaw 3050 relative to the second jaw 3080, the gear element 3504 may be caused to rotate in a counter-clockwise direction (when viewed from above) about the pin 3505. The counter-clockwise rotation of the gear element 3504 causes the gear element 3506b to rotate in a clockwise direction, which in turn causes the gear element 3506a to also rotate in a clockwise direction. The clockwise rotation of the gear element 3506a causes the gear element 3512a and the gear shaft 3512, of which gear element 3512a is a fixed feature, to rotate in a counter-clockwise direction. The rotation of the gear shaft 3512 in the counter-clockwise direction causes the threaded clamping screw 3520 to also rotate in the counter-clockwise direction, which in turn causes the inner shaft 555 to move in a distal direction within the slots 5111 of the first and second jaws 3050 and 3080, respectively. This distal movement of the inner shaft 3524 allows the first and second jaws to move, e.g., open, relative to each other.

Again, the opening of the first and second jaws 3050, 3080 relative to each other allows the cam block 3002 and the idler gear 3562 to move distally. Specifically, as the jaws are opened relative to each other, the cam block 3002 and the idler gear 3562 are moved distally until the recesses 3002a are spaced apart from and out of engagement with the teeth 3518b. Also, distal movement of the cam block 3002 causes the proximal face 30028 of the cam block 3002 to withdraw from the distal face of the idler gear 3562, such that the biasing force of the spring washers 3001 causes the idler gear 3562 to move distally. Continued distal movement of the idler gear 3562 eventually causes the distal face of the idler gear 3562 to engage the recesses 3009b of the jaw body housing 3009, until the idler gear 3562 is prevented from rotating relative to the keying tube 3518.

Once the first and second jaws 3050, 3080 have been opened sufficiently to release the section of tissue clamped therebetween, the jaw portion 3111a, or at least a portion thereof, e.g., the distal portion 3111d, may be rotated about its longitudinal axis back to its original, e.g., un-rotated, position. Referring to FIG. 17, in order to rotate the distal portion 3111d in a clockwise direction relative to the joint portion 3111b, the gear element 3554 may be caused to rotate in a counter-clockwise direction (when viewed from above) about the pin 3505 which in turn causes the gear element 3556b to rotate in a counter-clockwise direction. Rotation of the gear element 3556b in the counter-clockwise direction causes the gear element 3556a to also rotate in a counter-clockwise direction, which in turn causes the idler gear 3562 to rotate in a clockwise direction. Since the idler gear 3562 is maintained in its first position, the distal end of the idler gear 3562 is locked in engagement with the correspondingly-shaped recesses 3009b of the jaw body housing 3009. Thus, the rotation of the idler gear 3562 in the clockwise direction causes the jaw body housing 3009, and all of the components distal thereto, to rotate in the clockwise direction relative to the joint portion housing 3715. Of course, while this "return" rotation is described hereinabove as being in the clockwise direction, the direction of rotation in this step will be the opposite of whatever direction of rotation was selected by an operator when the jaw portion 3111a (or at least a portion thereof, e.g., the distal portion 3111d) was initially rotated.

Once the jaw portion 3111a, or a portion thereof, is rotated in this manner about the longitudinal axis D back to its initial position, the jaws 3050, 3080 may be closed, e.g., so as to enable the surgical device 11 to be removed from the patient's body via the opening, e.g., the cannula, through which it was originally introduced. To perform this operation, the gear element 3504 may be caused to rotate in a clockwise direction (when viewed from above) about the pin 3505. The clockwise rotation of the gear element 3504 causes the gear element 3506b to rotate in a counter-clockwise direction. Rotation of the gear element 3506b in the counter-clockwise direction causes the gear element 3506a to also rotate in a counter-clockwise direction. The counter-clockwise rotation of the gear element 3506a causes the gear element 3512a and the gear shaft 3512, of which gear element 3512a is a fixed feature, to rotate in a clockwise direction.

Rotation of the gear shaft 3512 in the clockwise direction causes the threaded clamping screw 3520 to also rotate in the clockwise direction. Rotation of the threaded clamping screw 3520 in a clockwise direction causes the inner shaft 555 to move in a proximal direction within the slots 5111 of the first and second jaws 3050 and 3080, respectively. This proximal movement of the inner shaft 3524 causes the first and second jaws to move, e.g., close, relative to each other.

With the first and second jaws 3050, 3080 closed relative to each other, the user may then articulate the jaw portion 3111a relative to the shaft portion 3111c back to its initial position, e.g., with the jaw portion 3111a being axially aligned relative to the shaft portion 3111c. With the jaw portion 3111a being again axially aligned relative to the shaft portion 3111c, the surgical device 11 may be withdrawn from the surgical site. Of course, it should be recognized that the surgical device 11 of the present invention may be returned to its initial positions, e.g., rotation, articulation, etc., either prior to or after being removed from a patient's body.

Those skilled in the art will appreciate that numerous modifications of the exemplary embodiment described hereinabove may be made without departing from the spirit and scope of the present invention. Although exemplary embodiments of the present invention have been described and disclosed in detail herein, it should be understood that this invention is in no sense limited thereby.

The invention claimed is:

1. A surgical device, comprising:
    a first jaw in opposed correspondence to a second jaw, the first and second jaws pivotably connected to each other;
    a first driver configured to be coupled to a first rotatable drive shaft;
    a second driver configured to be coupled to a second rotatable drive shaft;
    a horizontal driver element having a proximal end and a distal end, the proximal end configured to be engaged to the first rotatable drive shaft of the first driver and the distal end configured to include an opening;
    a first rotatable clamp element having a first end, a second end, and a third end, the first end pivotably connected to the opening of the horizontal driver element, wherein the third end of the first rotatable clamp element is pivotably connected to the first jaw; and
    a second rotatable clamp element, the second end of the first rotatable clamp element being pivotably connected to a proximal end of the second rotatable clamp element, wherein a distal end of the second rotatable clamp element is pivotably connected to the second jaw;
    wherein rotation of the first rotatable drive element causes the horizontal driver element to move parallel to the second jaw, which in turn causes rotation of the first rotatable clamp element;
    wherein the rotation of the first rotatable clamp element causes a downward movement of the second rotatable clamp element; and
    wherein the downward movement of the second rotatable clamp element causes the first jaw to rotate relative to the second jaw into a closed position.

2. The surgical device according to claim 1, wherein the first driver extends through a shaft to a first drive socket connected to a first motor that functions to open and close the first jaw relative to the second jaw.

3. The surgical device according to claim 2, wherein the second driver extends through the shaft to a second drive socket connected to a second motor that functions to actuate a cutting and stapling element disposed within the second jaw.

4. The surgical device according to claim 1, wherein the first and second rotatable drive shafts meshingly engage first and second gear trains, respectively.

5. The surgical device according to claim 4, wherein the first gear train has a first gear element arrangement and the second gear train has a second gear element arrangement.

6. The surgical device according to claim 4, wherein the first gear train includes:
a first gear element supported on a distal end of the first rotatable drive shaft;
a coupler gear meshingly engaged with the first gear element of the first gear train; and
a second gear element rotatably supported in the second jaw and meshingly engaged with the coupler gear.

7. The surgical device according to claim 4, wherein the second gear train includes:
a first gear element supported on a distal end of the second rotatable drive shaft;
a coupler gear meshingly engaged with the second gear element of the second gear train; and
a second gear element rotatably supported in the second jaw and meshingly engaged with the coupler gear.

8. The surgical device according to claim 1, wherein the second jaw includes a knife member.

9. The surgical device according to claim 8, wherein the knife member is movable within the knife jaw, such that the surgical member is prevented from moving within the second jaw unless the first jaw is in a closed position relative to the second jaw.

10. The surgical device according to claim 8, wherein when the first jaw is an open position relative to the second jaw, the first and second jaws are rotatable relative to one of the first rotatable drive shaft and the second rotatable drive shaft.

11. A surgical device, comprising:
a first jaw;
a second jaw in opposed correspondence to the first jaw, the second jaw including a knife member;
an elongate shaft pivotably coupled to the first and second jaws, the elongate shaft defining a longitudinal axis therethrough;
a first driver configured to be coupled to a first rotatable drive shaft;
a second driver configured to be coupled to a second rotatable drive shaft;
a first gear train having a first gear element arrangement; and
a second gear train having a second gear element arrangement;
wherein the first and second gear trains meshingly engage the first and second rotatable drive shafts, respectively, such that the first and second gear trains enable rotation the first and second jaws relative to the longitudinal axis defined by the shaft; and
wherein the knife member is movable within the second jaw, and wherein the knife member is prevented from moving within the second jaw unless the first jaw is in a closed position relative to the second jaw.

12. The surgical device according to claim 11, wherein when the first jaw is an open position relative to the second jaw, the first and second jaws are rotatable relative to the elongate shaft.

13. The surgical device according to claim 11, wherein the first gear train includes:
a first gear element supported on a distal end of the first rotatable drive shaft;
a coupler gear meshingly engaged with the first gear element of the first gear train; and
a second gear element rotatably supported in the second jaw and meshingly engaged with the coupler gear.

14. The surgical device according to claim 11, wherein the second gear train includes:
a first gear element supported on a distal end of the second rotatable drive shaft;
a coupler gear meshingly engaged with the second gear element of the second gear train; and
a second gear element rotatably supported in the second jaw and meshingly engaged with the coupler gear.

15. The surgical device according to claim 11, wherein the first gear train engages a plurality of first gears selectively engageable with a plate, a push block, and a threaded screw, such that the threaded screw is longitudinally arranged and configured to rotate about the longitudinal axis defined by the elongate shaft when the plurality of first gears are actuated.

16. The surgical device according to claim 15, wherein the second gear train engages a plurality of second gears selectively engageable with a longitudinal rod and a wedge driver, the longitudinal rod having a spring mechanism and positioned parallel to the threaded screw.

17. The surgical device according to claim 16, wherein the wedge driver is configured to rotate so as to drive a stapling/cutting wedge along a staple cartridge positioned within the second jaw.

18. The surgical device according to claim 11, further comprising a cam block moveable between a proximal position and a distal position, wherein the cam block includes a surface, wherein the cam block is moved between its proximal and distal positions by engagement of the surface thereof with a surface of one of the first and second jaws when the first and second jaws are moved relative to each other.

19. The surgical device according to claim 11, wherein the first and second element gear arrangements include an idler gear that is selectively engageable based upon a position of the first jaw relative to the second jaw.

20. A surgical device, comprising:
a first jaw;
a second jaw in opposed correspondence to the first jaw;
an elongate shaft pivotably coupled to the first and second jaws, the elongate shaft defining a longitudinal axis therethrough;
a first driver configured to be coupled to a first rotatable drive shaft;
a second driver configured to be coupled to a second rotatable drive shaft;
a first gear train having a first gear element arrangement; and
a second gear train having a second gear element arrangement;
wherein the second jaw includes a wedge member and a wedge driver; and
wherein the first gear train engages a plurality of first gears selectively engageable with a plate, a push block, and a threaded screw, such that the threaded screw is longitudinally arranged and configured to rotate about the longitudinal axis defined by the shaft when the plurality of first gears are actuated.

21. The surgical device according to claim 20, wherein the first and second gear trains meshingly engage the first and second rotatable drive shafts, respectively, such that the first and second gear trains enable rotation the first and second jaws relative to the longitudinal axis defined by the elongate shaft.

22. The surgical device according to claim 20, wherein the wedge member is slidably supported within the second jaw and the wedge driver is rotatably supported within the second jaw, the wedge driver being threadably connected to the wedge member, wherein rotation of the wedge driver results in axial translation of the wedge member.

23. The surgical device according to claim 20, wherein the first gear train includes:

a first gear element supported on a distal end of the first rotatable drive shaft;

a coupler gear meshingly engaged with the first gear element of the first gear train; and a second gear element rotatably supported in the second jaw and meshingly engaged with the coupler gear.

24. The surgical device according to claim 20, wherein the second gear train includes:

a first gear element supported on a distal end of the second rotatable drive shaft;

a coupler gear meshingly engaged with the second gear element of the second gear train; and a second gear element rotatably supported in the second jaw and meshingly engaged with the coupler gear.

25. The surgical device according to claim 20, wherein the second gear train engages a plurality of second gears selectively engageable with a longitudinal rod and a wedge driver, the longitudinal rod having a spring mechanism and positioned parallel to the threaded screw.

26. The surgical device according to claim 20, wherein the wedge member is prevented from moving within the second jaw unless the first jaw is in a closed position relative to the second jaw.

27. The surgical device according to claim 20, wherein when the first jaw is in an open position relative to the second jaw, the first and second jaws are rotatable relative to the elongate shaft.

28. The surgical device according to claim 20, further comprising a cam block moveable between a proximal position and a distal position, wherein the cam block is moved between its proximal and distal positions by engagement of the surface thereof with a surface of one of the first and second jaws when the first and second jaws are moved relative to each other.

29. The surgical device according to claim 20, further comprising an idler gear that is selectively engageable based upon a position of the first jaw relative to the second jaw.

* * * * *